(12) United States Patent
Kanamori

(10) Patent No.: US 9,808,147 B2
(45) Date of Patent: Nov. 7, 2017

(54) IMAGE PROCESSING APPARATUS AND ENDOSCOPE

(71) Applicant: Panasonic Intellectual Property Management Co., Ltd., Osaka (JP)

(72) Inventor: Katsuhiro Kanamori, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 437 days.

(21) Appl. No.: 14/542,771

(22) Filed: Nov. 17, 2014

(65) Prior Publication Data

US 2015/0141753 A1   May 21, 2015

Related U.S. Application Data

(63) Continuation of application No. PCT/JP2013/005614, filed on Sep. 24, 2013.

(30) Foreign Application Priority Data

Feb. 15, 2013   (JP) .................................. 2013-027304

(51) Int. Cl.
*A62B 1/04* (2006.01)
*H04N 9/47* (2006.01)
(Continued)

(52) U.S. Cl.
CPC ........ *A61B 1/0646* (2013.01); *A61B 1/00009* (2013.01); *A61B 1/04* (2013.01);
(Continued)

(58) Field of Classification Search
CPC ..... A61B 1/0646; A61B 1/04; A61B 1/00009; H01L 27/14629; H01L 27/14627;
(Continued)

(56) References Cited

U.S. PATENT DOCUMENTS

2003/0040668 A1   2/2003   Kaneko et al.
2012/0069181 A1   3/2012   Xue et al.
(Continued)

FOREIGN PATENT DOCUMENTS

JP   2009-210780 A   9/2009
JP   2009-246770 A   10/2009
(Continued)

OTHER PUBLICATIONS

International Search Report for corresponding International Application No. PCT/JP2013/005614 dated Dec. 24, 2013.
(Continued)

*Primary Examiner* — Jared Walker
(74) *Attorney, Agent, or Firm* — Renner Otto Boisselle & Sklar, LLP

(57) ABSTRACT

An image processing apparatus according to the present disclosure includes an illuminating section which sequentially irradiates an object with first and second illuminating light beams polarized in first and second directions. First and second polarization images are generated based on signals representing light transmitted through polarizers having the polarization transmission axis in respective directions that are parallel to, and intersect with, the first direction while the object is being irradiated with the first illuminating light beam, and third and fourth polarization images are generated based on signals representing light transmitted through polarizers having the polarization transmission axis in respective directions that are parallel to, and intersect with, the second direction while the object is being irradiated with the second illuminating light beam. A depressed object surface region is detected based on the first and second polarization images and/or the third and fourth polarization images.

13 Claims, 47 Drawing Sheets

(a)

(b)

(51) Int. Cl.
*A61B 1/06* (2006.01)
*G02B 23/26* (2006.01)
*H04N 5/225* (2006.01)
*A61B 1/00* (2006.01)
*H04N 5/235* (2006.01)
*H04N 9/04* (2006.01)
*H01L 27/146* (2006.01)
*A61B 1/04* (2006.01)
*G02B 5/20* (2006.01)
*G02B 5/30* (2006.01)
*G02B 23/24* (2006.01)
*G02B 27/28* (2006.01)

(52) U.S. Cl.
CPC ........ *G02B 23/26* (2013.01); *H01L 27/14627* (2013.01); *H01L 27/14629* (2013.01); *H04N 5/2254* (2013.01); *H04N 5/2256* (2013.01); *H04N 5/2354* (2013.01); *H04N 9/045* (2013.01); *G02B 5/201* (2013.01); *G02B 5/3083* (2013.01); *G02B 23/2407* (2013.01); *G02B 27/285* (2013.01)

(58) Field of Classification Search
CPC .... H04N 5/2254; H04N 9/045; H04N 5/2354; H04N 5/2256; G02B 23/26; G02B 5/201; G02B 27/285; G02B 5/3083; G02B 23/2407

USPC ......................................................... 348/65
See application file for complete search history.

(56) References Cited

U.S. PATENT DOCUMENTS

2012/0307028 A1 12/2012 Kanamori
2013/0135453 A1 5/2013 Kanamori
2013/0178706 A1 7/2013 Shimada et al.

FOREIGN PATENT DOCUMENTS

| JP | 2010-104424 A | 5/2010 |
| JP | 2012-024140 A | 2/2012 |
| WO | WO 2012/039086 A1 | 3/2012 |
| WO | WO 2012/073414 A1 | 6/2012 |
| WO | WO 2012/133431 A1 | 10/2012 |

OTHER PUBLICATIONS

K. Kanamori et al., "Surface inter-reflection imaging endoscope using polarized light with conventional camera", SSII2011, 17th Symposium on Sensing via Image Information, Jun. 2011, ISI-01-1 to ISI-01-8 and concise explanation.
Viktor Gruev et al., "CCD polarization imaging sensor with aluminum nanowire optical filters", Optics Express, vol. 18, No. 18, Aug. 30, 2010, pp. 19087-19094 (cited in [0097] of the specification).
Extended European Search Report for corresponding European Application No. 13875024.5 dated Dec. 17, 2015.

(a)                    (b)

(a)

(b)

| 0.000229 | 0.003312 | 0.008064 | 0.003312 | 0.000229 |
| --- | --- | --- | --- | --- |
| 0.003312 | 0.047809 | 0.116411 | 0.047809 | 0.003312 |
| 0.008064 | 0.116411 | 0.283456 | 0.116411 | 0.008064 |
| 0.003312 | 0.047809 | 0.116411 | 0.047809 | 0.003312 |
| 0.000229 | 0.003312 | 0.008064 | 0.003312 | 0.000229 |

(A)

(B)

(A)　　　　(B)　　　　(C)　　　　(D)

(A)

(B)

(B)

(C)

IMAGE PROCESSING APPARATUS AND ENDOSCOPE

This is a continuation of International Application No. PCT/JP2013/005614, with an international filing date of Sep. 24, 2013, which claims priority of Japanese Patent Application No. 2013-027304, filed on Feb. 15, 2013, the contents of which are hereby incorporated by reference.

BACKGROUND

1. Technical Field

The present disclosure relates to an image processing apparatus and an endoscope for use in the image processing apparatus.

2. Description of the Related Art

In the field of an endoscope which captures an image by illuminating the wall surface of an organism's organ which is covered with a mucosa with light, not only a variation in the surface color of the object but also its micro-geometric surface texture need to be inspected. Such a surface texture is a translucent micro-geometry with an average size of approximately 0.5 to 1.0 mm and a depth of approximately 0.1 to 0.2 mm as in a gastric area in a stomach, for example. It is very difficult to capture such a micro-geometric surface texture of the object based on the shades of the light intensity when the object is observed through an endoscope. For that reason, currently, some blue pigment liquid such as an indigo carmine solution is sprinkled onto a mucosa and the surface of the mucosa, of which the grooves are filled with such a liquid, is observed based on its light intensities.

According to such an observation method, however, some liquid needs to be sprinkled onto the mucosa, and therefore, the object may bleed, the mucosa may change its color, and many other problems will arise. Thus, to observe such a micro-geometric surface as closely as possible, some people have proposed a polarization endoscope which uses a polarized light source and a polarization image sensor (see Japanese Laid-Open Patent Publication No. 2009-246770, for example).

SUMMARY

According to the conventional technique that uses polarized light as disclosed in Japanese Laid-Open Patent Publication No. 2009-246770, an object is irradiated with illuminating light having a particular polarization component, two images are captured based on polarization components of the light returning from the object, which are respectively parallel and perpendicular to the illuminating light, and a variation in surface shape is calculated using those images captured.

An embodiment of an image processing apparatus according to the present disclosure detects a depressed region on the surface of the object in a polarization image capturing mode, thereby obtaining an image which represents the depressed region on the object's surface in an enhanced form.

An image processing apparatus according to an aspect of the present disclosure includes: an illuminating section which sequentially irradiates an object with a first illuminating light beam that is polarized in a first direction and with a second illuminating light beam that is polarized in a second direction that intersects with the first direction in a polarization image capturing mode, and which emits the first and second illuminating light beams sequentially so that the wavelength range of the first illuminating light beam does not overlap with that of the second illuminating light beam somewhere; an image sensor including a polarization mosaic array in which a plurality of polarizers with mutually different polarization transmission axis directions are arranged and a photosensing element array which receives light that has been transmitted through each polarizer and which outputs a signal; a polarization mosaic processing section which obtains, in the polarization image capturing mode, a first polarization image to be generated based on a signal representing light that has been transmitted through a polarizer that has the polarization transmission axis in a direction parallel to the first direction while the object is being irradiated with the first illuminating light beam, a second polarization image to be generated based on a signal representing light that has been transmitted through a polarizer that has the polarization transmission axis in a direction intersecting with the first direction while the object is being irradiated with the first illuminating light beam, a third polarization image to be generated based on a signal representing light that has been transmitted through a polarizer that has the polarization transmission axis in a direction parallel to the second direction while the object is being irradiated with the second illuminating light beam, and a fourth polarization image to be generated based on a signal representing light that has been transmitted through a polarizer that has the polarization transmission axis in a direction intersecting with the second direction while the object is being irradiated with the second illuminating light beam; a depressed region detecting section which detects a depressed region on the surface of the object based on both the first and second polarization images that form one pair and the third and fourth polarization images that form another pair; and an image forming section which forms an image that represents the depressed region on the object's surface in an enhanced form.

An image processing apparatus according to another aspect of the present disclosure includes: an illuminating section which sequentially irradiates an object with a first white illuminating light beam that is polarized in a first direction and with a second white illuminating light beam that is polarized in a second direction that intersects with the first direction in a polarization image capturing mode; an image sensor including a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each polarizer and each color filter and which outputs a signal; a polarization mosaic processing section which obtains, in the polarization image capturing mode, a first polarization image to be generated based on a signal representing light that has been transmitted through a polarizer that has the polarization transmission axis in a direction parallel to the first direction while the object is being irradiated with the first white illuminating light beam, a second polarization image to be generated based on a signal representing light that has been transmitted through a polarizer that has the polarization transmission axis in a direction intersecting with the first direction while the object is being irradiated with the first white illuminating light beam, a third polarization image to be generated based on a signal representing light that has been transmitted through a polarizer that has the polarization transmission axis in a direction parallel to the second direction while the object is being irradiated with the second white illuminating light beam, and a fourth polarization image to be generated based on a signal representing light that has been transmitted through a polarizer that has the polarization transmission axis in a direction intersecting with the second direction while the object is being irradiated with the second white illuminating light beam; a depressed region detecting section which detects a depressed region on the surface of the object based on both the first and second polarization images that form one pair and the third and fourth polarization images that form another pair; and an image forming section which forms an image that represents the depressed region on the object's surface in an enhanced form.

An endoscope according to an aspect of the present disclosure is designed to be used in an image processing apparatus according to any of the embodiments described above, and includes: an illuminating section which sequentially irradiates an object with a first illuminating light beam that is polarized in a first direction and with a second illuminating light beam that is polarized in a second direction that intersects with the first direction in a polarization image capturing mode, and which emits the first and second illuminating light beams sequentially so that the wavelength range of the first illuminating light beam does not overlap with that of the second illuminating light beam somewhere; and an image sensor including a polarization mosaic array in which a plurality of polarizers with mutually different polarization transmission axis directions are arranged and a photosensing element array which receives light that has been transmitted through each polarizer and which outputs a signal.

An endoscope according to another aspect of the present disclosure is designed to be used in an image processing apparatus according to any of the embodiments described above, and includes: an illuminating section which sequentially irradiates an object with a first white illuminating light beam that is polarized in a first direction and with a second white illuminating light beam that is polarized in a second direction that intersects with the first direction in a polarization image capturing mode; and an image sensor including a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each polarizer and each color filter and which outputs a signal;

An image processing apparatus according to still another aspect of the present disclosure includes: an illuminating section which irradiates an object with a circularly polarized illuminating light beam; an image sensor including a quarter-wave plate, a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each polarizer and each color filter and which outputs a signal, wherein the quarter-wave plate is arranged closer to the object than the polarization mosaic array is; a polarization mosaic processing section which obtains a first polarization image to be generated based on a signal representing light that has been transmitted through a polarizer, of which the polarization transmission axis is parallel to the polarization plane of a linearly polarized light beam that has been transformed by getting the illuminating light beam that has returned from the object transmitted through the quarter-wave plate, and which also obtains a second polarization image to be generated based on a signal representing light that has been transmitted through a polarizer, of which the polarization transmission axis intersects with the polarization plane; and an image forming section which forms an image that represents the depressed region on the object's surface in an enhanced form based on the pair of the first and second polarization images.

An endoscope according to the present disclosure is designed to be used in this image processing apparatus, and includes: an illuminating section which irradiates an object with a circularly polarized illuminating light beam; and an image sensor including a quarter-wave plate, a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each polarizer and each color filter and which outputs a signal, wherein the quarter-wave plate is arranged closer to the object than the polarization mosaic array is.

According to an embodiment of the present disclosure, the object is sequentially irradiated with a first illuminating light beam that is polarized in a first direction and with a second illuminating light beam that is polarized in a second direction that intersects with the first direction in a polarization image capturing mode. Thus, information about the micro-geometry and tilt of the object's surface can be obtained separately from an ordinary object image. As a result, an image similar to the one in which some blue pigment liquid such as an indigo carmine solution is sprinkled onto a mucosa (i.e., an image in which the depressed region is represented in an enhanced form) can be synthesized.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

DETAILED DESCRIPTION

Figure 1:
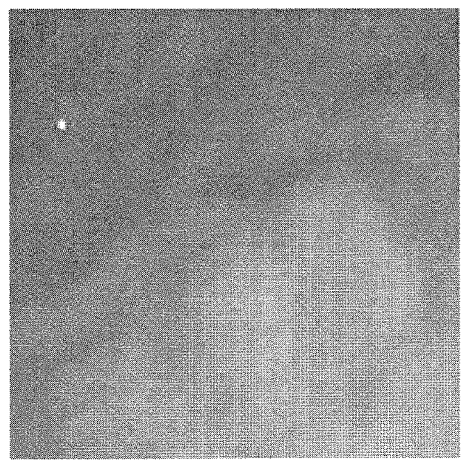
FIG. 1 is images representing the mucosa of a stomach as observed through an endoscope.
Figure 1:
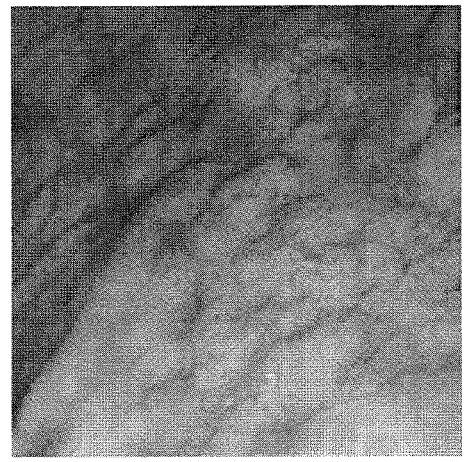

FIG. 1 is an image representing the surface mucosa of a human stomach as observed through an endoscope. Specifically, potion of (a) FIG. 1(a) shows a normal color image, in which the surface appears to have only gentle ups and downs. That is to say, according to ordinary color image processing, it is difficult to sense transparent or translucent micro-geometry on the surface of an organ through an endoscope which is designed to inspect digestive organs, for example. In this description, the "ordinary color image processing" refers hereinafter to processing for obtaining a color light intensity image by irradiating the object with non-polarized white light. A color image thus obtained will be hereinafter referred to as a "color light intensity image" or simply a "light intensity image" and a shooting session for obtaining such a color light intensity image will be sometimes hereinafter referred to as a "color light intensity shooting session".

On the other hand, potion (b) of FIG. 1 shows a color image that was obtained after an indigo carmine solution had been sprinkled. In this image, the micro-geometric surface texture (with a size of about 0.5 to 1.0 mm and a depth of about 0.1 to 0.2 mm) is sensible clearly.

Figure 2:
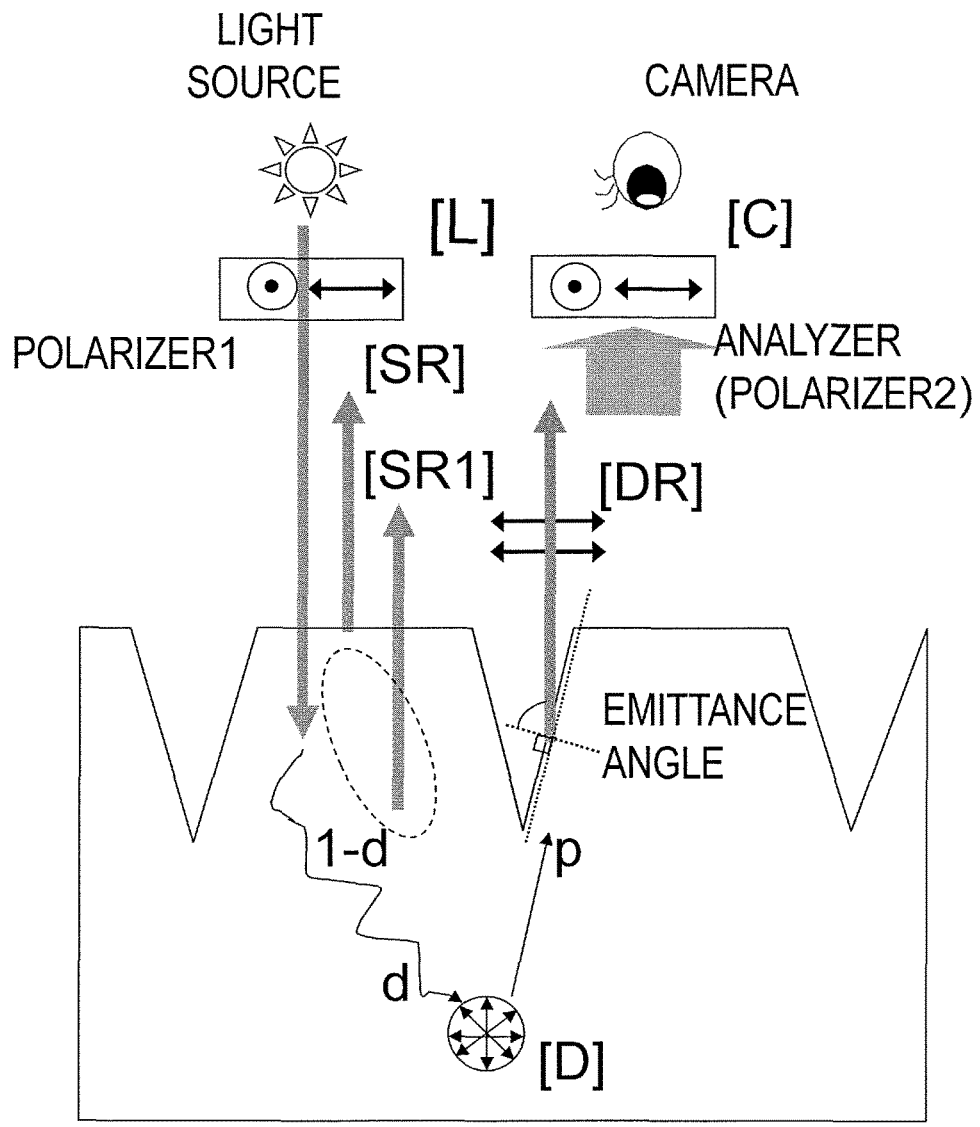
FIG. 2 illustrates, as a model, a cross section of a micro-geometric structure on the surface mucosa of an organ.

FIG. 2 schematically illustrates a cross section of a micro-geometric structure on the surface of an organ such as a stomach or bowels. In general, the micro-geometric grooves on the surface of a stomach or bowels would be an iterative arrangement of trapezoidal upwardly projecting portions. A depressed region located between two adjacent projections is typically a tiny "groove" running in a certain direction. A number of such grooves may run in substantially the same direction locally but may form a complex curved pattern or any other pattern globally. The micro-geometry on the surface of an object may actually include dotted depressions or projections. In this description, those depressions of such a micro-geometry will be simply referred hereinafter to as "grooves" or "depressed grooves". FIG. 2 schematically illustrates a cross section which crosses several grooves that are present within a narrow area on the surface of the object. In the following description, the depressions and projections shown in FIG. 2 may be supposed to run in the direction coming out of the paper for the sake of simplicity.

When observed through an endoscope, the object is illuminated with coaxial illumination (i.e., the light source is arranged in the vicinity of the shooting optical axis). That is to say, the object shown in FIG. 2 is irradiated with an illuminating light beam, and is shot, from substantially right over the object. There are roughly three types of reflected light beams to be observed by normal color light intensity shooting using such coaxial illumination. A first one of the three types is specular reflected light SR (i.e., so-called "halation") which is reflected from the surface. A second one is surface scattered light SR1 which penetrates into the medium, gets reflected from a surface layer, and then returns toward the source through the surface. And a third one is internally diffused light DR which gets multi-scattered and penetrated deeper into the medium and then gets reflected back from a surface layer toward the source. The first type of reflected light (i.e., specular reflected light) is produced only when the direction of the irradiating light and the image capturing optical axis almost satisfy the condition of regular reflection, and therefore, is produced only locally when a scene is shot through an endoscope. The color of the specular reflected light is the color of the illumination, i.e., the color white, and has very high intensity. According to the regular reflection condition described above, the object image under the specular reflected light is generally intense and bright at projections of the object's micro-geometric surface but is weak and dark at its depressions. On the other hand, the second type of reflected light (i.e., surface scattered light) and the third type of reflected light (i.e., internally diffused light) are observed all over the scene shot. The color of these two types of light is the color of the medium itself, and its intensity is not so high. However, when irradiated with any of these two types of light, the entire medium tends to shine globally.

In an ordinary shooting session, the specular reflected light of the first type is often eliminated to avoid background reflection, and the reflected light beams of the second and third types are superposed one upon the other to form a single light intensity image (as a scene shot).

Next, it will be described with reference to FIG. 2 again what phenomenon will arise when polarized light is used. In the example illustrated in FIG. 2, the object is sequentially illuminated with polarized illuminating light beams, of which the polarization directions are respectively parallel and perpendicular to the direction in which the projections and depressions of the micro-geometric surface run, thereby observing a polarized image in a parallel Nicols state and a polarized image in a crossed Nicols state.

First of all, the specular reflected component SR is regular reflected light under coaxial illumination, and therefore, maintains the same polarization state as the polarized light irradiating the object. That is why the specular reflected component SR comes to have the same polarization as the illuminating light.

Figure 3:
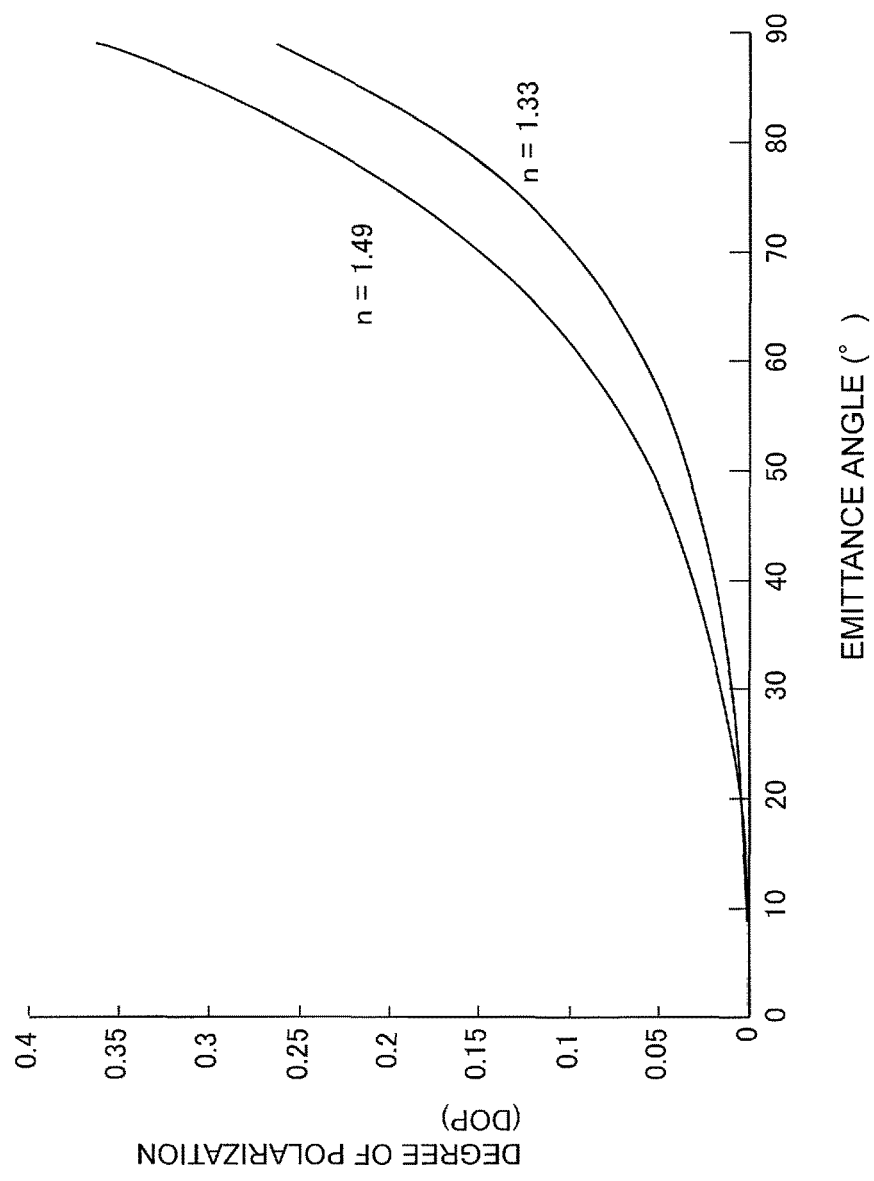
FIG. 3 is a graph showing how the degree of polarization DOP changes with the emittance angle at which light goes out of the medium according to the Fresnel theory.

Meanwhile, the surface scattered light SR1 returns through the surface while maintaining the polarization property of the illuminating light, too. That is why SR and SR1 have substantially the same polarization property as the illuminating polarized light. On the other hand, the internally diffused polarized light DR has a different polarization direction from them. That polarized light that has come back after having been multi-reflected deeper into the medium has its polarization disturbed through the multi-reflection and has turned into non-polarized light (i.e., randomly polarized light) D. And that non-polarized light D comes back into the air through the surface again. This light D would pass through an ordinary flat portion as it is (i.e., as non-polarized light). If there is any groove on the surface, however, there will be a tilted boundary plane there, and therefore, the non-polarized light will pass through the surface after having gotten polarized again. The polarization direction of the polarized light beam which is going out of a medium, of which the refractive index is greater than one, into the air is determined by the Fresnel theory. FIG. 3 is a graph showing the state of a polarized light beam which is going out of a medium, of which the refractive index is greater than one, into the air. The curves shown in FIG. 3 were obtained based on the Fresnel theory. It can be seen that supposing the refractive indices of an organism (or water) and an acrylic plate, for example, which have relatively low degrees of polarization but of which the transmittance always satisfies P polarized light>S polarized light with respect to the emittance angle represented by the abscissa, are approximately 1.33 and 1.49, respectively, if the emittance angle is 70 degrees, polarized light with a degree of polarization DOP of 0.1 (i.e., less than 10%) will be observed.

Figure 4:
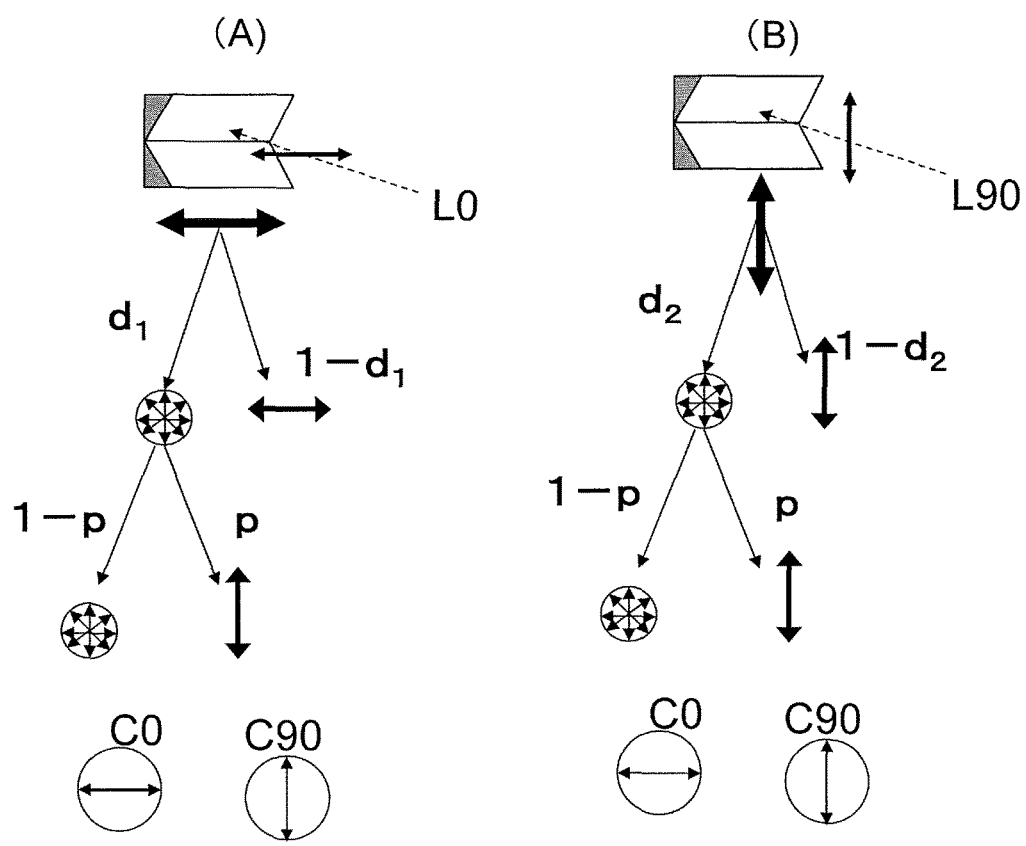
FIG. 4 illustrates the power of reflected light when polarized illuminating light is incident on a surface groove, wherein portions (A) and (B) illustrate a situation where the polarization direction of the illuminating light defines an angle of 0 degrees with respect to the groove and a situation where the polarization direction of the illuminating light defines an angle of 90 degrees with respect to the groove, respectively.
Figure 5:
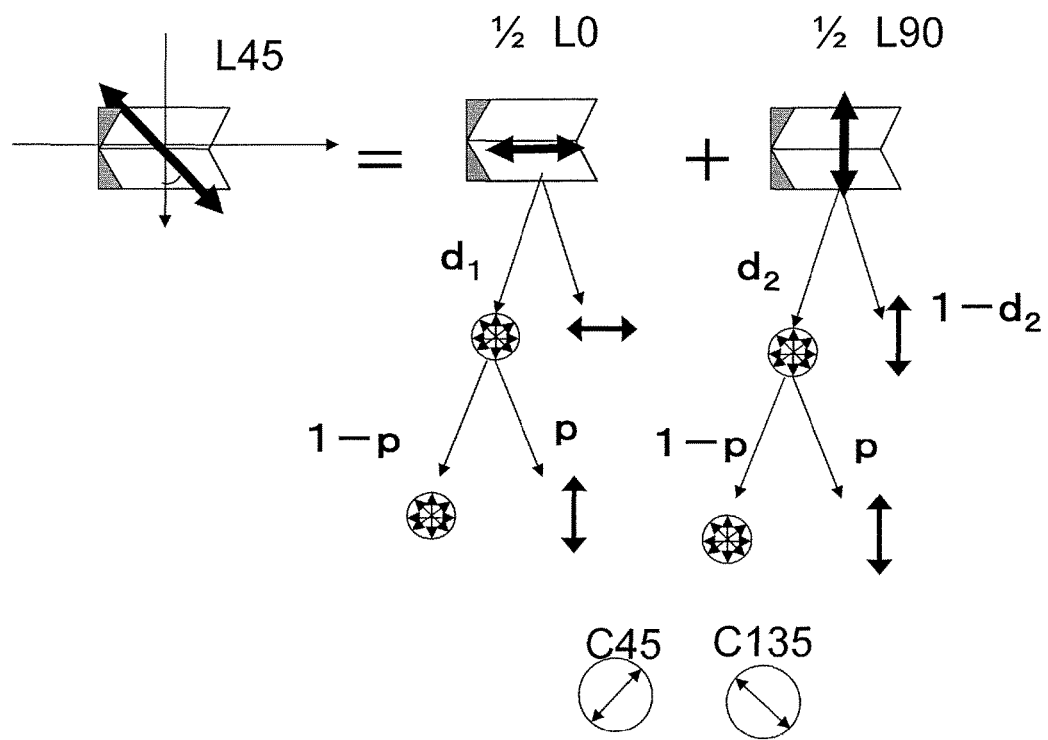
FIG. 5 illustrates the power of reflected light when polarized illuminating light is incident on a surface groove (in a situation where the polarization direction of the illuminating light defines an angle of 45 degrees with respect to the groove).

In this example, it will be considered how high the light intensity contrast ratio will be in a situation where a polarized illuminating light beam is incident on a surface groove and captured as a polarization image with absorption into the mucosa medium ignored. The polarized illuminating light is supposed to be incident with the azimuth angle of the groove fixed at 0 degrees and with the polarization direction changed into three different directions in a two-dimensional camera coordinate plane as shown in FIGS. 4 and 5. Those three different polarization directions will be indicated herein by ( L0, L90, L45), for example. The light intensities are observed with the angle of an analyzer arranged in front of the camera changed in the same way as will be indicated by (C0, C90, C45), for example. A state where L and C are in the parallel Nicols state will be indicated herein by // and a state where L and C are in the crossed Nicols state will be indicated herein by $\perp$.

(1) If L0C0(//)/L0C90($\perp$) (See Portion (A) of FIG. 4)

Supposing the power of the incident linearly polarized light is one and the ratio at which this polarized light diffuses inside the medium and turns into non-polarized light is d1, the ratio at which the polarized light is reflected with its polarization maintained such as (SR) (SR1) becomes $(1-d_1)$. Next, the ratio at which the non-polarized light in the medium turns into linearly polarized light when going out of the medium into the air again is supposed to be p and the ratio at which the non-polarized light remains non-polarized is supposed to be (1-p). If these reflected light beams are observed with a C0 polarizer (i.e., a 0 degree polarizer), the power of the linearly polarized light in the parallel state will be totally transmitted, but that of the linearly polarized light in the crossed state will be zero. And in the case of the non-polarized light, the power will be a half when observed with a linear polarizer. Consequently, the light intensity of the parallel Nicols (//) image at L0 is represented by the following Equation (1):

$$L0C0 = (1-d_1) + d_1(1-p)/2 = 1 - d_1(1+p)/2 \quad (1)$$

On the other hand, the light intensity of the crossed Nicols ($\perp$) image at L0 is represented by the following Equation (2):

$$L0C90 = d_1 p + d_1(1-p)/2 = d_1(1+p)/2 \quad (2)$$

(2) If L90C90(//)/L90C0($\perp$) (See Portion (B) of FIG. 4)

In this case, if the ratio at which the polarized light diffuses inside the medium and turns into non-polarized light is supposed to be $d_2$, then the light intensity of the parallel Nicols (//) image is represented in the same way by the following Equation (3):

$$L90C90 = (1-d_2) + d_2 p + d_2(1-p)/2 \quad (3)$$
$$= 1 - d_2(1-p)/2$$

The light intensity of the crossed Nicols ($\perp$) image is represented by the following Equation (4):

$$L90C0 = d_2(1-p)/2 \quad (4)$$

(3) If L45C45(//)/L45C135($\perp$) (See FIG. 5)

In this case, Equations (1) to (4) may be used after the polarized light has been split into a 0 degree polarized light beam and a 45 degree polarized light beam with a half power. According to the Malus' law, the light intensity of the parallel Nicols (//) image is represented by the following Equations (5) and (6) using $\cos^2$ 45 degrees.

$$L45C45 = \frac{1}{2} \times [\cos^2 45° \times \{d_1 p + (1-d_1) + d_2 p + (1-d_2)\} + d_1/2 \times (1-p) + d_2/2 \times (1-p)] = \frac{1}{2} \quad (5)$$

$$L45C135 = \frac{1}{2} \quad (6)$$

Next, in order to derive the light intensity contrast ratio in measuring the polarized light difference, suppose a situation where the polarized light has been incident on a flat medium first. In the same way, supposing linearly polarized light turns into non-polarized light in the medium at a ratio d, the reflected component with the polarization maintained will contribute at (1–d) and the non-polarized component will contribute at d/2 in the parallel Nicols state. After all, contribution will be only 1–d/2. In the crossed Nicols state, on the other hand, contribution from the non-polarized components will be only d/2.

The following Table 1 summarizes the respective light intensities of a groove region and a plane region with the angles of polarization taken into account. At the same time, their polarization differences (//–$\perp$) were also calculated and the light intensity contrast ratios were further calculated based on these light intensities. In this case, the light intensity contrast ratio is defined to be (plane region's light intensity Plane)/(groove region's light intensity Groove). To simplify the calculations, in the column of light intensity contrast ratio in Table 1, $d_1 = d_2 = d$ is supposed to be satisfied.

TABLE 1

| | Groove-region | | | Plane-region | | Contrast (Plane/ |
|---|---|---|---|---|---|---|
| | $\parallel$ | $\perp$ | $\parallel - \perp$ | $\parallel$ | $\perp$ | $\parallel - \perp$ | Groove) |
| L0 | $1 - d_1 (1+p)/2$ | $d_1(1+p)/2$ | $1 - d_1(1+p)$ | $1 - d/2$ | $d/2$ | $1 - d$ | $1 + dp/(1 - d(1+p))$ |
| L90 | $1 - d_2(1-p)/2$ | $d_2(1-p)/2$ | $1 - d_2(1-p)$ | | | | $1 - dp/(1 - d(1-p))$ |
| L45 (L135) | 1/2 | 1/2 | 0 | | | | $\infty$ |

As can be seen from this Table 1, even if actual p and d values are not referred to, the light intensity contrast ratio can be higher than one in the cases of L0 and L45 (L135). And if the polarization difference is used, the light intensity contrast ratio will ideally have a maximum value of $\infty$ at L45 (L135) (i.e., when the angle formed between the groove and the polarization plane of the polarized illuminating light is 45 degrees), will have a value of greater than one at L0 (i.e., when the groove and the polarization plane of the polarized illuminating light are parallel to each other), and will have a minimum value of less than one at L90 (i.e., when the groove and the polarization plane of the polarized illuminating light are perpendicular to each other). That is why supposing the grooves on the object's surface run at random and the polarization direction of the illuminating light varies discretely by 45 degrees each time, the light intensity contrast ratio will increase from one at a probability of 3/4(=75%). Still there is a chance that the contrast ratio decreases at a probability of 25%. However, the present inventors discovered and confirmed via experiments that when the object was irradiated with two different kinds of polarized illuminating light beams (i.e., 0 and 90 degree polarized light beams), image processing to detect the grooves to be described later was carried out in each of the two situations, and the results were averaged as an image, better results were obtained than in a situation where an ordinary light intensity image was detected. When two kinds of illuminating light beams (e.g., 45 and 135 degree illuminating light beams) are used, naturally good results should be obtained. For that reason, if the polarization difference is observed using two different kinds of polarized illuminating light beams, of which the polarization directions intersect with each other at right angles, then the plane and groove regions can be distinguished from each other at a very good contrast ratio. This is the principle of detecting a groove region according to the present disclosure.

Next, it will be considered how high the light intensity contrast ratio will be when the light intensity is observed by a conventional technique without using polarized light. In the following example, it will be considered what the light intensity contrast ratio between groove and plane regions will be when an ordinary non-polarized illuminating light source NP is used. In the groove region, supposing the azimuth angle of incidence is $\phi$ and the azimuth angle of emittance is $\theta$, if $\phi$ of the illuminating light is averaged with respect to the angles of observance for P and S, then the result will be ½. Thus, in the case of P, the following Equation (7) is satisfied:

$$L(NP)P(\theta)=\frac{1}{2}\times[(1-d_1)\cos^2\theta+d_1p\sin^2\theta]+\frac{1}{2}\times[(d_2p\sin^2\theta+(1-d_2)\sin^2\theta]+(1-p)(d_1+d_2)/4 \quad (7)$$

On the other hand, in the case of S, the following Equation (8) is satisfied:

$$L(NP)S(\theta+90°)=\frac{1}{2}\times[(1-d_1)\sin^2\theta+d_1p\cos^2\theta]+\frac{1}{2}\times[d_2p\cos^2\theta+(1-d_2)\cos^2\theta]+(1-p)(d_1+d_2)/4 \quad (8)$$

When the light intensity is observed, no analyzer is used, and therefore, P+S is observed. As for the plane region, on the other hand, there is no anisotropy in the first place, and therefore, Table 1 may be used as it is. Consequently, it can be seen that the light intensity contrast ratio will be calculated to be one as shown in the following Table 2 and the groove and plane regions cannot be distinguished from each other by their light intensities.

TABLE 2

| Groove-region | | Plane-region | | | |
|---|---|---|---|---|---|
| P ($\theta$) | S ($\theta$ + 90°) | P + S | P ($\theta$) + S ($\theta$ + 90°) | P + S | Contrast (Plane/Groove) |
| 1/2 × [(1 − $d_1$)cos$^2$ $\theta$ + $d_1$psin$^2$ $\theta$] + 1/2 × [($d_2$psin$^2$ $\theta$ + (1 − $d_2$) sin$^2$ $\theta$] + (1 − p)($d_1$ + $d_2$)/4 | 1/2 × [(1 − $d_1$)sin$^2$ $\theta$ + $d_1$pcos$^2$ $\theta$] + 1/2 × [$d_2$pcos$^2$ $\theta$ + (1 − d2) cos$^2$ $\theta$] + (1 − p)($d_1$ + $d_2$)/4 | 1 − d/2 | d/2 | 1 | 1 |

Comparing the results shown in Tables 1 and 2 to each other, as for the surface mucosa micro-geometric structure model that has been described with reference to FIG. 1, the principle of groove region enhancement processing may be summarized as follows:

(i) It is difficult to distinguish the groove and plane regions from each other by using a non-polarized illuminating light source and by observing their light intensities, because the light intensity contrast ratio will be too low in that case.

(ii) If the polarization difference value (//−⊥) is calculated using a polarized light source and a polarization image, then the light intensity contrast ratio between the groove and plane regions can be increased significantly.

(iii) But the light intensity contrast ratio depends on the angle formed in a plane between the incident illuminating light and the groove region, and becomes maximum when the angular difference is 45 degrees (L45), minimum when the angular difference is 90 degrees (L90) and an intermediate value when the angular difference is 0 degrees (L0).

(iv) In the processing of calculating a polarization difference value using two kinds of illuminating light beams, of which the polarization directions intersect with each other at right angles (i.e., different from each other by 90 degrees), and averaging it at last, good results are obtained when the groove regions need to be detected and none of them are missed.

Embodiments of the present disclosure will now be described.

Embodiment 1

Figure 6:
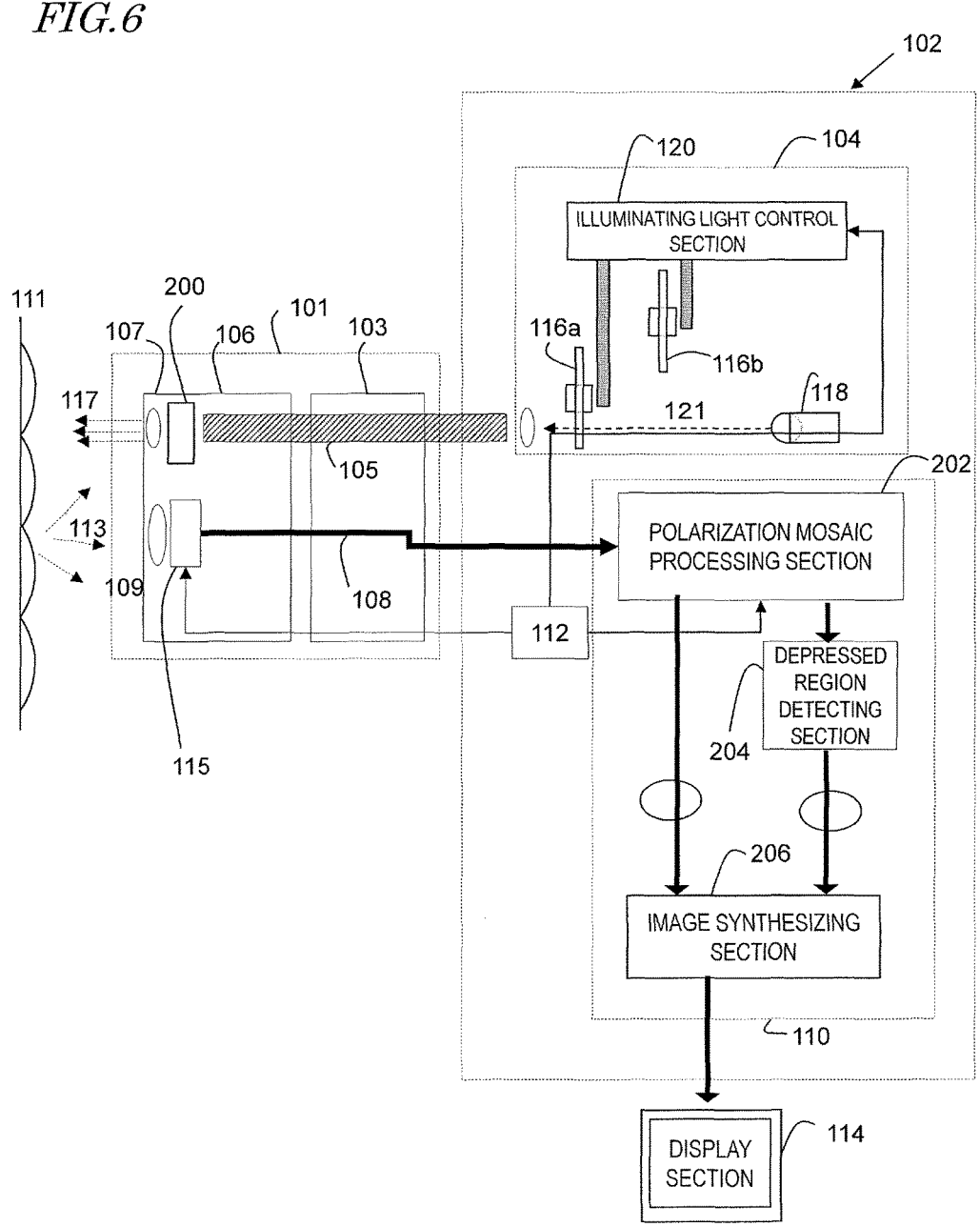
FIG. 6 is a block diagram illustrating a configuration for a first embodiment of the present disclosure.

FIG. 6 schematically illustrates an overall configuration for an image processing apparatus as a first embodiment of the present disclosure. This image processing apparatus includes an endoscope 101, a controller 102, and a display section 114.

The endoscope 101 includes a tip portion 106 with a monochrome broadband polarization image sensor 115 and an inserting portion 103 with a light guide 105 and a video signal line 108. The inserting portion 103 of the endoscope 101 has a structure that is elongated horizontally as shown in FIG. 6 and that can be bent flexibly. Even when bent, the light guide 105 can also propagate light.

The controller 102 includes a light source unit 104 and an image processor 110. A light source 118 such as a xenon light source, a halogen light source, an LED light source or a laser light source is built in the light source unit 104. The non-polarized light emitted from the light source 118 passes through a color wheel 116a, 116b with turning RGB filters. As a result, red (R), green (G) and blue (B) light beams are produced and then guided to the tip portion 106 through the light guide 105. When transmitted through an illuminating filter 200, each of these light beams turns into either a polarized light beam or a non-polarized light beam. Then, the light beam is further transmitted through an illuminating lens 107 and irradiates the surface of a viscera mucosa 111 that is the object as a polarized or non-polarized illuminating light beam 117. The light 113 reflected from the object is imaged onto the monochrome broadband polarization image sensor 115 through an objective lens 109.

Synchronously with the turn of the color wheel 106a, a synchronizer 112 sends a shooting start signal to the monochrome broadband polarization image sensor 115, thereby getting video based on the reflected light. The video signal thus obtained by capturing the image reaches an image processor 110 through the video signal line 108.

By performing these series of processing by the frame sequential method in which the colors are changed from one of RGB into another, a color image and a polarization image are captured. In the following description, a mode to capture a normal color image will be sometimes hereinafter referred to as either a "non-polarization image capturing mode" or a "normal image capturing mode", while a mode to capture a polarization image will be sometimes hereinafter referred to as a "polarization image capturing mode".

On receiving a signal indicating whether the endoscope should operate in the normal image capturing mode or the polarization image capturing mode from an external device, an illuminating light control section 120 inserts an associated color wheel into the optical path 121 of the illuminating light in response to that signal. In this manner, the spectral property of the illuminating light to irradiate the object frame-sequentially is changed.

If the signal indicates that the endoscope should operate in the normal image capturing mode, color images which have been processed by a polarization mosaic processing section 202 are synthesized together by an image synthesizing section 206 into a full-color moving picture, which is then presented as a movie, for example, on the display section 114. On the other hand, if the signal indicates that the endoscope should operate in the polarization image capturing mode, those images that have been processed by the polarization mosaic processing section 202 have their depressed region detected from their surface by a depressed region detecting section 204, have their color blue portions enhanced by the image synthesizing section 206 and then are presented as a movie, for example, on the display section.

Figure 7:
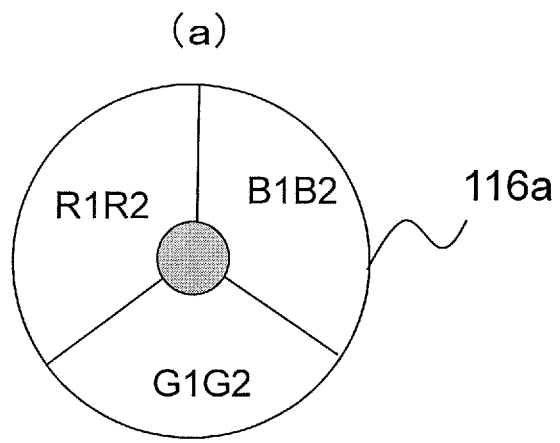
FIG. 7 illustrates color wheels for use in the first embodiment of the present disclosure.
Figure 7:
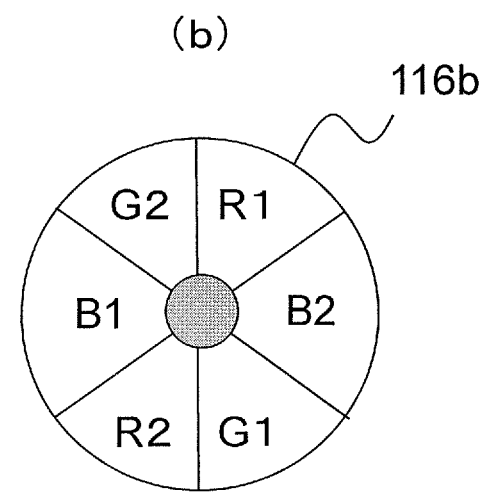

FIG. 7 illustrate examples of color wheels which may be used to filter an illuminating light beam. Potion (a) of FIG. 7 illustrates a color wheel 116a for use in the normal image capturing mode, which has three fan areas that are arranged around the axis of rotation. These three fan areas are comprised of a red filter which transmits light beams falling within substantially the same color red wavelength ranges R1R2 simultaneously, a green filter which transmits light beams falling within substantially the same color green wavelength ranges G1G2 simultaneously, and a blue filter which transmits light beams falling within substantially the same color blue wavelength ranges B1B2 simultaneously. In this case, R1 and R2 of R1R2 respectively indicate the shorter-wave half and the longer-wave half of the color red (R) wavelength range of 600 to 700 nm, for example. In the color filter 116a shown in portion (a) of FIG. 7, the fan area R1R2 can transmit both a light beam falling within the wavelength range R1 and a light beam falling within the wavelength range R2, and may be identified simply by "R". The same can be said about the other signs "G1G2" and "B1B2", too. In this description, the sign such as R1 is sometimes used to indicate a particular wavelength range and sometimes used to indicate a filter which selectively transmits a light beam falling within such a wavelength range.

A color wheel 116b for use in the polarization image capturing mode may have any of various configurations depending on in what wavelength range a polarization image is going to be captured. Portion (b) of FIG. 7 illustrates an exemplary color wheel 116b which sequentially transmits light beams falling within six different wavelength ranges. The color wheel 116b with such a configuration is suitably used to capture a full-color crossed Nicols image. It should be noted that either the color wheel 116a shown in portion (a) of FIG. 7 or the color wheel 116b shown in portion (b) of FIG. 7 is specified and selectively used in response to a signal supplied from an external device. More specifically, the color wheel 116a is used in the non-polarization image capturing mode or normal image capturing mode, and the color wheel 116b is used in the polarization image capturing mode.

Figure 8:
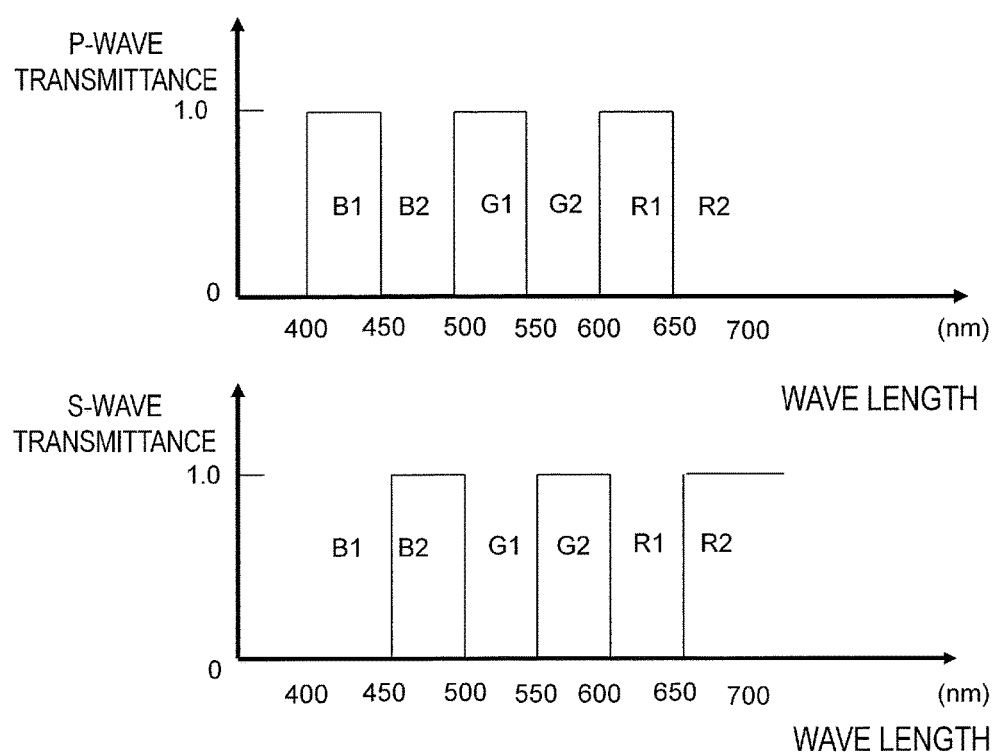
FIG. 8 shows the characteristic of an illuminating filter according to the first embodiment of the present disclosure.

FIG. 8 shows the transmission characteristic of the illuminating filter 200. This filter has a comb transmission characteristic in which P- and S-polarized light beams are transmitted alternately in the respective visible light wavelength ranges of B, G and R. For instance, in the example illustrated in FIG. 8, only a P-polarized light beam is transmitted in the wavelength range B1 (of 400 to 450 nm), and only an S-polarized light beam is transmitted in the wavelength range B2 (of 450 to 500 nm). That is why if the wavelength of the incoming light that has come from the light source through the light guide falls within the wavelength range B1, that incoming light is transformed by the illuminating filter 200 into a P-polarized illuminating light beam. Likewise, if the wavelength of the incoming light that has come from the light source through the light guide falls within the wavelength range B2, that incoming light is transformed by the illuminating filter 200 into an S-polarized illuminating light beam. It should be noted that if the wavelength of the incoming light that has come from the light source through the light guide covers the entire wavelength range B1B2 in the normal image capturing mode, then P- and S-polarized light beams are mixed together, and therefore, a non-polarized illuminating light beam is obtained.

A filter having the characteristic shown in FIG. 8 may be implemented as a multilayer film polarizer as disclosed in Laid-Open Patent Publication No. 2009-210780, for example.

Figure 9:
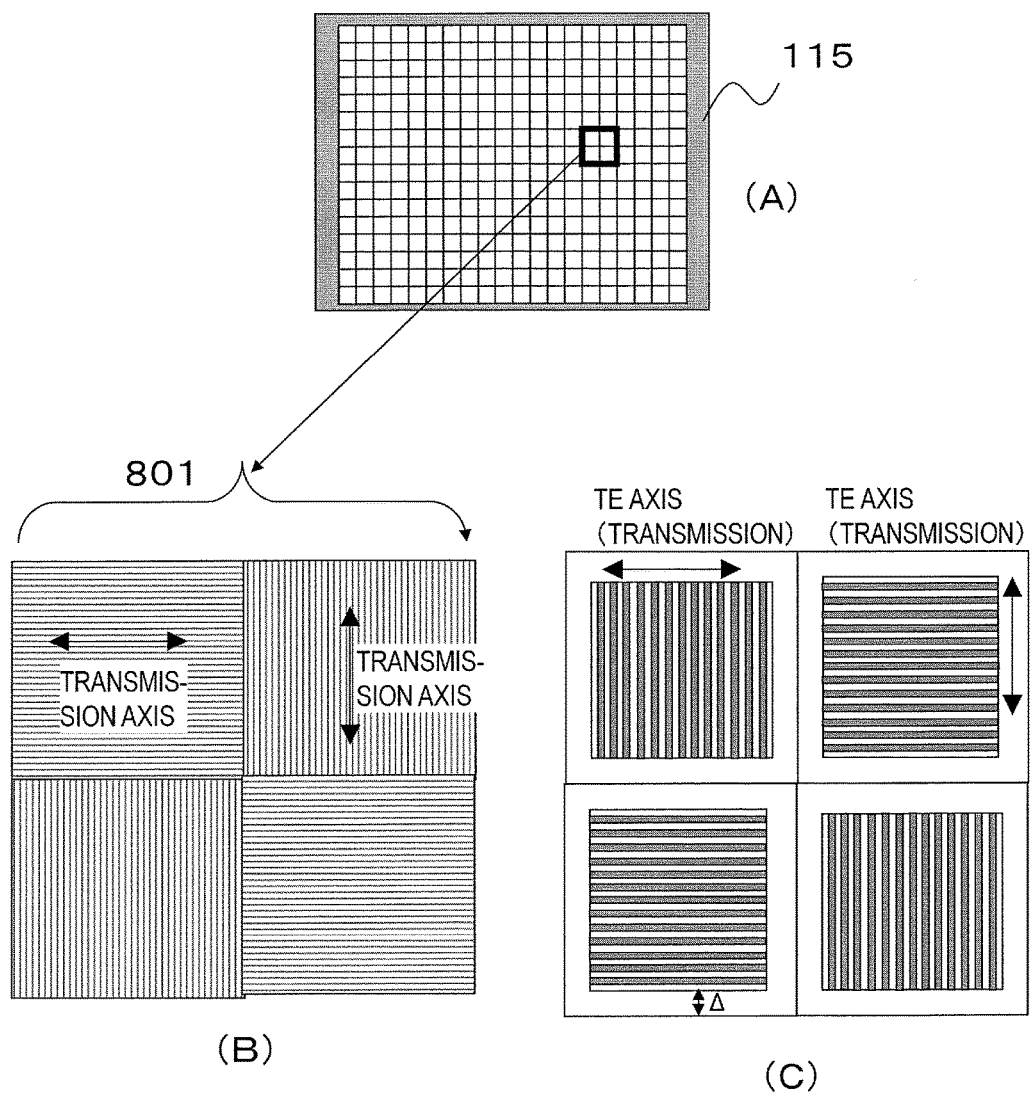
FIG. 9 illustrates the planar structure and transmission axis directions of wire grids which form a monochrome broadband polarization image sensor according to the first embodiment of the present disclosure.

FIG. 9 schematically illustrates an exemplary structure for a patterned polarizer (which is either a polarization mosaic or a polarization mosaic array) on the image capturing plane of the monochrome broadband polarization image sensor 115. As shown in portion (A) of FIG. 9, pixels are arranged regularly in columns and rows (i.e., in the X-Y directions) on the image capturing plane.

Since this image sensor 115 is used in the frame sequential method in which the colors of the illuminating light are changed sequentially from one of RGB into another, no color mosaic filters are arranged on the image capturing plane. That is why the image sensor 115 itself is a monochrome image sensor, and the polarizer is arranged in each pixel. Since light beams falling within visible light wavelength ranges are sequentially incident on the respective pixels, the polarization selection characteristic of the polarizers for use in this embodiment is realized within the visible light wavelength range. Specifically, in the wavelength range of 400 nm to 800 nm, the extinction ratio indicating the polarized light obtaining ability of the polarizers of this embodiment is 100 to 1 or more. For that reason, in this embodiment, polarizers which exhibit polarization properties only at particular wavelengths that form only a narrow part of the visible light wavelength range are not used, but metallic wire grid polarizers which can exhibit high polarized light obtaining ability in a broad wavelength range are adopted instead.

Portion (B) of FIG. 9 illustrates a single unit of the polarization filter which is associated with four pixels that are arranged in two rows and two columns (and which will be sometimes hereinafter referred to as a "2×2 block"). In this single unit, four polarization filters are arranged by rotating each of these polarization filters 90 degrees within the plane from the adjacent one. In portion (B) of FIG. 9, the axial direction indicated on each polarization filter is set to be its polarization transmission axis.

Portion (C) of FIG. 9 illustrates an exemplary arrangement of wires in a situation where the polarization filters are implemented as metallic wire grids to have the arrangement shown in portion (B) of FIG. 9. In general, in a wire grid, the direction that intersects at right angles with the direction in which metallic wires run (and which will be hereinafter referred to as a "TE axis") defines the polarization transmission axis. That is why if those wires are represented by straight lines in a schematic representation, then each of the polarization transmission axis directions shown in portion (B) of FIG. 9 is different by 90 degrees from the direction in which an associated set of metallic wires runs in portion (C) of FIG. 9. Thus, to avoid such confusion, when indicating the transmission axis directions of polarization filters for use in an embodiment of the present disclosure, the transmission axes shown in portion (B) of FIG. 9 will always be used and a plan view illustrating directly the directions in which the wires of the wire grids actually run will not be used.

As will be described later, the arrangement plane of these metallic wire grids may be located at any of various levels from the top through the bottom of the image sensor. In a plan view, these wire grids are arranged in respective inner parts of their areas with some margin Δ left with respect to the outer periphery of the pixel unit regions to avoid interference with other pixels. If a single pixel region is a square, of which each side has a length D of 3 to 4 μm, the margin Δ may be set to be equal to or greater than 0.2 μm (=200 nm), for example. A tradeoff is inevitable between the transmittance, the extinction ratio and the duty ratio of the width L of each of multiple metallic wires that form these wire grids to their spacing S. In an embodiment of the present disclosure, the width L and spacing S are supposed to be equal to each other. If L=S=0.1 μm=100 nm as will be described later, and if Δ=0.2 μm=200 μm is satisfied and if the directions in which the metallic wires run define angles of 0 and 90 degrees with respect to either the vertical axis or the horizontal axis within the image capturing plane, the number of the metallic wires that form each of these wire grids is 17.

An exemplary conventional polarization image sensor which was actually made using wire grid polarizers of aluminum and which had its performance evaluated in term of the extinction ratio is disclosed in "CCD Polarization Imaging Sensor with Aluminum Nanowire Optical Filters", 30 Aug. 2010/Vol. 18, No. 18/OPTICS EXPRESS pp. 19087-19094. According to this article, very small wire grid polarizers which were arranged at a pitch P of 140 nm and with a height H of 70 nm within a pixel region with a size of 7.4 μm square had extinction ratios of about 30 to 1, about 45 to 1, and about 60 to 1 at wavelengths of 450 nm, 580 nm and 700 nm, respectively. These results of the actual example reveal that it would be difficult to achieve an extinction ratio of 100 to 1 even if wire grid polarizers of a significantly reduced size were introduced into an image sensor. That is why according to this embodiment, a structure for achieving a high extinction ratio by stacking two wire grid layers one upon the other is adopted instead.

Figure 10:
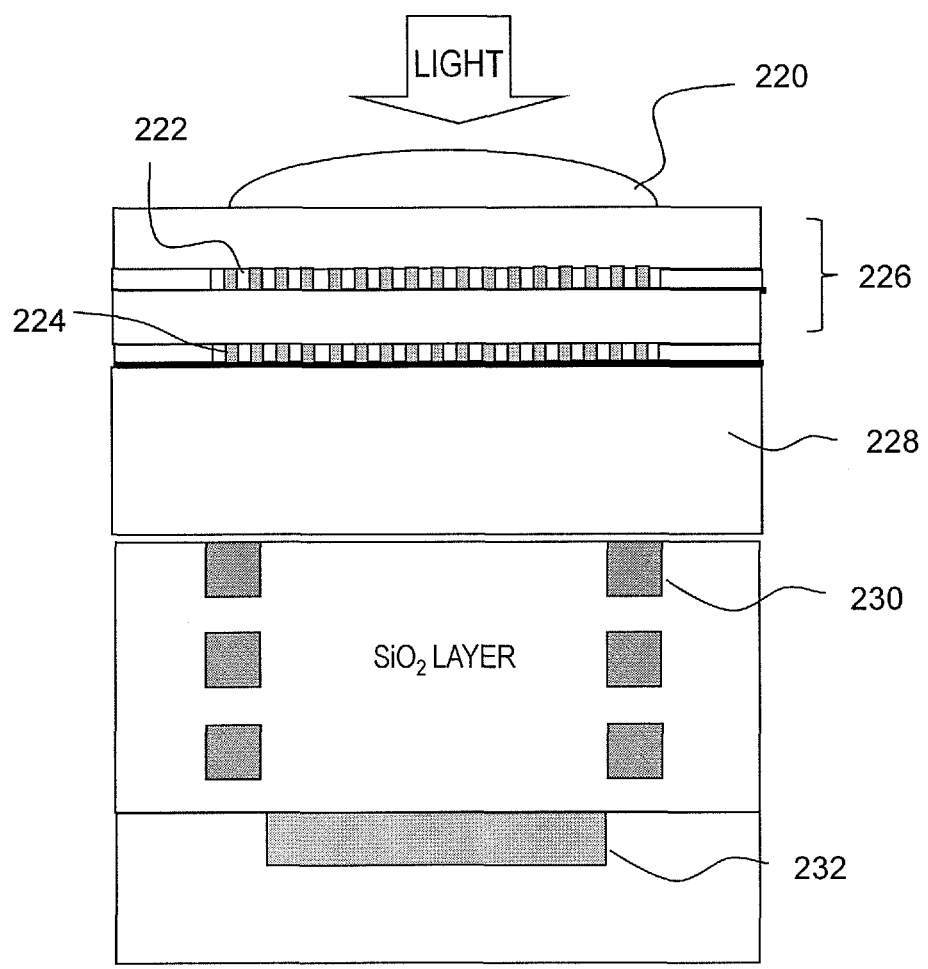
FIG. 10 illustrates a cross-sectional structure of a monochrome broadband polarization image sensor according to the first embodiment of the present disclosure.

Next, an exemplary cross-sectional structure for the image sensor 115 will be described with reference to FIG. 10.

The incoming light reaches the image capturing plane through an objective lens 109 which is arranged over the image sensor 115. In this image sensor 115, the incoming light sequentially reaches its members in the following order. First of all, a micro lens 220 is arranged on the top surface. In this case, the micro lens 220 plays the role of condensing the incoming light efficiently onto the PD (photodiode) 232 but also refracts the optical path of an obliquely incident light beam so that its angle of incidence is almost 90 degrees with respect to the image capturing plane. That is why the micro lens 220 can be used particularly effectively when shooting is often carried out at a wide angle as in an endoscope, for example. In addition, the micro lens 220 can make light incident onto the wire grid layers 222, 224 from substantially right over them, and therefore, can also check the decrease in TM transmittance and extinction ratio. Under the micro lens 220, arranged is a planarizing layer 226, under which the first wire grid layer 222 is arranged to transmit only polarized light beams that are polarized in particular directions (of which the plane of polarization is rotated 90 degrees apiece within the image capturing plane) and to reflect or absorb the other light beams.

In this embodiment, the first wire grid layer 222 has a hollow structure which is defined by the gaps between the metallic wires. Since these metallic wires can keep contact with the air, a decrease in extinction ratio can be avoided effectively.

Under the first wire grid layer 222, arranged is the second wire grid layer 224, which has basically the same arrangement directions, same size, and same hollow structure, and is made of the same material, as the first wire grid layer 222.

By using this stack of the first and second wire grid layers 222 and 224, even if each of these grids is a fine-line wire grid that has had its extinction ratio decreased to about 10 to 1, the overall extinction ratio of these two layers can be increased to approximately 100 to 1. Under the second wire grid layer 224, arranged in this order are a planarizing layer 228 and an interconnection layer 230. In this case, since no interconnects 230 are arranged in the region that should transmit the incoming light, the incoming light can reach the underlying PDs (photodiodes) 232 without being cut by any of those interconnects 230. In the image capturing plane, a lot of PDs 232 are arranged in columns and rows to form a photosensitive cell array.

In general, in an image sensor, it is important to shorten the distance from the micro lens 220 to the PD 232 as much as possible and reduce its overall height. The same can be said about a polarization image sensor according to this embodiment. That is to say, if the distance from the micro lens 220 to the PD 232 is too long, a crosstalk will be produced between pixels to deteriorate the polarization property (e.g., cause a decrease in extinction ratio, in particular). According to this embodiment, the distance from the wire grids to the PD is set to be approximately 2 to 3 μm in order to reduce the overall height. Also, the wire grid polarizer reflects a TE wave, of which the polarization direction intersects at right angles with that of a TM wave to be transmitted, and the reflected TE wave becomes stray light to cause deterioration in performance. Thus, to avoid such a situation, it is effective to form the wire grids 222, 224 as a stack of multiple layers, not a single layer, so that the reflected light is absorbed into those layers stacked.

Now, it will be described how the image processing apparatus of this embodiment performs an image capturing operation.

First of all, it will be described with reference to FIGS. 11A and 11B how the image processing apparatus of this embodiment operates in a normal image capturing mode.

Figure 11A:
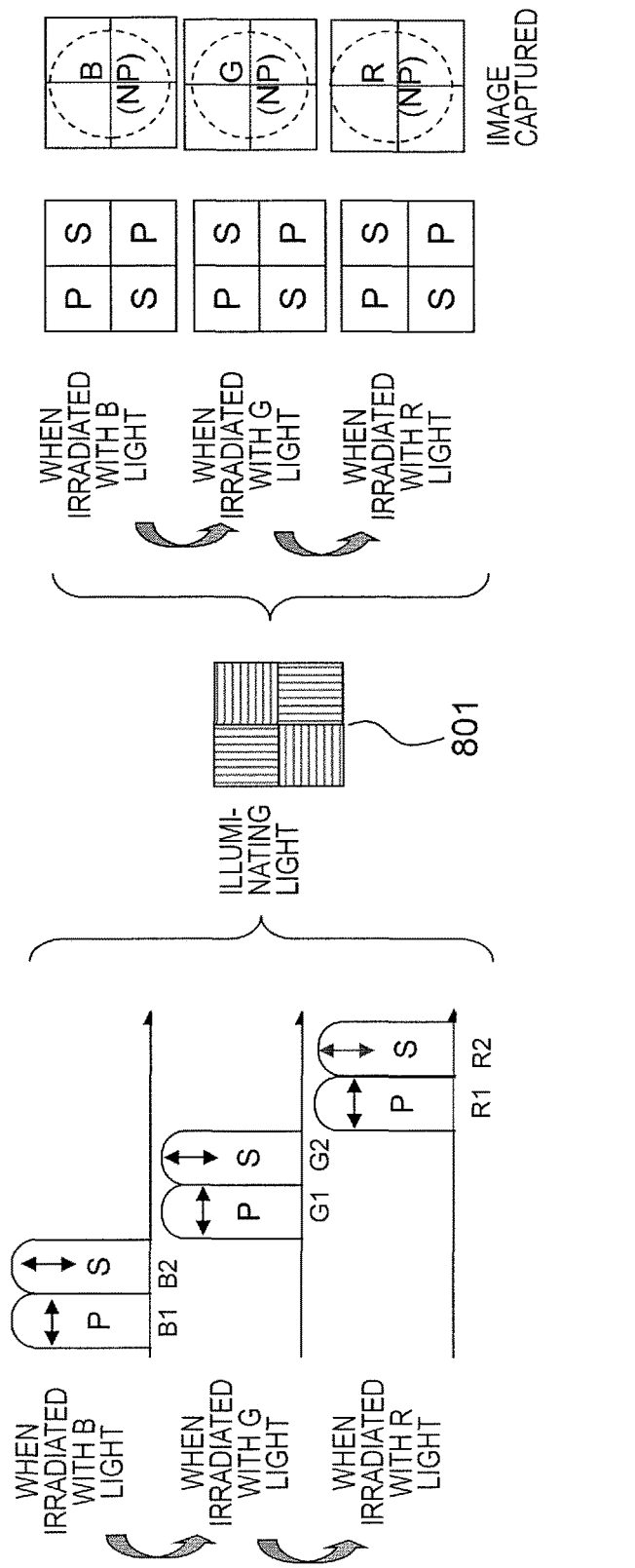
FIG. 11A illustrates how the image processing apparatus according to the first embodiment of the present disclosure operates in a normal image capturing mode.
Figure 11B:
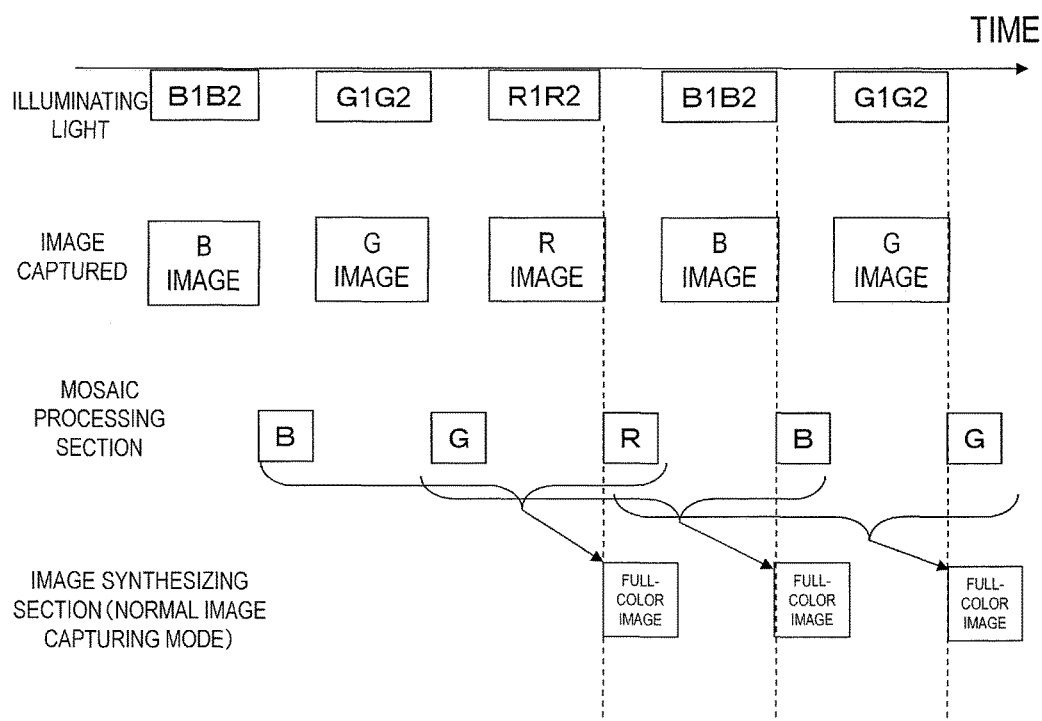
FIG. 11B is a timing chart showing how the apparatus according to the first embodiment of the present disclosure operates in the normal image capturing mode.

FIG. 11A illustrates how to perform an image capturing operation using respective illuminating light beams in a normal image capturing mode, and FIG. 11B is a timing chart showing the sequence of the image capturing operations. Specifically, the optical spectrum of a frame sequential illumination source is shown on the left-hand side of FIG. 11A. Strictly speaking, a color B illuminating light beam is a mixture of two polarized light beams representing mutually different colors and having mutually different polarization directions (i.e., B1 (P-polarized) and B2 (S-polarized) light beams). The same can be said about the other colors G and R illuminating light beams. When radiated, these illuminating light beams can be regarded as B, G and R non-polarized light beams, respectively. That is why this frame sequential illumination source becomes virtually no different from a known one.

When the object is irradiated with an illuminating light beam, the returning light beam that has been reflected from the object is observed by the monochrome broadband polarization image sensor 105. In FIG. 11A, shown is only a fundamental unit 801 of the polarization mosaic that the polarization image sensor 105 has. Among the four polarizers included in this fundamental unit 801, the two polarizers that are located at the upper left and lower right corners (i.e., P polarization filters) transmit a P-polarized light beam which is polarized horizontally within the image capturing plane. On the other hand, the two polarizers that are located at the upper right and lower left corners (i.e., S polarization filters) transmit an S-polarized light beam which is polarized vertically within the image capturing plane.

The monochrome broadband polarization image sensor 115 performs a polarization operation in the wavelength range of 400 nm to 800 nm, which corresponds to the entire visible light wavelength range. That is why no matter which of the color B, G and R illuminating light beams the object is irradiated with, only a single image sensor can deal with the polarization operation.

The captured image is obtained by getting the light beam that has returned from the object being irradiated with a non-polarized illuminating light beam received via either a P-polarization filter or an S-polarization filter. That is why by averaging the pixel values obtained in a 2×2 pixel region (i.e., consisting of four pixels), a non-polarization image can be obtained. The averaged pixel value is virtually located at the center of the 2×2 (i.e., four) pixels. Thus, on the right-hand side of FIG. 11A, each of the pixel regions indicated by the dotted circles says NP (non-polarization). By shifting the 2×2 (i.e., four) pixels on a pixel-by-pixel basis, the resolution will not decrease substantially.

In this manner, non-polarization images can be captured under the frame sequential non-polarized B, G and R illuminating light beams. By sequentially storing the images in the three primary colors in color image buffer memories and by synthesizing these images together when three-primary-color images are obtained, a full-color moving picture can be generated. This processing will be hereinafter referred to as "polarization mosaic pixel averaging processing", which is carried out by the polarization mosaic processing section 202 shown in FIG. 6. On the other hand, a full-color moving picture is generated by the image synthesizing section 206.

FIG. 11B is a timing chart showing the sequence of these operations. Specifically, the operation of emitting illuminating light beams, the image capturing operation, and the color component images processed by the polarization mosaic processing section 202 are shown in this order from top to bottom of FIG. 11B. The respective operations are performed at these timings by making the synchronizer 112 control the illuminating light control section 120, the monochrome broadband polarization image sensor 115 and the polarization mosaic processing section 202.

Next, it will be described with reference to FIGS. 12 and 13 how the image processing apparatus of this embodiment operates in the polarization image capturing mode.

Figure 12:
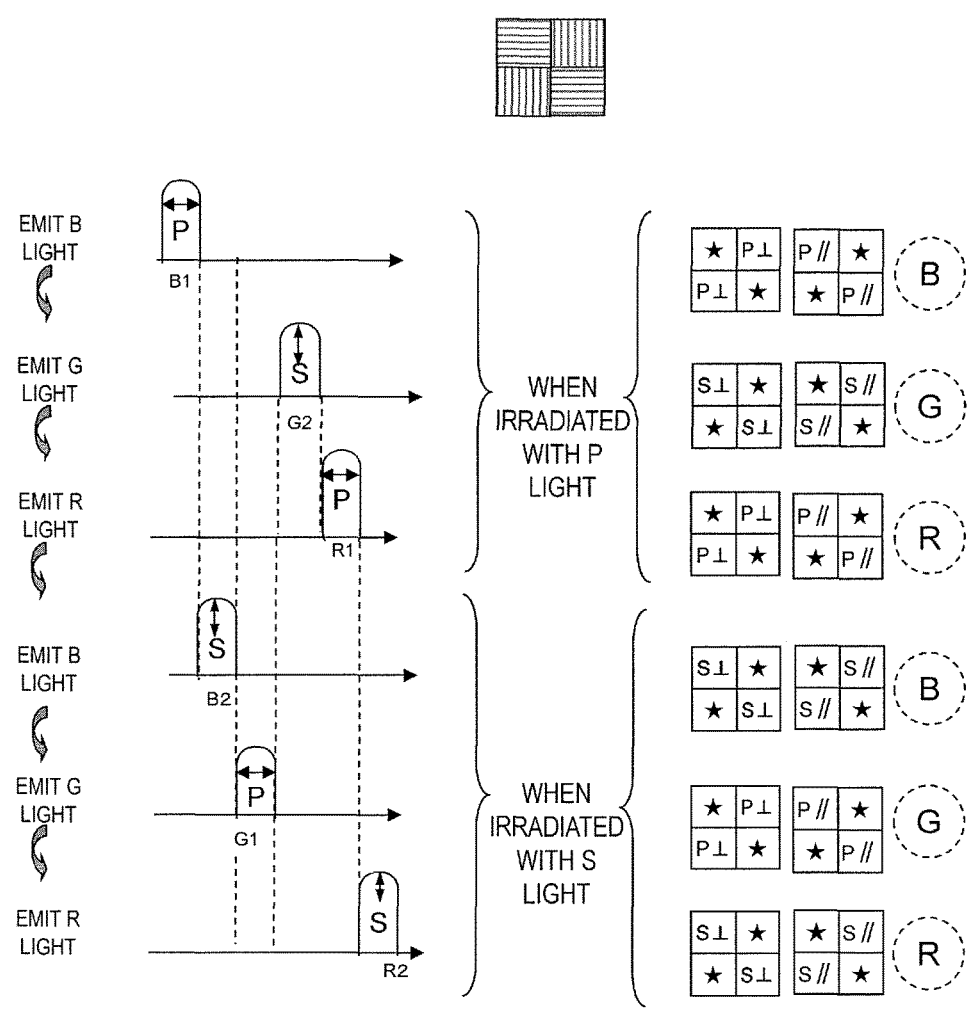
FIG. 12 illustrates how a polarization mosaic processing section 202 operates in a polarization image capturing mode according to the first embodiment of the present disclosure.
Figure 13:
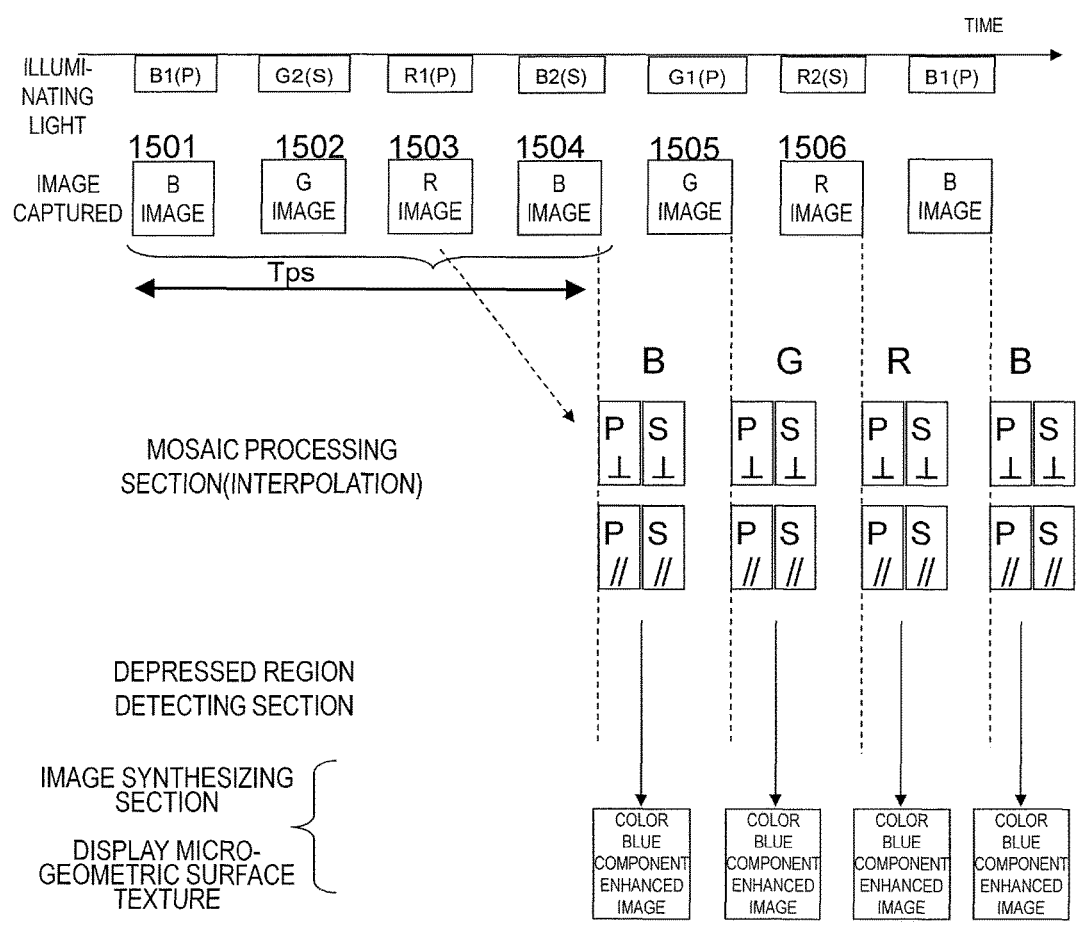
FIG. 13 is a timing chart showing how the apparatus according to the first embodiment of the present disclosure operates in the polarization image capturing mode.

FIG. 12 illustrates generally how to perform an image capturing operation using respective illuminating light beams in the polarization image capturing mode when the polarization image capturing color wheel shown in portion (b) of FIG. 7 is used, and FIG. 13 is a timing chart showing the sequence of the image capturing operations. In this example, BGR frame sequential color illuminating light beams are used. Such an image capturing technique is applicable particularly effectively to a situation where the surface of a mucosa needs to be observed with the naked eye with specular reflection eliminated. This technique can also be used effectively when the polarization property inside an organism's mucosa should be observed within a narrow wavelength range.

By turning the polarization image capturing color wheel shown in portion (b) of FIG. 7, the object is sequentially irradiated with B1, G1 and R1 which are P-polarized light beams and B2, G2 and R2 which are S-polarized light beams. The returning light beam that has been reflected from the object is observed by the monochrome broadband polarization image sensor 105. And at the fundamental unit 801 of the polarization mosaic, multiple different components are captured. The image thus captured becomes image information comprised of twelve different components that are crossed-Nicols (P⊥) and parallel-Nicols (P//) RGB full-color components under a P-polarized illuminating light beam and crossed-Nicols (S⊥) and parallel-Nicols (S//) components falling within the RGB wavelength ranges under an S-polarized illuminating light beam. In this case, since some portions of the pixel information are also missing, pixel values indicated by the solid star ★ need to be obtained by making interpolation using the values of the surrounding pixels. By adopting such a configuration, when the object is observed in real time through an endoscope, the state of the mucosa can be observed easily with specular reflected components removed from the surface of the mucosa. In this example, in order to reproduce a moving picture quickly, the filters on the circumference of the wheel are arranged in the order of B1-G2-R1-B2-G1-R2, thereby making the colors RGB and P- and S-polarizations alternate with each other.

FIG. 13 is a timing chart showing the sequence of these operations. Specifically, the operation of emitting illuminating light beams, the image capturing operation, and the color component images processed by the mosaic processing section are shown in this order from top to bottom of FIG. 13. The respective operations are performed at these timings under the control of the synchronizer 112. When the object is alternately irradiated with a P-polarized light beam and an S-polarized light beam, their corresponding crossed-Nicols images (P⊥) (S⊥) and parallel-Nicols images (P//) (S//) are output. However, to obtain crossed-Nicols (P⊥) or (S⊥) RGB full-color images, it takes a period of time Tps in which the object is irradiated with B, G and R frame sequential light beams with the polarized illuminating light sources fixed. That is why no moving picture can be displayed during this period of time. The reason is that polarized illuminating light beams and color illuminating light beams are both radiated frame sequentially, and therefore, it takes some time to get every kind of illuminating light beam radiated. In detecting a depressed region through an endoscope, however, the operation does not have to be performed in real time, and there is no problem.

Figure 14:
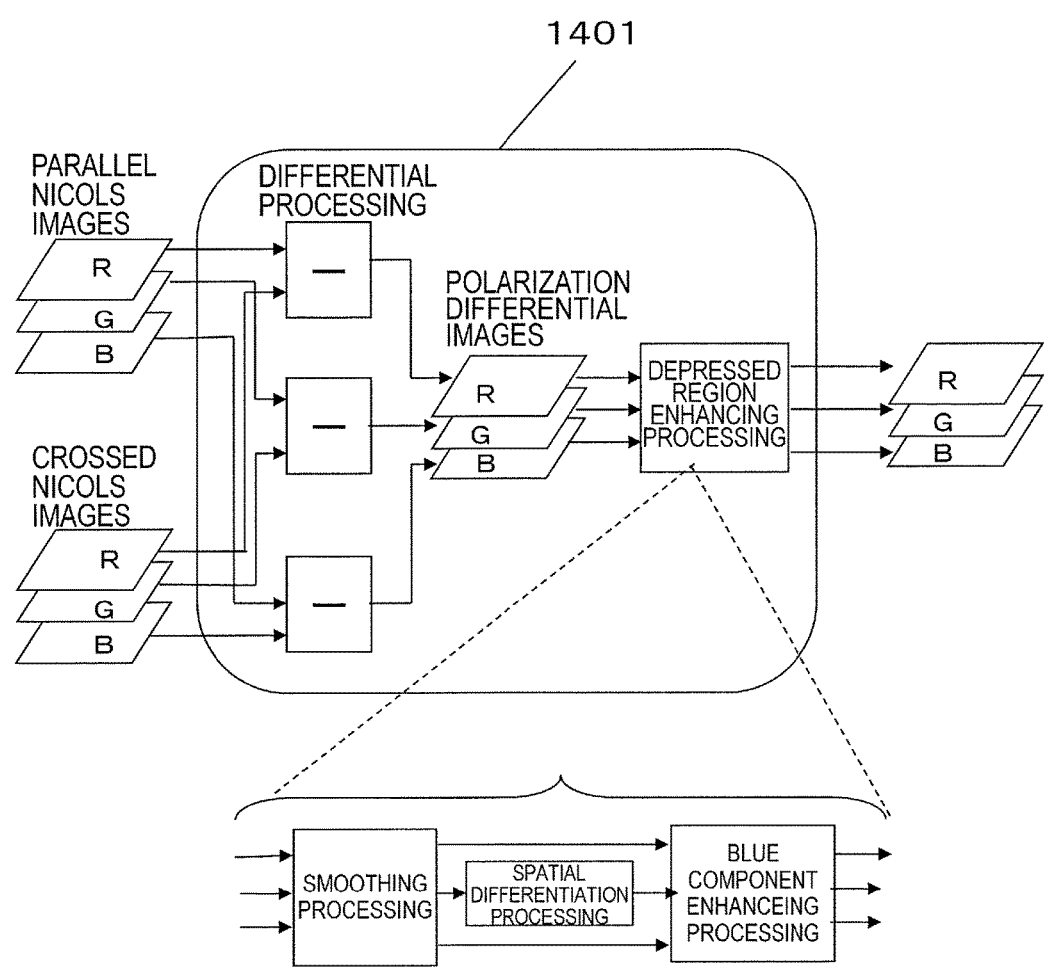
FIG. 14 is a block diagram illustrating how a depressed region detecting section 204 and an image synthesizing section 206 perform their processing in the first embodiment of the present disclosure.

FIG. 14 illustrates how the depressed region detecting section 204 and the image synthesizing section 206 perform the polarization image enhancing processing 1401.

In the following description, the sequence of getting four kinds of images that are crossed-Nicols images (P⊥) (S⊥) and parallel-Nicols images (P//) (S//) on a frame-by-frame basis for each of B, G and R components as already described with reference to FIGS. 12 and 13 will be described on the supposition that those four kinds of parallel and crossed Nicols images are obtained simultaneously in RGB full colors. The parallel Nicols and crossed Nicols images comprised of R, G and B components are subjected to the differential processing and depressed region enhancing processing shown in FIG. 14. In this case, the depressed region enhancing processing is carried out in the order of smoothing processing, spatial differentiation processing and blue component enhancing processing.

(1) Differential Processing

By calculating [(Parallel Nicols image pixel value)−(Crossed Nicols image pixel value)] on a pixel-by-pixel basis for each of the R, G and B components, polarization differential images are generated. Since two pairs of parallel and crossed Nicols images can be generated by rotating the polarization direction of an illuminating light beam L 90 degrees as will be described later, this processing is carried out on each of the two pairs. Also, in this case, even if the polarization differential images are replaced with degree of polarization images to be obtained by dividing the polarization differential images by (Parallel Nicols image pixel value)+(Crossed Nicols image pixel value), substantially the same effect can be achieved.

(2) Smoothing Processing

Figure 15:
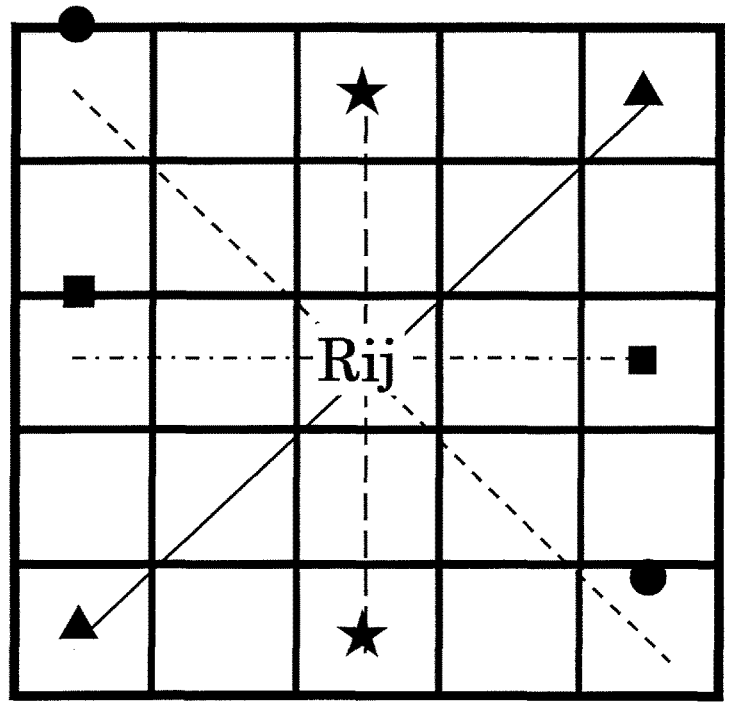
FIG. 15 illustrates an exemplary smoothing filter and an exemplary differentiation processing mask for use in the depressed region detecting section 204.

Before being subjected to the differentiation processing on the next stage, the input image has its noise components, of which the frequencies are higher than the frequency of the texture to be enhanced, removed. Specifically, to remove such noise components, smoothing filter processing is carried out. In this embodiment, a general Gaussian filter is used for that purpose. If the mask size of the filter is set to be the same as the mask size of a differentiation mask filter to be described later, it is possible to avoid enhancing fine granular noise. Portion (A) of FIG. 15 illustrates an example of a smoothing filter with a size of 5×5. For example, an image of 1024×768 pixels may have its size reduced to 512×384 pixels using this smoothing filter.

(3) Differentiation Processing

The G component image that has gone through the smoothing filter processing is subjected to the following differentiation mask processing to detect a pixel region which is darker than the surrounding regions. Such a pixel region that is darker than the surrounding regions needs to be detected because if the polarization direction of the polarized illuminating light beam defines an angular difference of around 0 to 45 degrees with respect to a surface groove of the object, the light intensity contrast ratio increases and the region becomes darker than the surrounding regions as already described with reference to Table 1. In performing this differentiation processing, a differentiation filter which specifies a center pixel and surrounding pixels as shown in Portion (B) of FIG. 15 (and which is comprised of 5×5 pixels in this example) is set for the image that has gone through the smoothing processing. There are various kinds of differentiation filters. In this example, a differentiation filter which is suitable for enhancing the net of grooves running on the surface continuously is selected. The following processing is carried out on a 5×5 pixel region:

(i) The value of the center pixel $R_{ij}$ is compared to those of two surrounding pixels that are adjacent to the center pixel $R_{ij}$ horizontally (as indicated by the solid squares ■), vertically (as indicated by the solid stars ★), obliquely upper rightward (as indicated by the solid triangles ▲) and obliquely lower rightward (as indicated by the solid circles ●).

(ii) If the value of the center pixel turns out to be larger than those of the two surrounding pixels in any of these four directions, the decision is made that the center pixel is depressed.

(iii) The absolute value of the maximum difference in those four directions is supposed to be Δ and the product of Δ and a certain constant is supposed to be ΔC, which is regarded as the result of the spatial differentiation processing.

(4) Color Blue Component Enhancement

By subtracting the ΔC value from R and G components, the color blue component is enhanced. In this case, if the R and G components become equal to or smaller than zero, then continuity is maintained by subtracting the deficit from other color components. That is why the hue changes according to the magnitude of Δ but smooth connection can still be made. Supposing one of the R and G components that has the smaller value is C1 and the other having the larger value is C2, the situations are classified into the following three cases.

Figure 16:
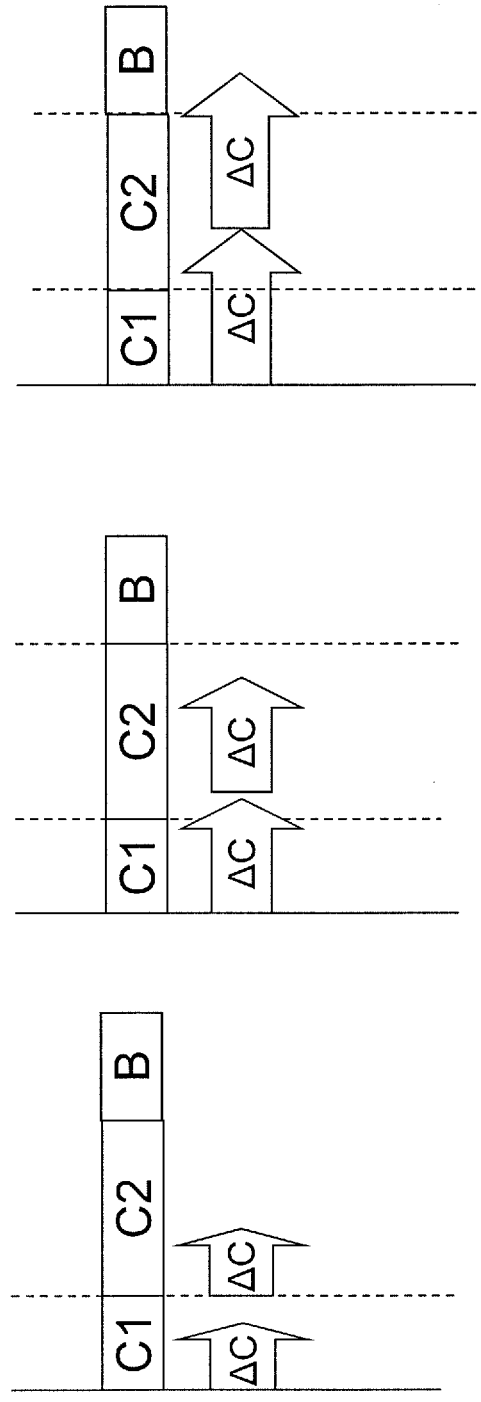
FIG. 16 shows how the depressed region detecting section 204 performs color blue enhancing processing.

FIG. 16 shows the following three cases.

First of all, 1) if ΔC is equal to or smaller than C1, then the processing of subtracting ΔC from the R and G signals is carried out. Next, 2) if ΔC is a value that is greater than C1, then the smallest signal becomes equal to zero and the other signals are subtracted from an intermediate signal. Next, 3) if the result of the subtraction from the R and G signals becomes equal to zero, then the other signal is subtracted from the B signal.

By performing these processing steps, a color signal in a pixel region in which the center pixel is brighter than the surrounding pixels has its color blue component enhanced according to its degree, thus generating a color image similar to the one obtained by sprinkling an indigo carmine solution.

1) If $\Delta C \leq C1$ then $C1 = C1 - \Delta C$, and $C2 = C2 - \Delta C;$

2) If $C1 < \Delta C \leq (C1+C2)/2$, then $C1 = 0$, and $C2 = (C1+C2) - (2\Delta C);$ and 3) If $(C1+C2)/2 < (\Delta C)$, then $C1 = 0$ $C2 = 0$, and $$B = B - ((2\Delta C) - C1 - C2) \qquad (9)$$

As can be seen from Table 1, the surface groove detection accuracy depends on the angle of the polarization plane of the illuminating light. In general, it is impossible to obtain this information in advance. For that reason, the processing of inputting parallel Nicols and crossed Nicols images that has already been described with reference to FIG. 14 may be carried out on another pair of parallel and crossed Nicols images, for which the polarization direction of the polarized illuminating light has been changed by 90 degrees. This is not indispensable processing for the present invention but the present inventors confirmed its effectiveness via experiments.

Figure 17A:
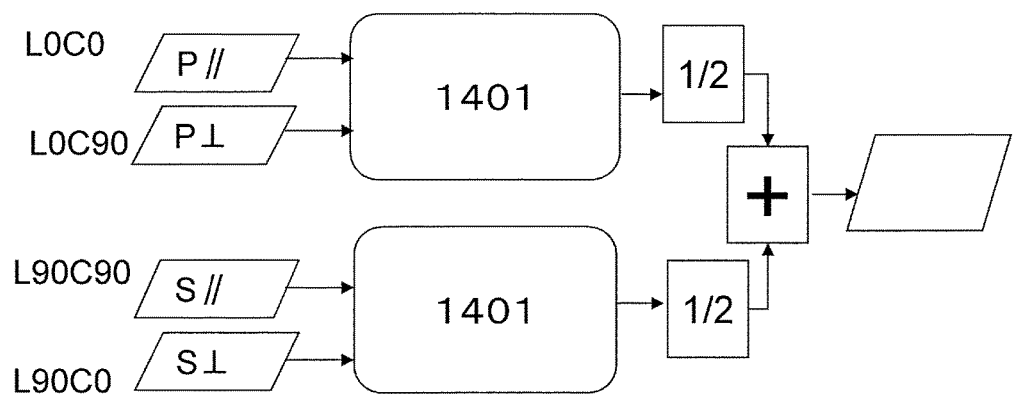
FIG. 17A illustrates the processing of synthesizing together two pairs of parallel and crossed Nicols images for use in the depressed region detecting section 204.

FIG. 17A illustrates this processing. The results of processing that has been performed in response to input of two images L0C0 (P//) and L0C90 (P⊥) that are parallel and crossed Nicols images under P-polarized illuminating light are obtained. The results of processing that has been performed in response to input of two images L90C0 (S//) and L90C90 (S⊥) that are parallel and crossed Nicols images under S-polarized illuminating light are obtained. And those results are added together and their average is calculated, thereby obtaining an image as a final result. If the direction in which the surface groove runs is substantially parallel to the polarization direction of the incident polarized light (i.e., in the case of L90 in Table 1), then the contrast ratio will decrease significantly. However, according to this processing, such a problem can be relieved by the effect achieved in the case of L0 (i.e., by using illuminating light that is the other of the pair and that crosses the former illuminating light at right angles). The present inventors discovered and confirmed via experiments that the performance could be recovered to somewhere between the ones achieved in the cases of L0 and L90 as a result of this processing. On top of that, since the blue component enhanced image described above is generated based on somewhat different information and then added, the amount of information increases, and the color blue component will have a larger number of grayscale levels in final enhanced image. As a result, an image which is even more similar to an indigo carmine sprinkled image can be obtained as well.

Figure 17B:
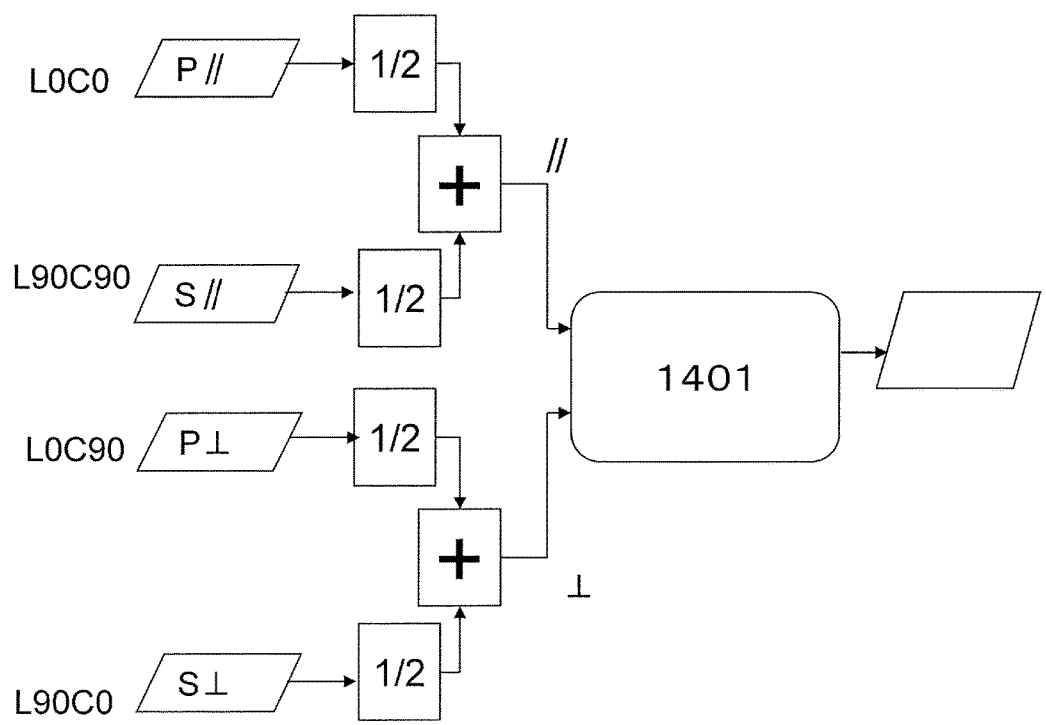
FIG. 17B illustrates the processing of synthesizing together two pairs of parallel and crossed Nicols images for use in the depressed region detecting section 204.

Alternatively, such image processing and adding and averaging processing may be carried out as two pairs on a different combination of four polarization images. For example, the processing described above may be carried out on L0C0 (P//) and L90C0 (P⊥), while the processing described above is being carried out on L0C90 (S⊥) and L90C90 (S//) in parallel. And finally the results of these two lines of processing may be added together and their average may be calculated. Optionally, it may also be determined, before the processing of detecting a depressed groove, where to add the results together and calculate their average. For example, as shown in FIG. 17B, parallel Nicols (//) and crossed Nicols (⊥) images in which two different kinds of polarized illuminating light beams are averaged may be generated in advance by the adding and averaging processing. And that pair of images may be entered into the polarization image enhancing processing 1401. In this manner, the difference in image quality resulting from the anisotropy of the polarization plane of the illuminating light can be averaged. The present inventors discovered that this processing could reduce the noise of the final enhanced image more effectively than averaging the result itself of the processing on the depressed groove.

Still alternatively, if the directivity of the surface grooves is known in advance, the object may be either irradiated with effective illuminating light with its polarization plane determined or irradiated with two kinds of illuminating light beams that cross each other at right angles, and then image processing may be carried out using only particular parallel and crossed Nicols images to detect and enhance the depressed portion. For example, as can be seen from the results shown in Table 1, it is most effective to irradiate linearly polarized light, of which the polarization plane defines an angle of 45 degrees with respect to the direction in which the grooves run. That is why the results of processing in a situation where two images L0C0 (P//) and L0C90 (P⊥) which are parallel and crossed Nicols images under P polarized illuminating light have been input and the results of processing in a situation where two images L90C0 (S//) and L90C90 (S⊥) which are parallel and crossed Nicols images under S polarized illuminating light have been input may be obtained respectively. Either the P-illuminating light or the S-illuminating light may be selected if the irradiation direction of the illuminating light is closer to the best irradiation direction. And its associated result of the processing may be used to detect the groove or used as an enhanced image. Examples of such a special case scenario include a situation where the large bowel mucosa needs to be observed through an endoscope. In the large bowel of a human being, the depressed grooves on the surface mucosa often run in the circumferential direction of the enteric canal inside the large bowel and have anisotropy. In such a situation, while looking at either a color light intensity image of the enteric canal or an enhanced image of the grooves displayed on the monitor, the physician with the endoscope can select the results of the most effective processing to be obtained by irradiating the enteric canal with linearly polarized light at an angle of nearly 45 degrees with respect to the circumferential direction of the enteric canal.

(5) Image Synthesizing Section's Processing

The image synthesizing section 206 stores three images (RGB images) that have been obtained under the frame sequential illuminating light beams, and synthesizes together the RGB images on a frame-by-frame basis, thereby generating a full-color image to be displayed in real time. In addition, the image synthesizing section 206 also presents a full-color image, obtained by enhancing the depressions of the surface texture with the color blue component, at regular intervals of one frame period without a delay.

Figure 18:
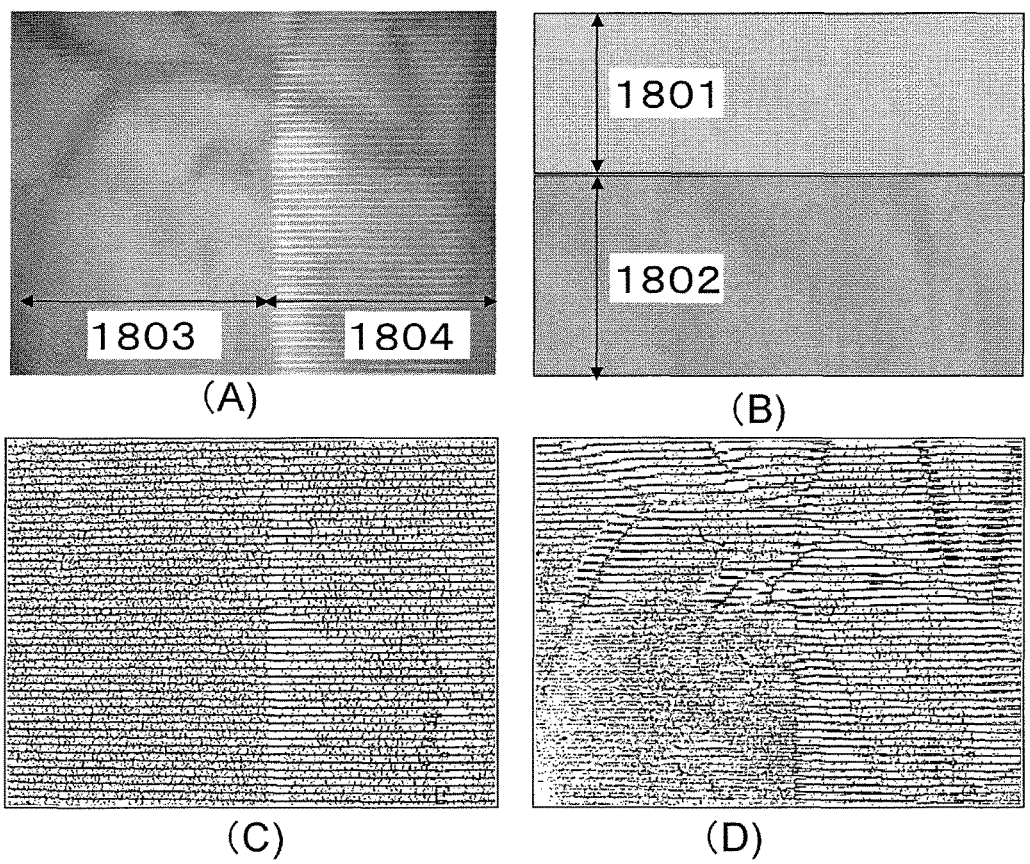
FIG. 18 shows the results of processing that used a reference object.

FIG. 18 shows the results of detection obtained from a groove region using reference objects. As the reference objects, two kinds of translucent white acrylic lenticular plates with somewhat different degrees of transparency (OPAL 422 and OPAL 423 (with dimensions of 50×50×2 mm) produced by Nihon Tokushu Kogaku Jushi Co., Ltd.) were used. In their cross section, semi-cylindrical depressions and projections were arranged in a single direction at a pitch P of 0.7 mm. The grooves had a maximum depth of 0.143 mm and the V grooves defined a maximum tilt angle of 45 degrees with respect to a normal to the lenticular plate. To make the lenticular plates close to the mucosa of a digestive organ, a transparent OHP sheet simulating the blood vessel pattern was put under each of the lenticular plates and a total diffuser was put as the lowermost layer. When shot while being illuminated from right over itself, each of the two kinds of lenticular plates exhibited a similar property to an actual mucosa. Specifically, in each of the lenticular plates, their blood vessel pattern could be seen through the plate, but their surface micro-geometry could not be recognized easily due to diffusion of light.

FIGS. 18(A) and 18(B) show how those reference objects were shot. As shown in Portion (B) of FIG. 18, the two kinds of lenticular plates (including portions 1801 and 1802 with mutually different degrees of transparency) were stacked one upon the other with no gap left vertically between them so that their grooves would run parallel to each other and then irradiated with polarized ring illuminating light from substantially right over themselves. The ring illuminating light was reflected from the surface grooves to produce striped images. But by finely adjusting their angles, those objects were arranged so that almost the entire left half 1803 would make internal diffusion reflection and that almost the entire right half 1804 would make specular reflection.

In the specular reflected region 1804 on the right hand side, the surface grooves could be recognized easily. On the other hand, in the internally diffuse reflected region 1803 on the left-hand side, the surface grooves were difficult to recognize. In particular, in the lenticular plate 1802 with a low degree of transparency at the lower left corner, the surface grooves could be hardly recognized. Meanwhile, a result of detection (C) obtained by capturing differential polarization images and a result of detection (D) obtained by subjecting a conventional light intensity image to the same image processing were compared to each other. In the result of detection (C) obtained by capturing differential polarization images, surface grooves were detected at substantially regular intervals horizontally irrespective of the degrees of transparency of the lenticular plates and the reflection states. On the other hand, the result of detection (D) obtained by using a conventional light intensity image was affected by the blood vessel pattern that was seen through under the plate, and had a lot of noise. And in the result (D), the grooves were not sufficiently parallel to each other and their intervals were not regular, either. These results reveal that in detecting the micro-geometry on the surface of a translucent object, the polarization differential processing will work more effectively than the light intensity processing.

Each of the reference objects was irradiated with polarized illuminating light with its angle changed by 45 degrees each time to capture parallel and crossed Nicols polarization images, on which four kinds of differential polarization images were obtained. And the interval between the grooves was extracted and the average Ave. and variance Var. of the intervals were obtained. As a result, the effectiveness of the processing shown in FIG. 17A could be confirmed.

Next, the results of an experiment using a stomach enucleated from a pig that had died three hours before (which will be hereinafter referred to as a "pig's stomach") will be described. Four images, namely, L0C0 (P//), L0C90 (P⊥), L90C90 (S⊥) and L90C0 (S//), were captured. In the parallel Nicols images, the light was specular-reflected significantly from the surface of the mucosa. In the crossed Nicols images, on the other hand, the colors at a depth of the mucosa were observed. Based on these images, L0-Dif and L90-Dif images were generated as a differential polarization image between L0C0 and L0C90 and a as a differential polarization image between L90C90 and L90C0, respectively, their enhanced images were generated, and the two enhanced images were added together and their average was calculated.

Figure 19:
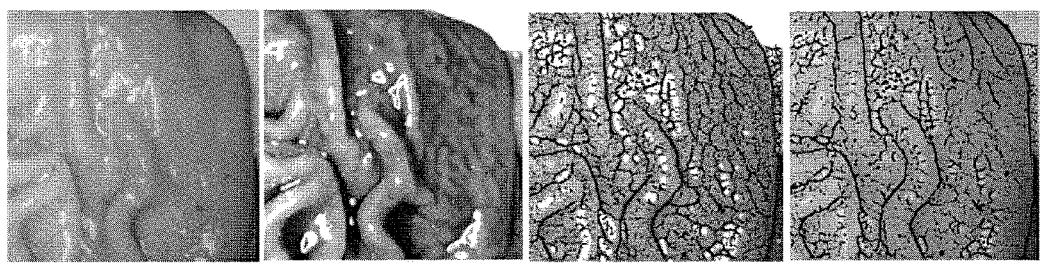
FIG. 19 shows the results of processing that used a porcine's stomach.
Figure 19:
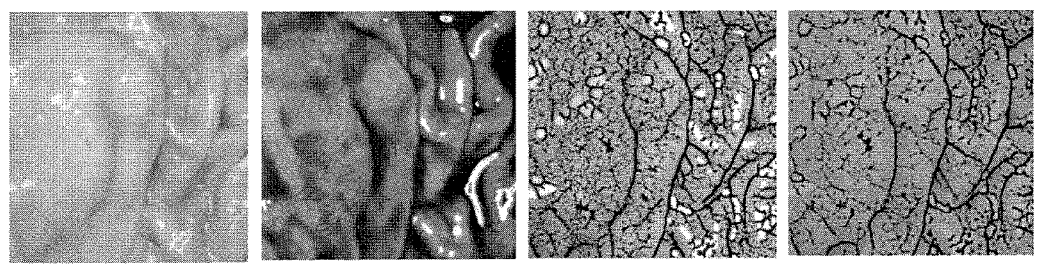

The results of the processing are shown in FIG. 19. Partially enlarged images of two different parts are shown in the upper and lower portions of FIG. 19. Portions (A) show color light intensity images of the pig's stomach. On the surface, macroscopic depressions and projections and pleats were observed, but the micro-geometric structure of the surface could not be observed at all. Portions (B) show light intensity images that were obtained by sprinkling an indigo carmine solution over the pig's stomach. Portions (C) show the results of enhancement obtained by performing polarization image processing with the technique of the present disclosure adopted. And portions (D) show the results of enhancement obtained by performing mere light intensity image processing. According to the light intensity image processing shown in portions (D), the macroscopic depressions and projections and pleats that were observed in portions (A) could be detected, but the micro-geometric surface structure of the plane regions could not be detected sufficiently. On the other hand, according to the technique of the present disclosure shown in portions (C), not only the micro-geometric surface structure could be detected in detail but also the macroscopic depressions and projection and the halation region of the specular reflection could be recognized clearly. Compared to the indigo carmine sprinkled images shown in portions (B), the surface unevenness to be sensed easily in portions (B) thanks to the "pooling" phenomenon of the liquid could not be reproduced in portions (D), but the surface structure that was hidden by the pool in portions (B) could be enhanced well enough to recognize it easily.

Embodiment 2

Figure 20:
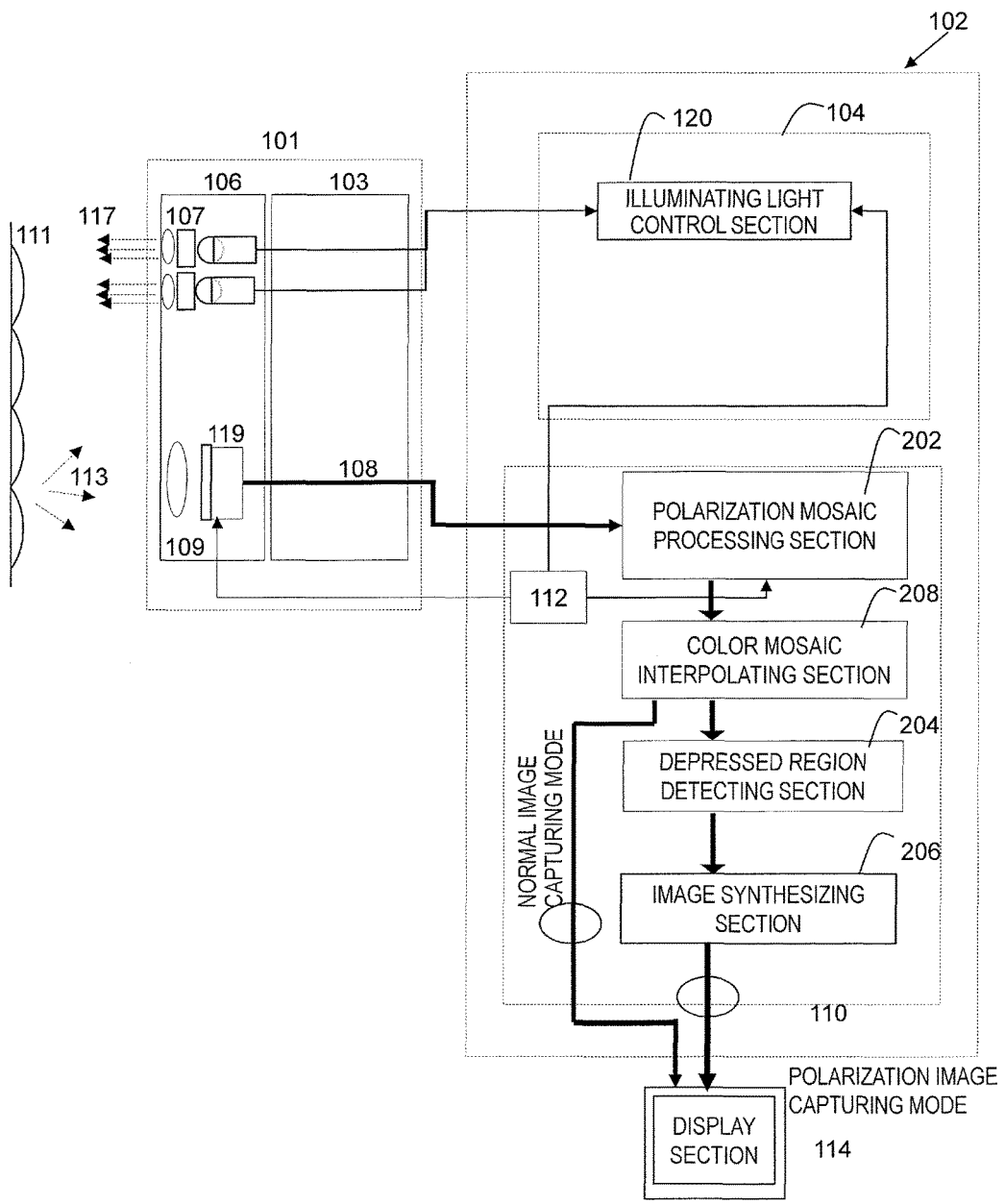
FIG. 20 is a block diagram illustrating a configuration for a second embodiment of the present disclosure.

FIG. 20 schematically illustrates an overall configuration for an image processing apparatus as a second embodiment of the present disclosure. In this embodiment, the object is irradiated with white light and a color image is captured by a single-panel color image sensor 119. In this embodiment, when the object is irradiated with the white light, a rotating polarized illuminating light source should be used. For that purpose, according to this embodiment, only an illuminating light control section is arranged in the light source unit 104 and illuminating light is produced by either an LED which is arranged at the tip of the endoscope or an organic EL surface-emitting light source, for example.

Figure 21:
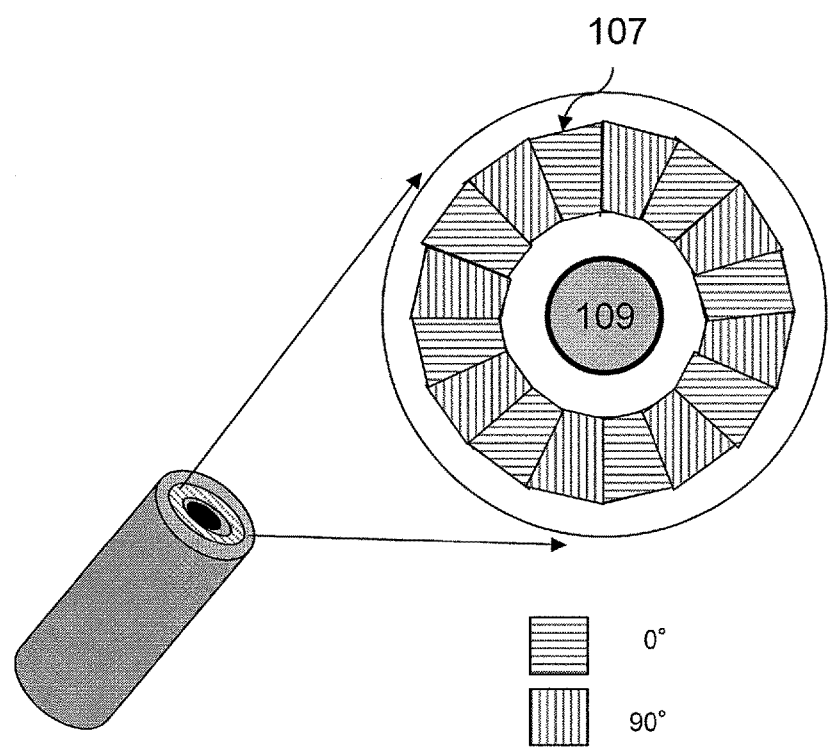
FIG. 21 illustrates the tip portion of an endoscope and a rotating polarized illuminating light source according to the second embodiment of the present disclosure.

In this embodiment, a number of (e.g., sixteen in this example) emission ports, through which an illuminating light beam, of which the polarization plane defines 0 degrees (i.e., P-polarized), and an illuminating light beam, of which the polarization plane defines 90 degrees (i.e., S-polarized), are emitted alternately, are arranged at the tip of the endoscope as shown in FIG. 21, for example. In this example, by lighting one of the two sets of LEDs, each consisting of non-adjacent eight LEDs of the same type, selectively and alternately, a polarized illuminating source which emits P- and S-polarized light beams alternately is realized.

Figure 22:
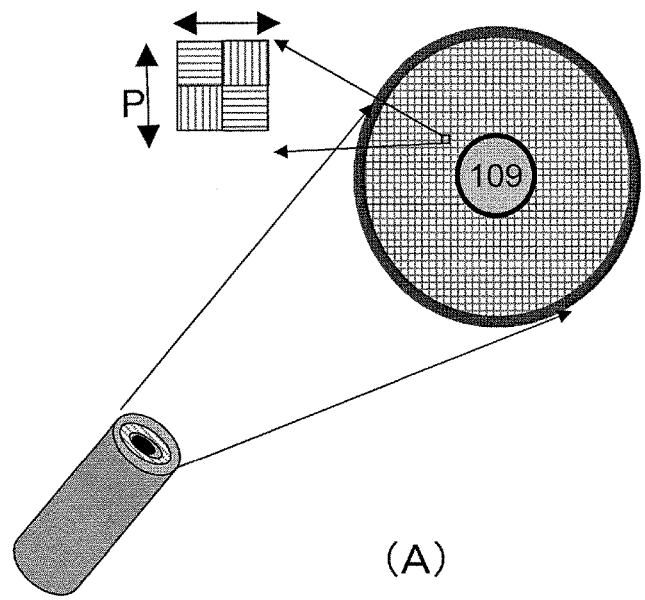
FIG. 22 illustrates another configuration for a rotating polarized illuminating light source according to the second embodiment of the present disclosure.
Figure 22:
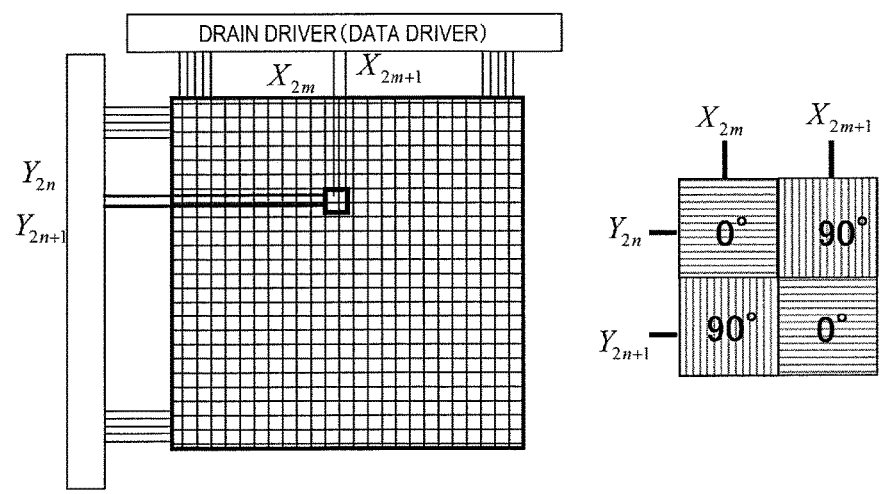

Potion (A) of FIG. 22 illustrates another exemplary rotating polarized illuminating light source. In this example, by providing a far larger number of sufficiently small illuminating pixel units to be sequentially turned ON, the variation in the position of the light source to be lit can be limited to within one pixel at the image sensor end. Potion (B) of FIG. 22 illustrates an overall configuration for such a plane illuminating light source. As shown in potion (B) of FIG. 22, a data driver for controlling the sequential lighting is arranged along each of the X and Y axes of the plane illuminating light source, and the pixels addressed on the X and Y axes are all turned ON simultaneously. For example, if all even-numbered pixels ($X_{2m}$ and $Y_{2m}$) on the X and Y axes are turned ON simultaneously, then an illuminating light beam, of which the polarization plane defines zero degrees, will be emitted. And by appropriately combining the even and odd numbers in the X- and Y-axis data drivers, an illuminating light beam, of which the polarization transmission plane defines 0 degrees (P), and an illuminating light beam, of which the polarization transmission plane defines 90 degrees (S), are obtained.

One of the advantages achieved by using such a plane illuminating light source is that only the polarization state of the illuminating light can be changed with the overall illuminance and light distribution state unchanged. By using a plane light source as the illuminating light source, the degree of uniformity of the illuminating light can be increased. As a result, the very high intensity of the light that has been specular-reflected from the surface mucosa of an organ can be lowered and the object can be shot just as intended.

Figure 23:
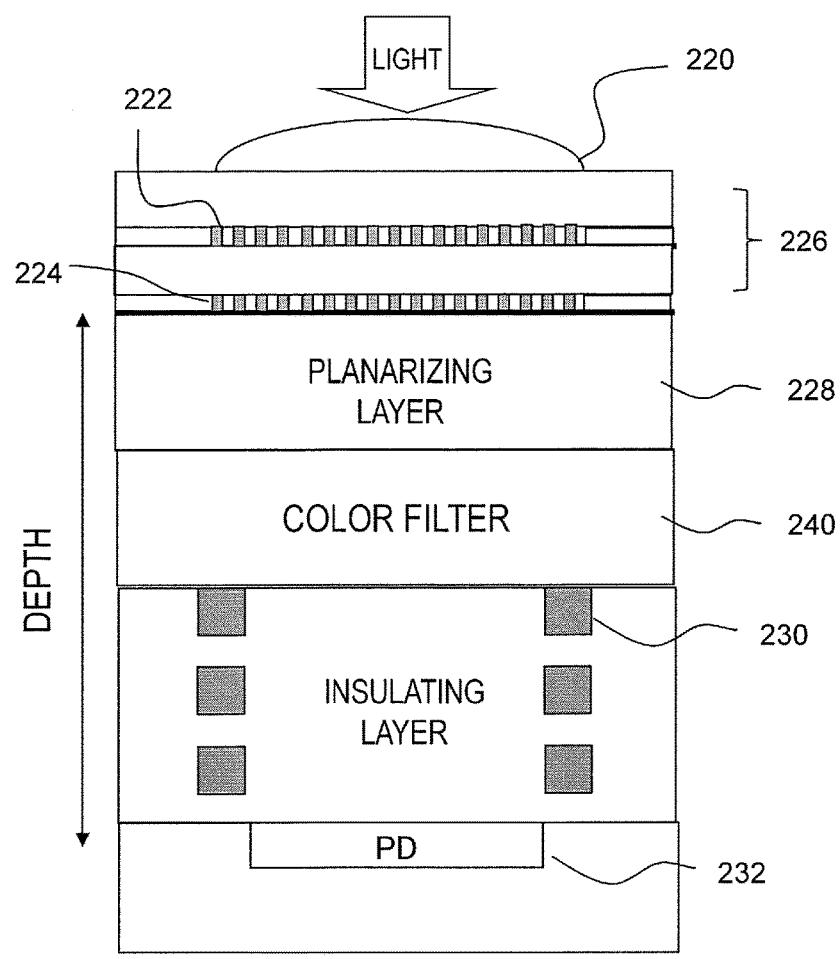
FIG. 23 illustrates a cross-sectional structure of a color polarization image sensor according to the second embodiment of the present disclosure.

FIG. 23 illustrates an exemplary cross-sectional structure for a color polarization image sensor 119 for use in this embodiment. In this color polarization image sensor 119, a color filter 240 is inserted between the wire grid layer 224 and the PD (photodiode) 232, which is a difference from the monochrome broadband polarization image sensor 115 shown in FIG. 10. This color filter 240 may be made of either an organic substance or a photonic crystal or a metal. When viewed in the direction in which the incoming light travels from the light source toward the PD 232, there are six different orders in which the micro lens 220, the first wire grid layer 222, the second wire grid layer 224, and the color filter 240 can be arranged and which have respectively different advantages. In this example, the distance DEPTH from the wire grid 224 to the PD 232 increases by the insertion of the color filter 240 and is typically in the range of 4 to 6 μm.

For example, in the configuration shown in FIG. 23 in which the micro lens 220, the first wire grid layer 222, the second wire grid layer 224, and the color filter 240 are stacked in this order from the top toward the bottom, the micro lens 220 forms the uppermost layer, and therefore, incoming light can be easily made incident perpendicularly to the wire grids.

Figure 24:
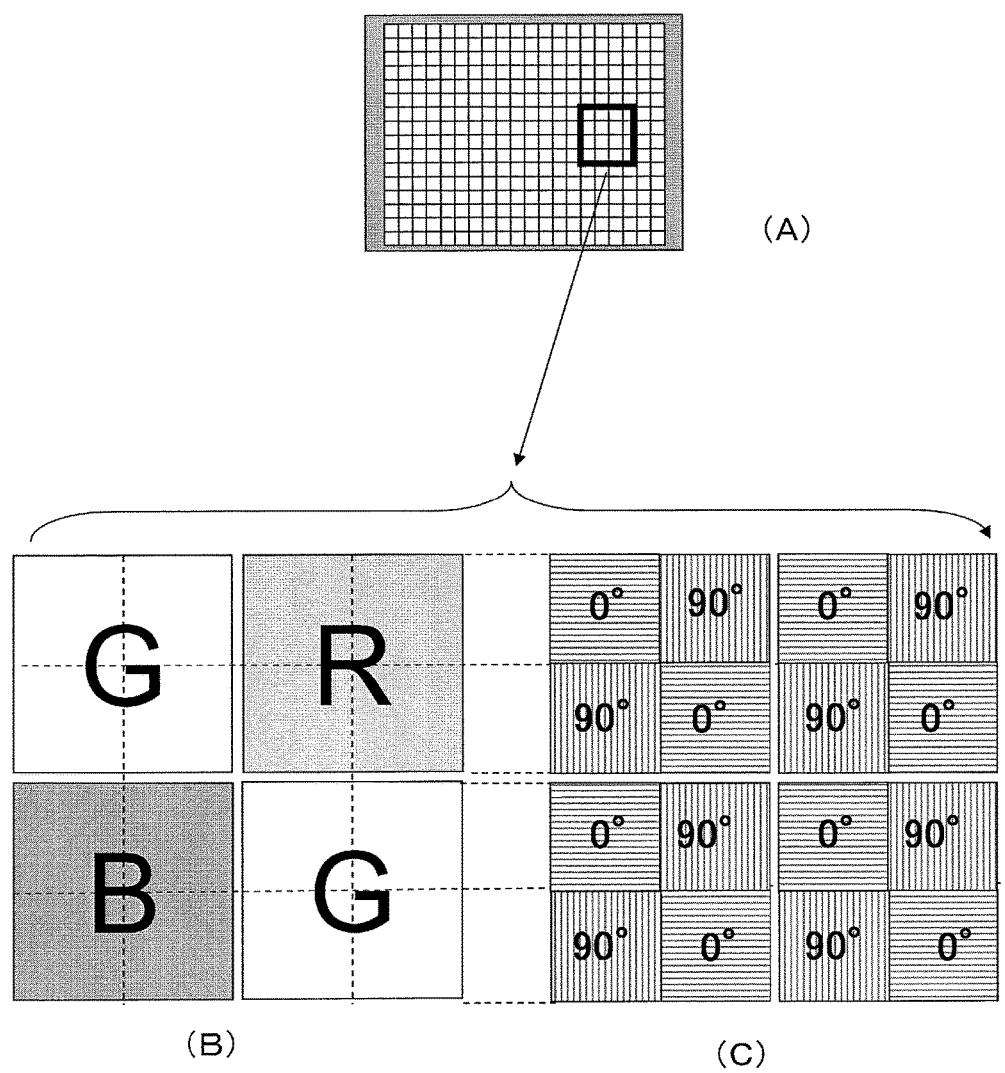
FIG. 24 illustrates planar arrangements of a color mosaic and a polarization mosaic according to the second embodiment of the present disclosure.

FIG. 24 illustrates a planar structure for the color polarization image sensor 119 shown in FIG. 23. Specifically, portion (A) of FIG. 24 illustrates the same planar structure as the single-panel color image sensor. In the exemplary configuration shown in portion (A) of FIG. 24, if the 4×4 pixel region is expanded and when viewed from right over the image sensor 119, the color mosaic structure shown in portion (B) of FIG. 24 and the polarization mosaic structure shown in portion (C) of FIG. 24 are laid one upon the other on a pixel-by-pixel basis.

Portion (B) of FIG. 24 illustrates an exemplary color mosaic filter. That is to say, the color mosaic filter that can be used in an embodiment of the present disclosure does not have to be the one shown in portion (B) of FIG. 24. For example, the color mosaic filter does not have to have a Bayer mosaic arrangement but may also have any other mosaic structure. In this example, a filter in a single color included in the color mosaic covers the region in which four pixels (i.e., four photodiodes) are arranged in two columns and two rows. The 2×2 pixel region is associated with the four kinds of polarization mosaic regions shown in portion (C) of FIG. 24. That is to say, even though the resolution (or the number of pixels) of this image sensor is just a quarter (i.e., ½×½) of the original one when considered on a subpixel basis, the artifacts to be generated as a result of polarized light processing can be reduced by carrying out the polarized light processing within a single pixel.

Figure 25:
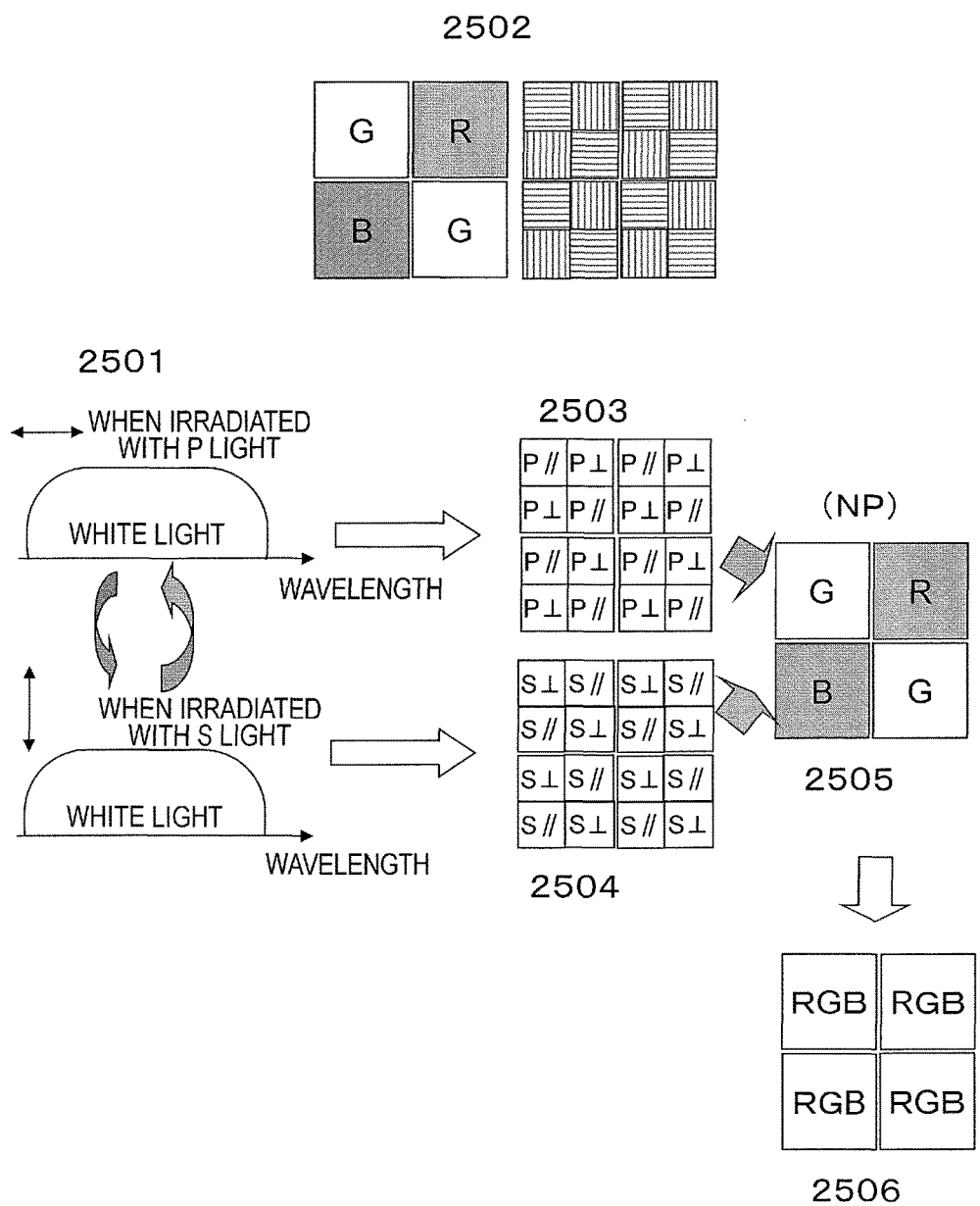
FIG. 25 illustrates how the polarization mosaic processing section 202 operates in the normal image capturing mode according to the second embodiment of the present disclosure.

Next, it will be described with reference to FIG. 25 how the image processing apparatus of this embodiment operates in the normal image capturing mode. The object is alternately irradiated with a white P-polarized light beam and a white S-polarized light beam. And every time the object is irradiated with a polarized light beam, a polarization color mosaic image is obtained. Specifically, when the object is irradiated with a P-polarized light beam, a polarization pixel pattern 2503 is obtained by the polarization mosaic 2502. On the other hand, when the object is irradiated with an S-polarized light beam, a polarization pixel pattern 2504 is obtained by the polarization mosaic 2502. In FIG. 25, P // indicates pixels in the parallel-Nicols state when irradiated with a P-polarized light beam, and P // indicates pixels in the crossed-Nicols state when irradiated with a P-polarized light beam. Likewise, S // indicates pixels in the parallel-Nicols state when irradiated with an S-polarized light beam, and S⊥ indicates pixels in the crossed-Nicols state when irradiated with an S-polarized light beam. The polarization mosaic processing section 202 adds together the images with these polarization pixel patterns 2503 and 2504 and calculates their average on a pixel-by-pixel basis. If that adding and averaging processing is carried out on each color pixel based on the polarization pixel patterns 2503 and 2504, the values of pixels in the parallel-Nicols state and the values of pixels in the crossed-Nicols state can be uniformly mixed together as represented by the following equation:

$$(NP)=(P//+P\perp+S//+S\perp)/4$$

As a result of this adding and averaging processing, a non-polarization (NP) color mosaic image 2505, of which the resolution is just a quarter (=½×½) of the original one, is obtained. The processing of generating a full-color image based on this non-polarization color mosaic image 2505 may be carried out by ordinary color mosaic interpolation.

Figure 26:
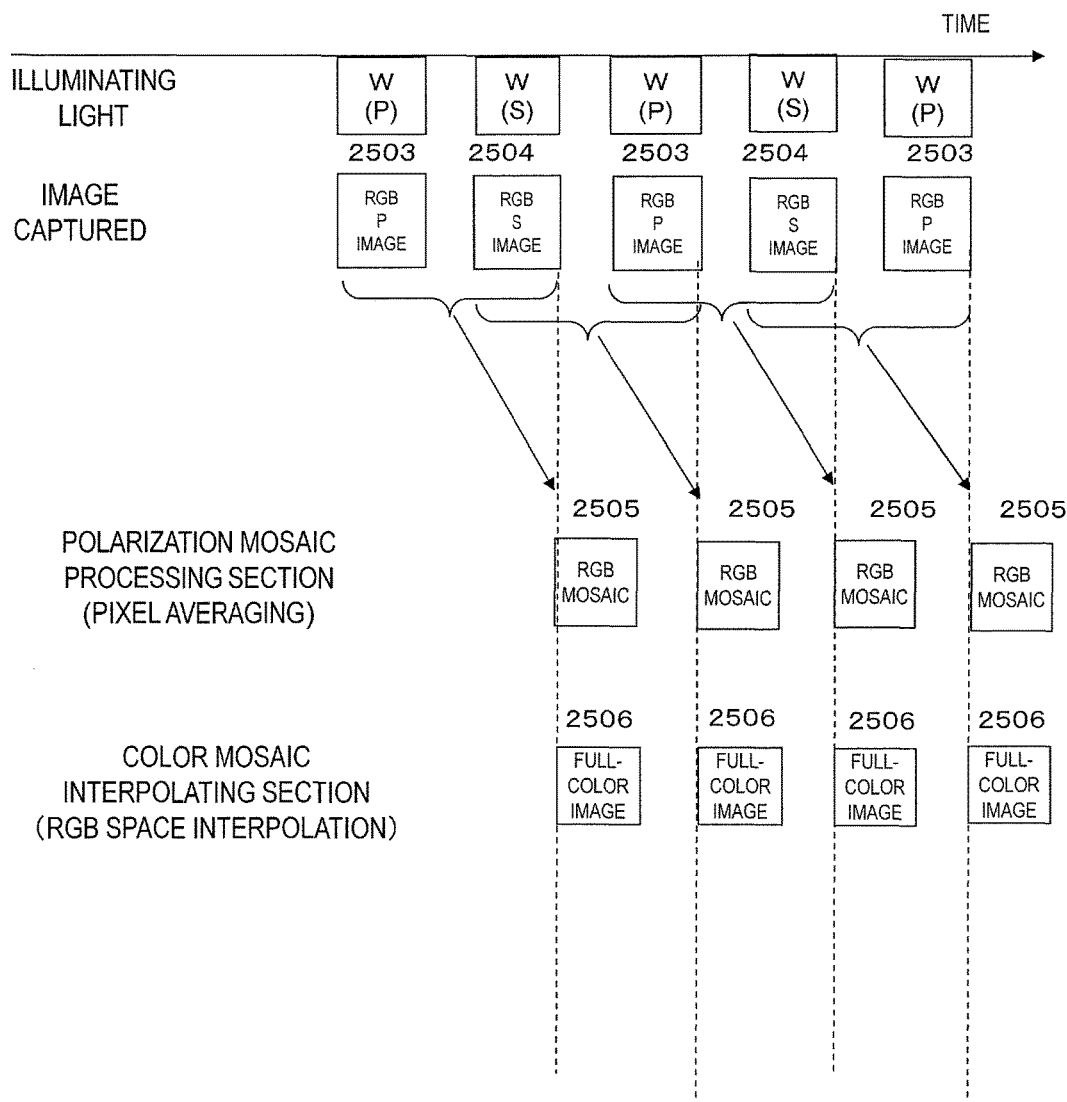
FIG. 26 is a timing chart showing how the apparatus according to the second embodiment of the present disclosure operates in the normal image capturing mode.

FIG. 26 is a timing chart showing the sequence of these operations. Specifically, the operation of emitting illuminating light beams, the image capturing operation, and the color component images processed by the polarization mosaic processing section 202 are shown in this order from top to bottom of FIG. 26. The respective operations are performed at these timings under the control of the synchronizer 112. When the object is alternately irradiated with a P-polarized light beam and an S-polarized light beam, their associated polarization pixel patterns 2503 and 2504 are captured. The polarization mosaic processing section 202 carries out the adding and averaging processing on the polarization pixel patterns 2503 and 2504 shown in FIG. 25, thereby obtaining a non-polarization color mosaic image 2505. Next, by performing color mosaic interpolation processing, an RGB full-color image is obtained. Consequently, by irradiating the object with a P-polarized illuminating light beam and an S-polarized illuminating light beam, a single RGB full-color image can be obtained. Actually, by performing temporally adjacent P-polarized illuminating light processing and S-polarized illuminating light processing continuously as shown in FIG. 26, images can be generated as a moving picture at regular interval of one frame period without causing a delay.

Optionally, in this mode, the P-polarized illuminating light beam and the S-polarized illuminating light beam may be emitted simultaneously instead of being emitted alternately. Even so, an RGB full-color image can also be obtained by performing the same color mosaic interpolation processing.

Figure 27:
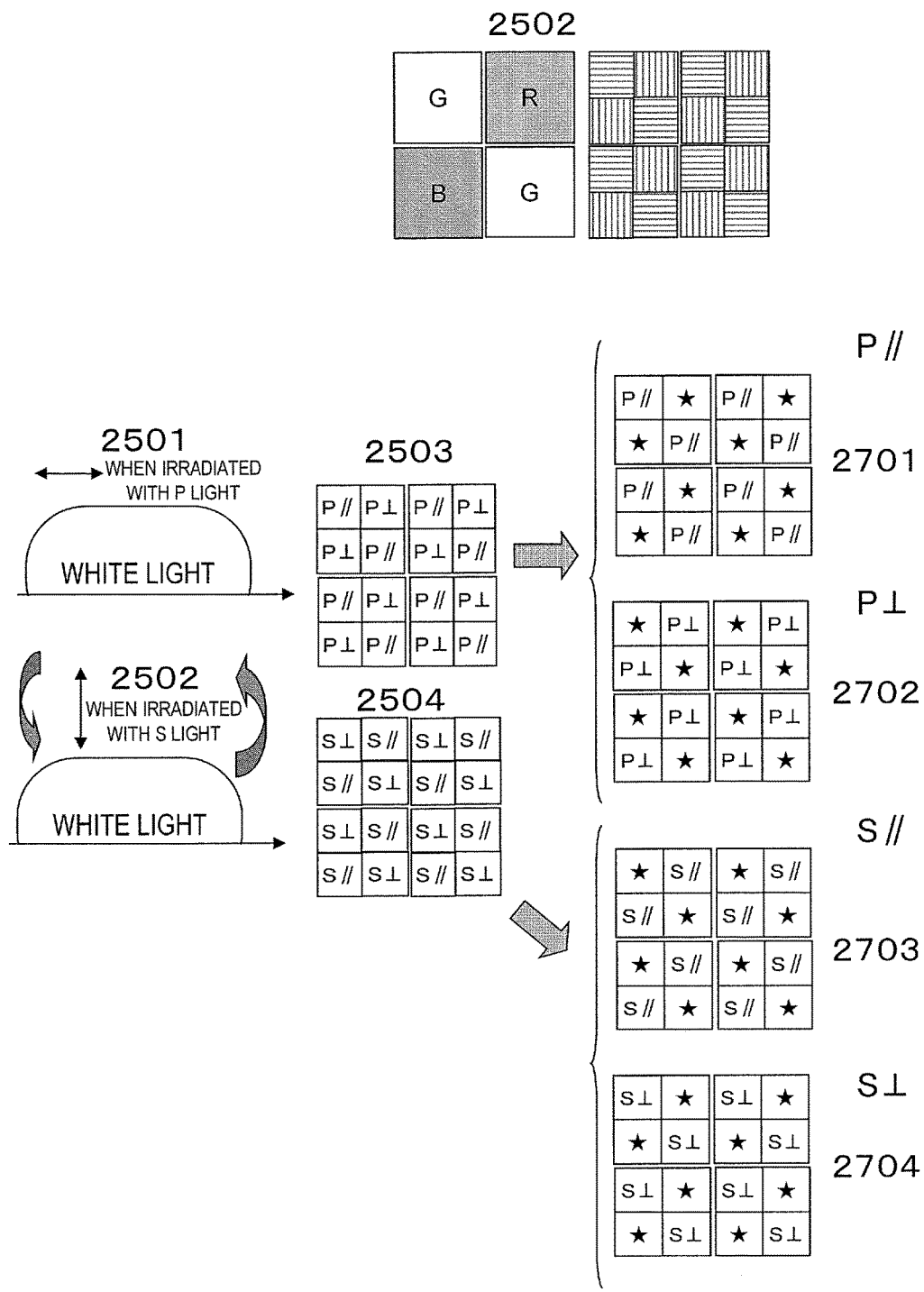
FIG. 27 illustrates how the polarization mosaic processing section 202 operates in the polarization image capturing mode according to the second embodiment of the present disclosure.

FIG. 27 illustrates how the image processing apparatus of this embodiment operates in the polarization image capturing mode, in which the object is alternately irradiated with a P-polarized light beam and an S-polarized light beam and a polarization color mosaic image is obtained every time the object is irradiated with such a polarized light beam. The polarization pixel patterns 2503 and 2504 obtained in this case are the same as the polarization pixel patterns 2503 and 2504 shown in FIG. 25. Using both of these pixel patterns 2503 and 2504, the polarization mosaic processing section 202 selects and integrates together P// and S// and P⊥ and S⊥ for each pixel in question and makes interpolation on surrounding pixels for a missing pixel. In this manner, four kinds of polarization images, namely, parallel and crossed Nicols images 2701 and 2702 under a P-polarized illuminating light beam and parallel and crossed Nicols images 2703 and 2704 under an S-polarized illuminating light beam, are generated separately. In FIG. 27, ★ indicates pixels to be interpolated.

These four kinds of polarization images obtained as a result of this processing are subjected to the same processing as what has already been described for the first embodiment with reference to FIGS. 14 and 17A by the depressed region detecting section 204 and the image synthesizing section 206.

Figure 28:
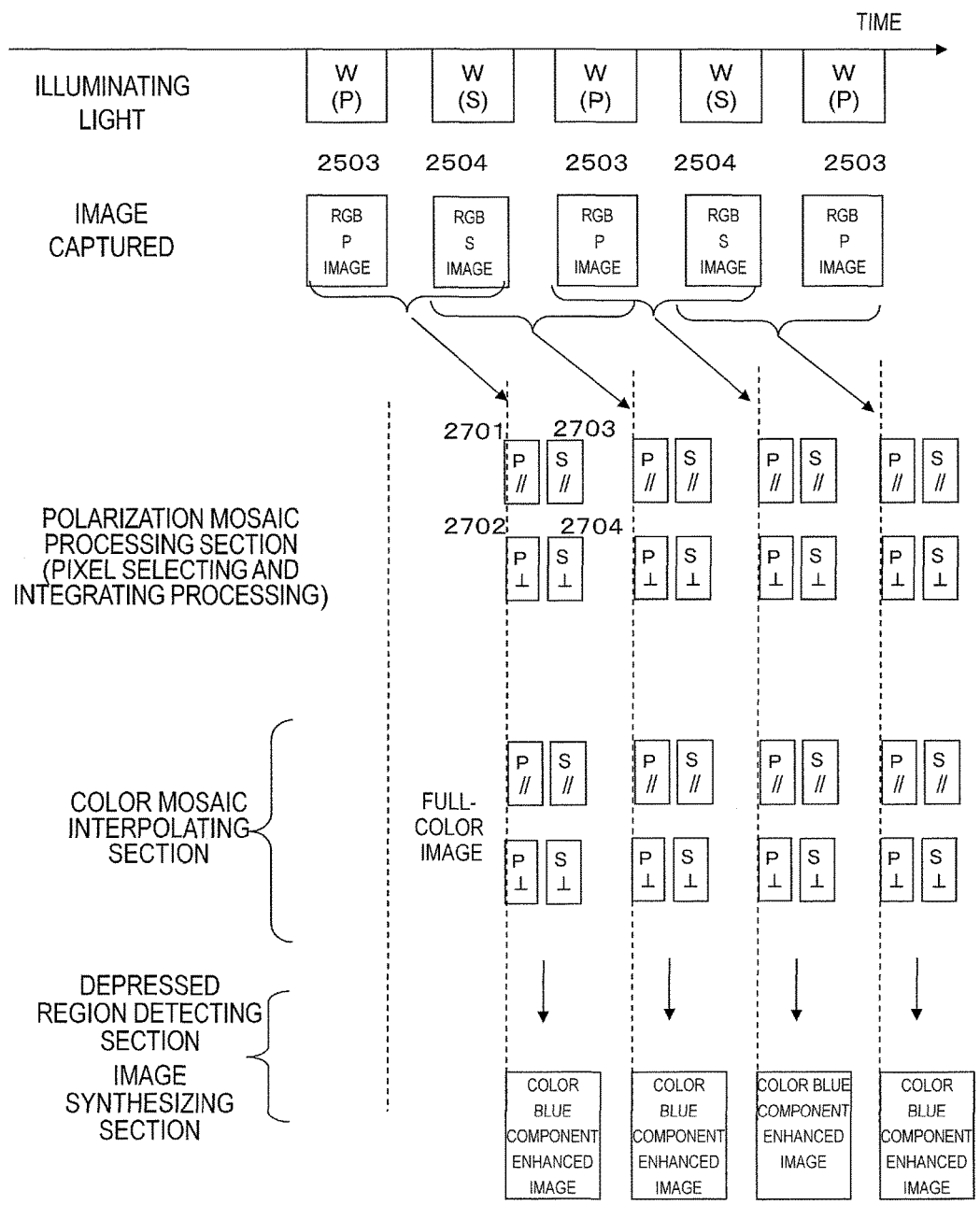
FIG. 28 is a timing chart showing how the apparatus according to the second embodiment of the present disclosure operates in the polarization image capturing mode.

FIG. 28 is a timing chart showing the sequence of these operations. Specifically, the operation of emitting illuminating light beams, the image capturing operation, and the color images processed by the polarization mosaic processing section 202, the color mosaic interpolating section 208, the depressed region detecting section 204, and the image synthesizing section 206 are shown in this order from top to bottom of FIG. 28. The operation of emitting illuminating light beams and the image capturing operation are the same as in the normal image capturing mode timing chart shown in FIG. 26. The polarization mosaic processing section 202 operates so as to generate parallel and crossed Nicols images 2701 and 2702 under a P-polarized light beam and parallel and crossed Nicols images 2703 and 2704 under an S-polarized light beam by using an image captured under a P-polarized illuminating light beam and an image captured under an S-polarized illuminating light beam on a frame-by-frame basis. That is to say, four different kinds of polarization pixel patterns 2701, 2702, 2703 and 2704 are generated on a frame-by-frame basis. As already described for the first embodiment with reference to FIGS. 14 and 17A, those images are presented every frame as a moving picture on the display section 114 as a full-color image, of which the color blue component has been enhanced at the depressions of the surface texture by the depressed region detecting section 204 and the image synthesizing section 206.

MODIFIED EXAMPLE 1 OF EMBODIMENT 2

Figure 29:
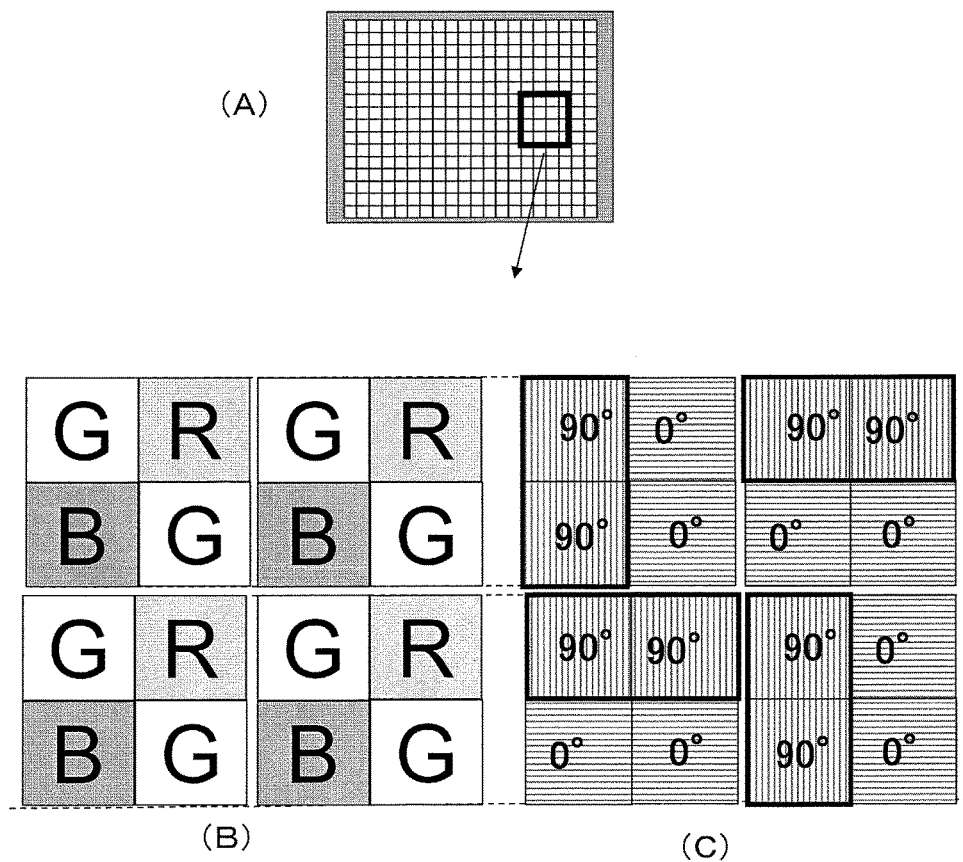
FIG. 29 illustrates planar arrangements of a color mosaic and a polarization mosaic according to a first modified example of the second embodiment of the present disclosure.

FIG. 29 illustrates a first modified example of the second embodiment of the present disclosure. Portion (A) of FIG. 29 illustrates a planar structure of the color polarization image sensor 119 of the second embodiment shown in FIG. 23. The planar structure shown in FIG. 29(A) is the same as that of a color single-panel image sensor. Portion (B) of FIG. 29 illustrates an exemplary arrangement of 4×4 color filters in the color mosaic. And portion (C) of FIG. 29 illustrates an exemplary arrangement of eight polarizers in a polarization mosaic. These color and polarization mosaics are stacked one upon the other to cover 4×4 pixels (or PDs (photodiodes)).

In this embodiment, color filters in two colors of the color mosaic are associated with a single rectangular polarizer. In the other respects, this configuration is the same as that of the second embodiment.

The pixels over which polarizers indicated with an angle of 0 degrees in portion (C) of FIG. 29 are located are pixels which transmit a P-polarized light beam, and the pixels over which polarizers indicated with an angle of 90 degrees are located are pixels which transmit an S-polarized light beam. In this case, the 0 degree polarizers and the 90 degree polarizers do not form a checkerboard pattern. That is to say, this polarization mosaic is formed so that the same polarized light beam is incident on two pixels which are vertically or horizontally adjacent to each other within the image capturing plane. This arrangement is adopted so that a 0 degree polarizer and a 90 degree polarizer are always allocated to two G pixels which form parts of the RGB pixels. In such a configuration, the 0 degree polarizer is allocated to the two pixels of RG and the two pixels of BG, and the 90 degree polarizer is allocated to the two pixels of GB and the two pixels of GR.

Figure 30:
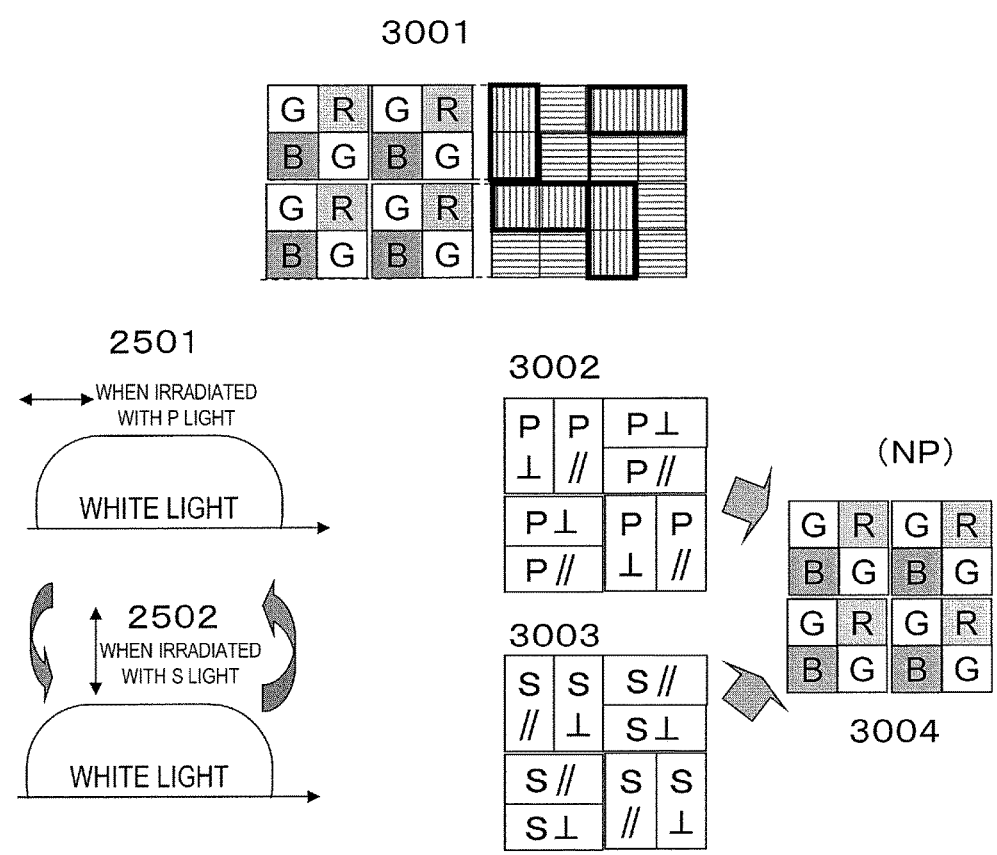
FIG. 30 illustrates how the polarization mosaic processing section 202 operates in the normal image capturing mode according to the first modified example of the second embodiment of the present disclosure.

FIG. 30 illustrates how the image processing apparatus of this embodiment operates in the normal image capturing mode, in which the object is irradiated with a white P-polarized light beam and a white S-polarized light beam alternately, an image is captured every time the object is irradiated with such a polarized light beam, and a polarization color mosaic image is obtained as a result. Since the polarization mosaic has the arrangement 3001, a polarization pixel pattern 3002 is obtained when the object is irradiated with a P-polarized light beam and a polarization pixel pattern 3003 is obtained when the object is irradiated with an S-polarized light beam. In FIG. 30, P// and P⊥ indicate pixels in the parallel Nicols state and pixels in the crossed Nicols state when the object is irradiated with a P-polarized light beam. Likewise, S// and S⊥ indicate pixels in the parallel Nicols state and pixels in the crossed Nicols state when the object is irradiated with an S-polarized light beam. The polarization mosaic processing section 202 adds together these polarization pixel patterns 3002 and 3003 and calculates their average on a pixel-by-pixel basis. In this adding and averaging processing, the pixels in the parallel Nicols state and the pixels in the crossed Nicols state would be mixed together uniformly in the following manner.

$$(NP) = (P\perp + S//)/2$$

$$(NP) = (P// + S\perp)/2$$

As a result of this adding and averaging processing, a non-polarization color mosaic image 3004 is obtained. In this case, the resolution does not decrease unlike the second embodiment. The processing of generating a full-color image based on this non-polarization color mosaic image 3004 may be carried out by normal color mosaic interpolation.

Figure 31:
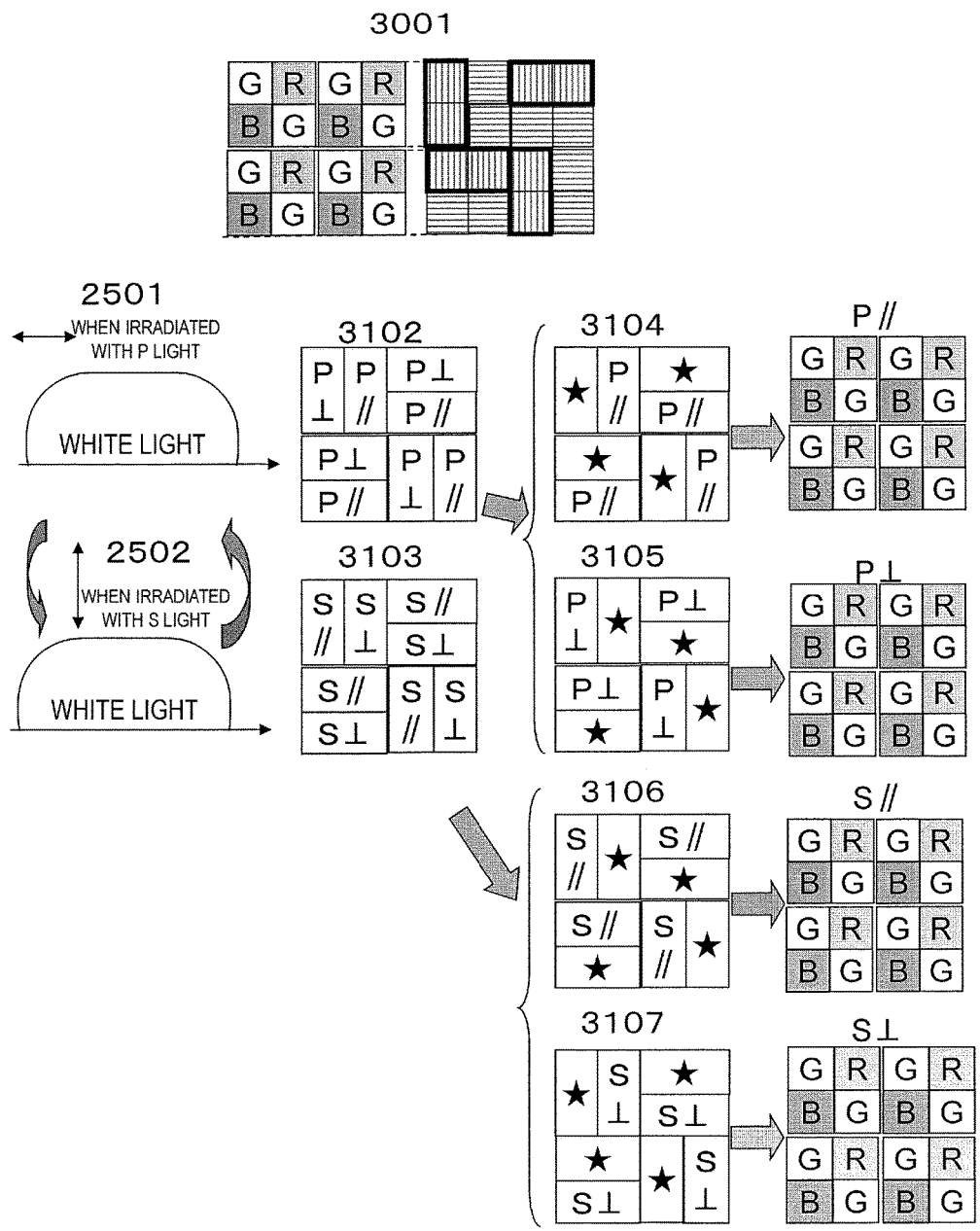
FIG. 31 illustrates how the polarization mosaic processing section 202 operates in the polarization image capturing mode according to the first modified example of the second embodiment of the present disclosure.

FIG. 31 illustrates how the image processing apparatus of this embodiment operates in the polarization image capturing mode, in which the object is alternately irradiated with a P-polarized light beam and an S-polarized light beam, and images are captured and polarization pixel patterns 3102 and 3103 are obtained every time the object is irradiated with such a polarized light beam. Using both of these polarization pixel patterns 3102 and 3103, the polarization mosaic processing section 202 collects, fills and interpolates with pixels with P// and S// and P⊥ and S⊥ for each pixel in question. In this manner, parallel and crossed Nicols image 3104 and 3105 under a P-polarized illuminating light beam and parallel and crossed Nicols image 3106 and 3107 under an S-polarized illuminating light beam are generated separately. The polarization images obtained as a result of this processing are color mosaic images, which are subjected to a color mosaic interpolation, thereby generating four kinds of full-color polarization images. The crossed Nicols images are subjected to the same processing by the depressed region detecting section 204 and the image synthesizing section 206 as what has already been described for the first embodiment. It should be noted that the timing chart for this embodiment is the same as the timing chart for the second embodiment.

MODIFIED EXAMPLE 2 OF EMBODIMENT 2

Figure 32:
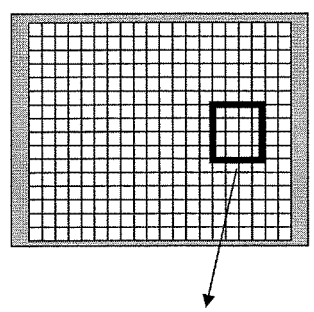
FIG. 32 illustrates planar arrangements of a color mosaic and a polarization mosaic according to a second modified example of the second embodiment of the present disclosure.
Figure 32:
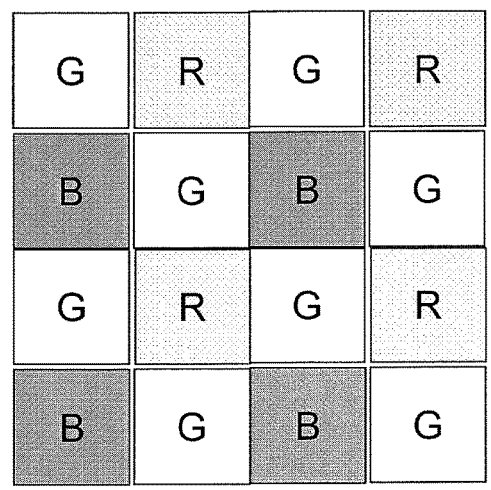
Figure 32:
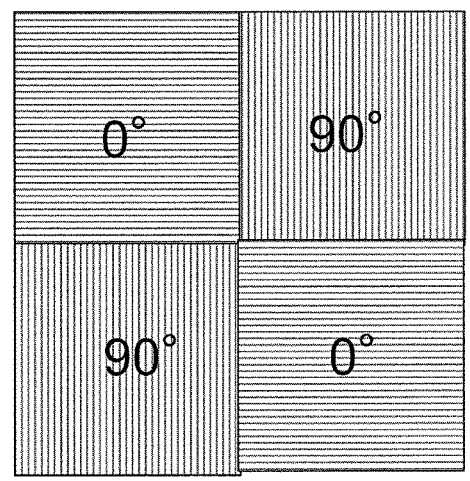

FIG. 32 illustrates a second modified example of the second embodiment of the present disclosure. Portion (A) of FIG. 32 illustrates a planar structure of the color polarization image sensor 119 shown in FIG. 23. Portion (B) of FIG. 32 illustrates an exemplary arrangement of 4×4 color filters in the color mosaic. And portion (C) of FIG. 32 illustrates an exemplary arrangement of four polarizers in a polarization mosaic. These color and polarization mosaics are stacked one upon the other to cover 4×4 pixels (or PDs (photodiodes)).

In this embodiment, four pixels that form a single unit of the color Bayer mosaic are associated with a single unit of the polarization mosaic. In the other respects, the configuration of this embodiment is the same as that of the second embodiment. The pixels over which polarizers indicated with an angle of 0 degrees in portion (C) of FIG. 32 are located are pixels which transmit a P-polarized light beam, and the pixels over which polarizers indicated with an angle of 90 degrees are located are pixels which transmit an S-polarized light beam. In this case, the 0 degree polarizers and the 90 degree polarizers of the polarization mosaic form a checkerboard pattern, and the same color Bayer mosaic is included in each of those polarizers.

Figure 33:
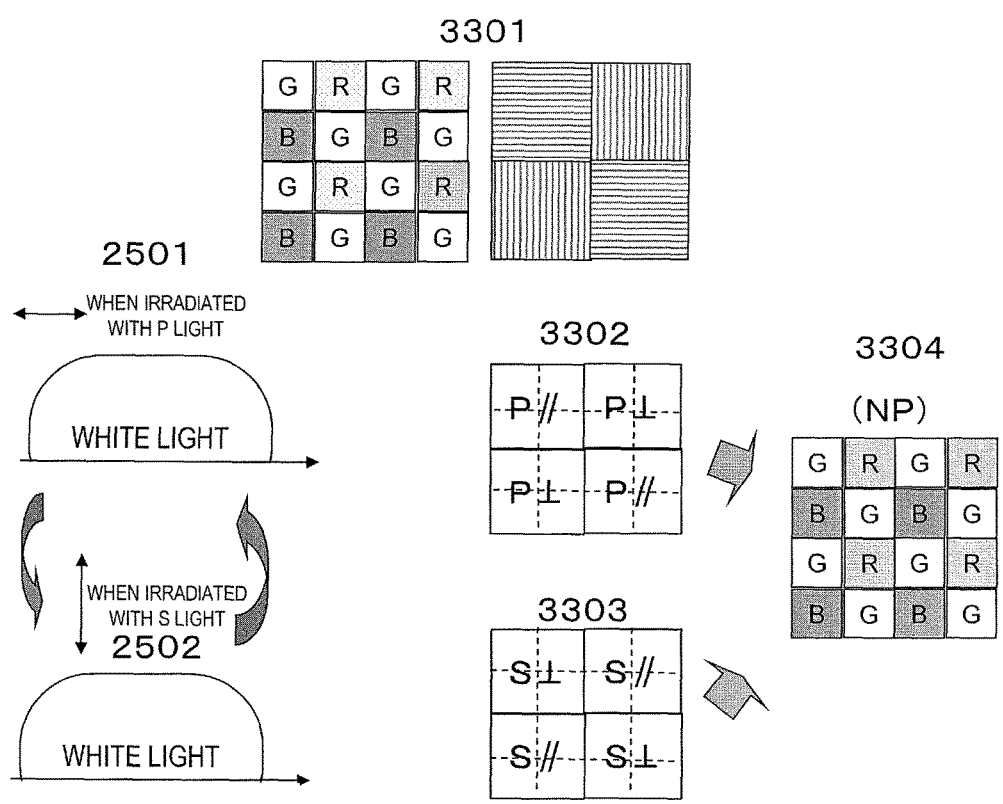
FIG. 33 illustrates how the polarization mosaic processing section 202 operates in the normal image capturing mode according to the second modified example of the second embodiment of the present disclosure.

FIG. 33 illustrates how the image processing apparatus of this embodiment operates in the normal image capturing mode, in which the object is irradiated with a white P-polarized light beam and a white S-polarized light beam alternately, an image is captured every time the object is irradiated with such a polarized light beam, and a polarization color mosaic image is obtained as a result. Since the polarization mosaic has the arrangement 3301, a polarization pixel pattern 3302 is obtained when the object is irradiated with a P-polarized light beam and a polarization pixel pattern 3303 is obtained when the object is irradiated with an S-polarized light beam. In FIG. 33, P//, P⊥, S// and S⊥ have the same meanings as what has already been described. The polarization mosaic processing section 202 adds together the images with these polarization pixel patterns 3302 and 3303 and calculates their average on a pixel-by-pixel basis. In this adding and averaging processing, the pixels in the parallel Nicols state and the pixels in the crossed Nicols state would be mixed together.

As a result of this adding and averaging processing, a non-polarization color mosaic image 3304 is obtained. In this case, unlike the second embodiment, the resolution does not decrease, which is a feature of this modified example. The processing of generating a full-color image based on this non-polarization color mosaic image may be carried out by normal color mosaic interpolation.

Figure 34:
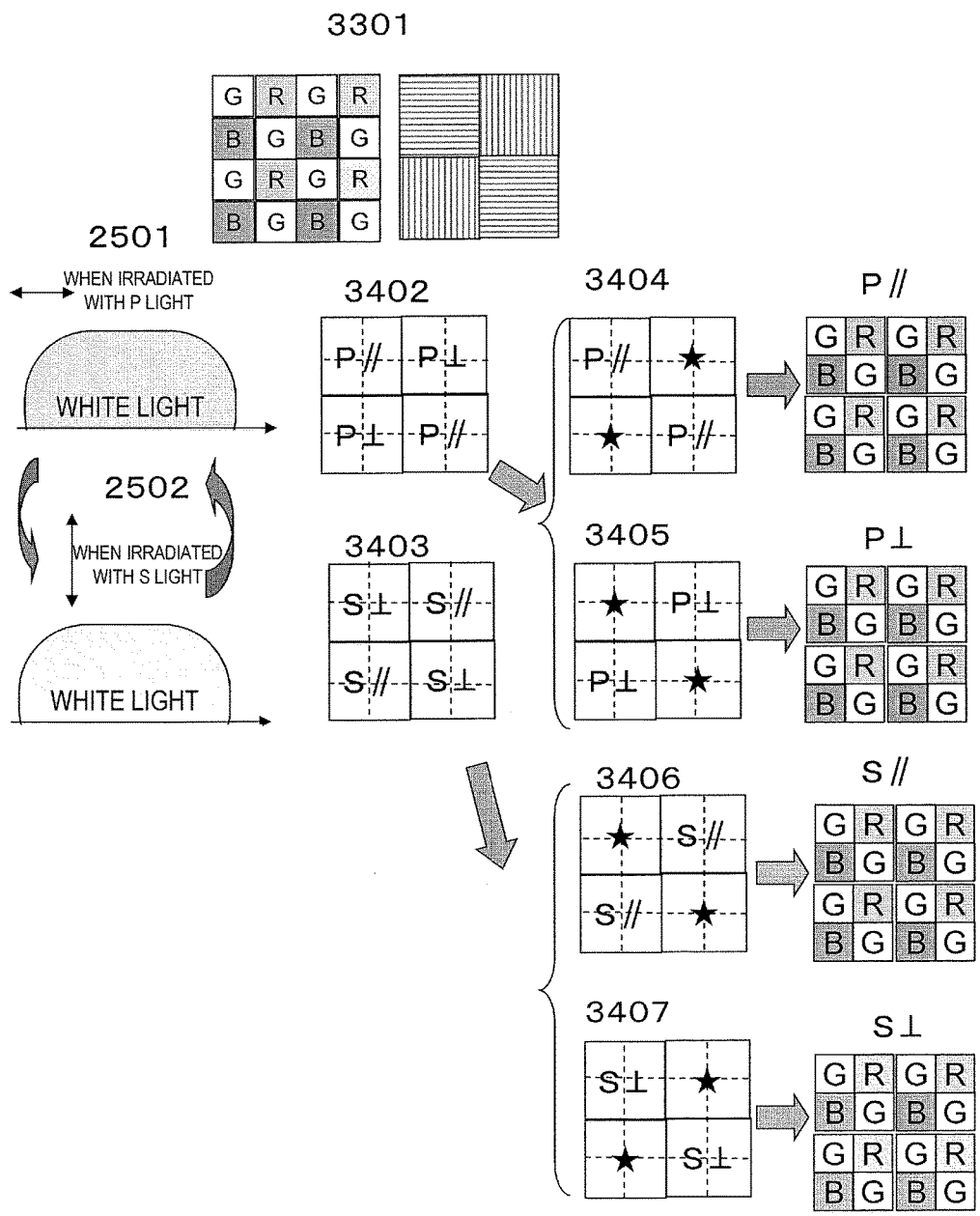
FIG. 34 illustrates how the polarization mosaic processing section 202 operates in the polarization image capturing mode according to the second modified example of the second embodiment of the present disclosure.

FIG. 34 illustrates how the image processing apparatus of this embodiment operates in the polarization image capturing mode, in which the object is alternately irradiated with a P-polarized light beam and an S-polarized light beam and images are captured and polarization pixel patterns 3402 and 3403 are obtained every time the object is irradiated with such a polarized light beam.

Using both of these polarization pixel patterns 3402 and 3403, the polarization mosaic processing section 202 collects and fills with P// and S// and P⊥ and S⊥ for each pixel in question and makes interpolation on the portions indicated by ★ using surrounding pixels. In this manner, parallel and crossed Nicols images 3404 and 3405 under a P-polarized illuminating light beam and parallel and crossed Nicols images 3406 and 3407 under an S-polarized illuminating light beam are generated separately.

A color mosaic interpolation is carried out on the color mosaic image obtained as a result of this processing, thereby generating four kinds of full-color polarization images, which are subjected to the same processing by the depressed region detecting section 204 and the image synthesizing section 206 as what has already been described for the first embodiment. It should be noted that the timing chart for this embodiment is the same as the timing chart for the second embodiment.

MODIFIED EXAMPLE 3 OF EMBODIMENT 2

FIGS. 35 to 39 illustrate a third modified example of the second embodiment of the present disclosure. This modified example uses the same basic configuration as the second embodiment shown in FIG. 20. In this modified example, however, the linearly polarized illuminating light irradiates the object at a different angle and the polarization mosaic of the polarization image sensor on the receiving end has a different transmission plane. In this embodiment, to detect and enhance a group of grooves which are present on the surface of the object with a random distribution of directions on average without prioritizing only a particular direction of the grooves, the polarized illuminating light is supposed to irradiate the object at an angle of 45 degrees, not at right angles.

Figure 35:
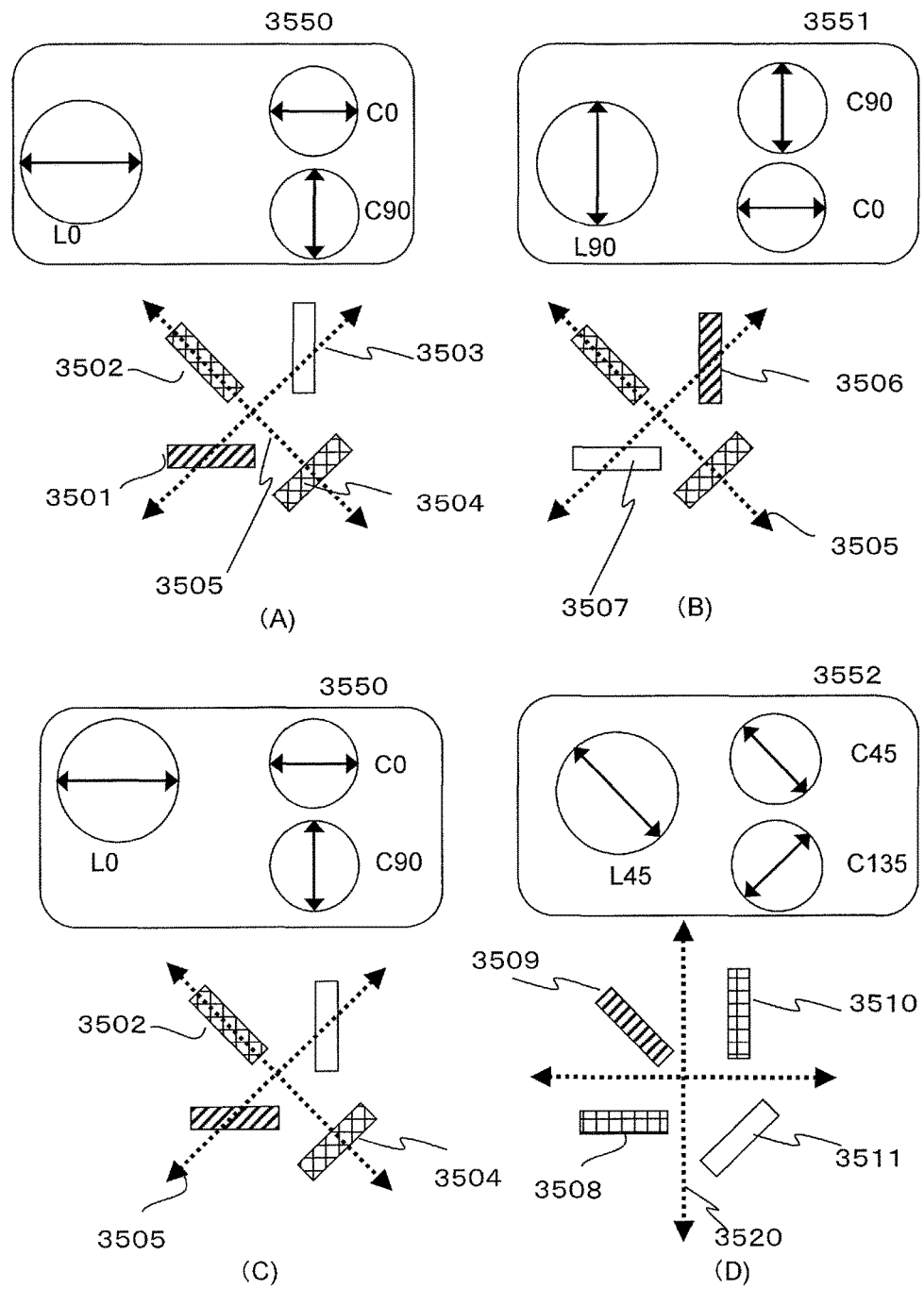
FIG. 35 illustrates relations between the polarized illuminating light and the polarization image transmission direction in a third modified example of the second embodiment of the present disclosure.

FIGS. 35(A) and 35(B) illustrate a relation between the polarized illuminating light and the polarization image transmission direction which has been used in the first and second embodiments. First of all, in Potion (A) of FIG. 35, the reference numeral 3550 denotes a condition on the polarization direction of illuminating light and polarization directions on the receiving end for use to perform this image capturing session. The rectangles 3501 to 3504 represent surface grooves which run in 0, 45, 90 and 135 degree directions, respectively. In this case, in response to incoming L0 (P-polarized light), an L0C0 (P//) image and an L0C90 (P⊥) image are captured at polarized light transmission angles of C0 and C90, respectively, and a differential polarization image is generated based on these two images. As shown in Table 1, when the differential polarization image is generated, the contrast ratio becomes the highest in the grooves 3502 and 3504 which define angles of 45 and 135 degrees, respectively, with respect to the polarization direction of the illuminating light, becomes the second highest in the groove 3501 which defines an angle of 0 degrees with respect to (i.e., is parallel to) the polarization direction of the illuminating light, and becomes the lowest in the groove 3503 which intersects with the polarization direction of the illuminating light at right angles. In FIGS. 35(A) and 35(B), the respective levels of the contrast ratios of these grooves are represented by the grid, the oblique lines, and the open rectangle in the descending order. Also, the crossed arrows 3505 indicate the directions in which the contrast ratio becomes maximum (in other words, the direction of the groove prioritized).

Next, as shown in potion (B) of FIG. 35, on a condition 3551, in response to incoming L90 (S-polarized light), an L90C90 (S//) image and an L90C0 (S⊥) image are captured at polarized light transmission angles of C90 and C0, respectively. As shown in Table 1, when the differential polarization image is generated, the contrast ratio becomes the highest in the grooves 3502 and 3504 which define angles of 45 and 135 degrees, respectively, with respect to the polarization direction of the illuminating light, becomes the second highest in the groove 3506 which defines an angle of 0 degrees with respect to (i.e., is parallel to) the polarization direction of the illuminating light, and becomes the lowest in the groove 3507 which intersects with the polarization direction of the illuminating light at right angles. Thus, as already described for the first embodiment of the present disclosure, if the results obtained under these two kinds of polarized illuminating light beams are added together and their average is calculated, contrast ratios of substantially the same level are obtained in the grooves 3502 and 3504 defining the 45 and 135 degree directions. As for the grooves defining the 0 and 90 degree directions, on the other hand, the order of the contrast ratio levels in potion (B) of FIG. 35 becomes opposite from that of the contrast ratio levels in Potion (A) of FIG. 35. As a result, the total performance can be improved because the groove directions in which the contrast ratio becomes the lowest are dispersed. Consequently, the grooves that are distributed in random directions can be detected and enhanced just as intended.

However, as can be seen easily from the results shown in FIGS. 35(A) and 35(B), the prioritized groove directions are indicated in both cases by the crossed arrows 3505. That is why among those grooves running in the four directions, the highest performance is achieved in the grooves 3502 and 3504 in both cases. Thus, it can be said that the grooves running in the 45 and 135 degree directions are given a higher priority than the grooves running in the 0 and 90 degree directions. That is to say, the surface grooves with random directivity were not treated quite equally with each other.

Thus, to overcome this problem, the polarization directions of the illuminating light are changed into L0 and L45 and crossed and parallel Nicols images are captured under each of these two polarized illuminating light beams as shown in FIGS. 35(C) and 35(D). In this case, the situation does not change as for L0 under the condition 3550. However, if L45 representing polarized illuminating light with a polarization direction of 45 degrees is called "T-polarized light", then an L45C45 (T//) image and an L45C135 (T⊥) image will be generated and a differential polarization image will be obtained based on these two images. In that case, the highest contrast ratio will be achieved in the grooves 3508 and 3510 running in the 0 and 90 degree directions, respectively, and defining an angle of 45 degrees with respect to the polarization direction of the illuminating light, the second highest contrast ratio will be achieved in the groove 3509 running in the 45 degree direction parallel to the polarization direction of the illuminating light, and the contrast ratio will be the lowest in the groove 3511 running in the 135 degree direction and intersecting with the polarization direction of the illuminating light at right angles. That is to say, the crossed arrows indicating the prioritized groove directions change as indicated by the reference numeral 3520. Thus, if the results shown in FIGS. 35(C) and 35(D) are added together and their average is calculated, among the grooves running in the four directions, the highest contrast ratio will be achieved in the grooves 3502 and 3504 running in the 45 and 135 degree directions under L0 shown in potion (C) of FIG. 35 and in the grooves 3508 and 3510 running in the 0 and 90 degree directions under L45 shown in potion (D) of FIG. 35. As a result, an equally high contrast ratio can be achieved in each of the grooves running in the four directions, and therefore, even grooves with a random distribution of directions can be evaluated equally without prioritizing any particular one of the four directions.

Figure 36:
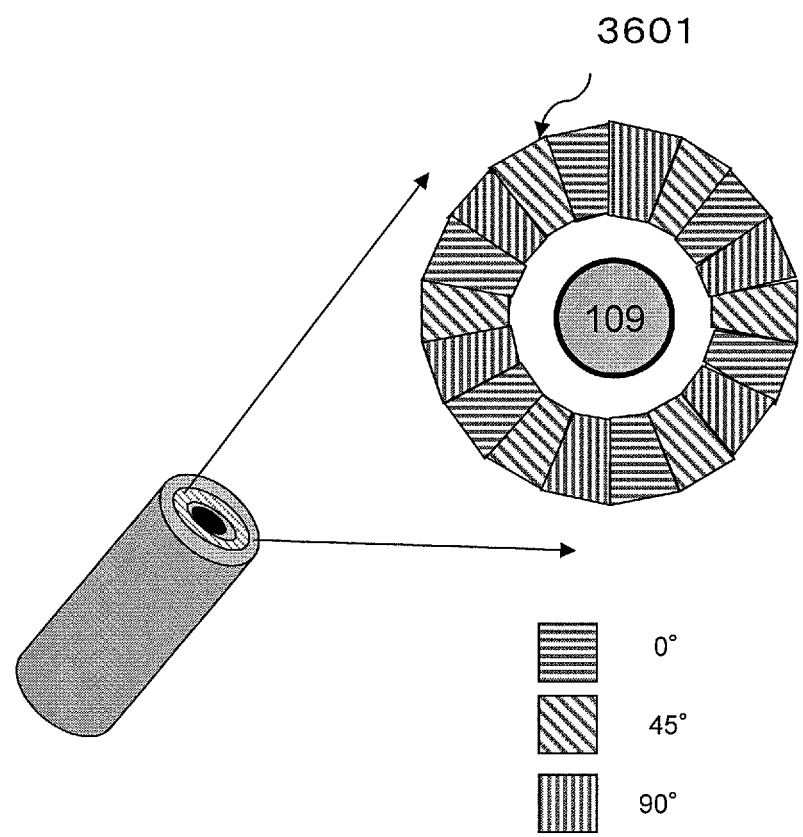
FIG. 36 illustrates a polarized illuminating light source according to the third modified example of the second embodiment of the present disclosure.

FIG. 36 corresponds to FIG. 21. In this embodiment, a number of (e.g., eighteen in this example) emission ports, through which three kinds of illuminating light beams, of which the polarization planes define 0, 45 and 90 degrees, respectively, are emitted alternately, are arranged at the tip of the endoscope. In this example, by lighting one of the three sets of illuminating elements, each consisting of six elements that are arranged in every third port to use polarizers of the same type, selectively, the object can be irradiated with these three kinds of polarized illuminating light beams spatially equally. The number of illuminating elements does not have to be eighteen. In any case, however, non-polarized light should be able to be generated by mixing the polarized light beams together, and the object should be irradiated with two kinds of linearly polarized light beams at an interval of 45 degrees.

Figure 37:
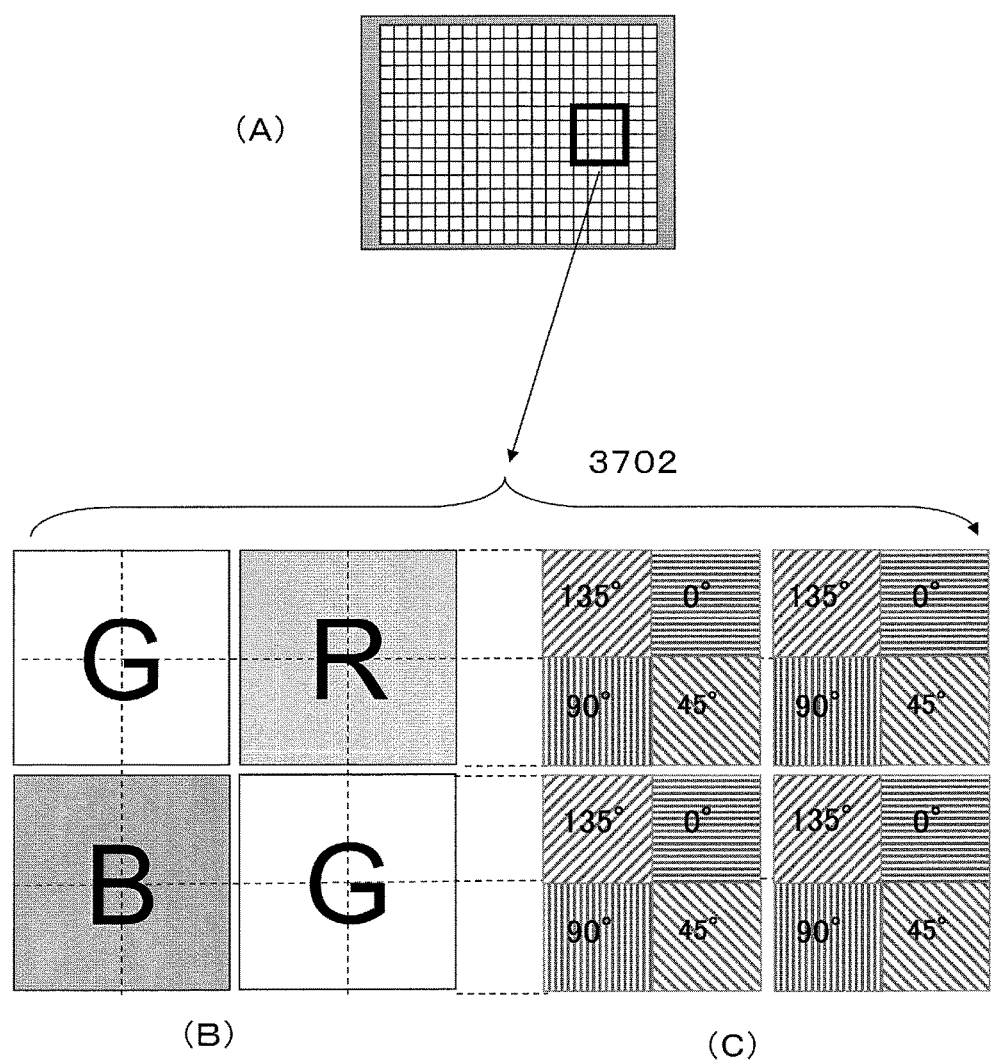
FIG. 37 illustrates a planar layout of a color mosaic and a polarization mosaic according to the third modified example of the second embodiment of the present disclosure.

FIG. 37 illustrates a planar structure of a color polarization image sensor 119 according to this comparative example, and corresponds to FIG. 24. Portion (A) of FIG. 37 illustrates the same planar structure as a color single-panel image sensor. In FIG. 37, the polarization mosaic structure is comprised of four kinds of elements with polarization directions of 0, 45, 90 and 135 degrees, respectively, which is the only difference from FIG. 24.

Figure 38:
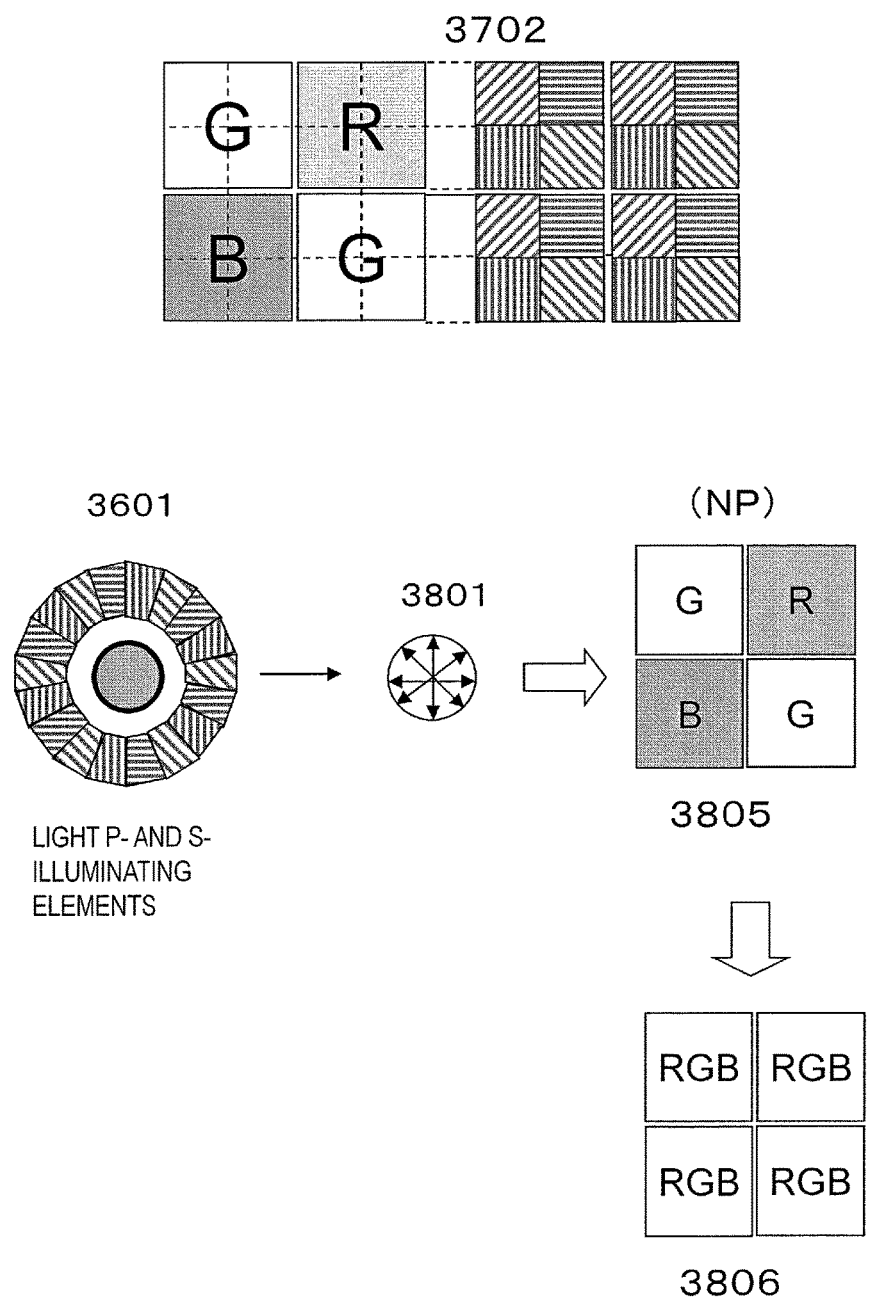
FIG. 38 illustrates how the apparatus operates in a normal image capturing mode in the third modified example of the second embodiment of the present disclosure.

FIG. 38 illustrates how this comparative example operates in a normal image capturing mode. The object is irradiated simultaneously with light beams emitted from 0 degree (P) and 90 degree (S) illuminating elements that are turned ON at the same time in the polarized illuminating source 3601. And every time the object is irradiated with the light beam, a polarization color mosaic image is captured. Since two kinds of illuminating elements emitting linearly polarized light beams, of which the polarization directions intersect with each other at right angles, are turned ON, the illuminating light becomes non-polarized light 3801. And by adding together the outputs of the four kinds of polarization mosaics within each color pixel 3702 and calculating their average, a non-polarized (NP) color mosaic image 3805, of which the resolution has decreased to a quarter (=½×½) of the original one, is obtained. The processing of generating a full color image 3806 based on this non-polarized color mosaic image 3805 may be carried out by ordinary color mosaic interpolation technique.

Figure 39:
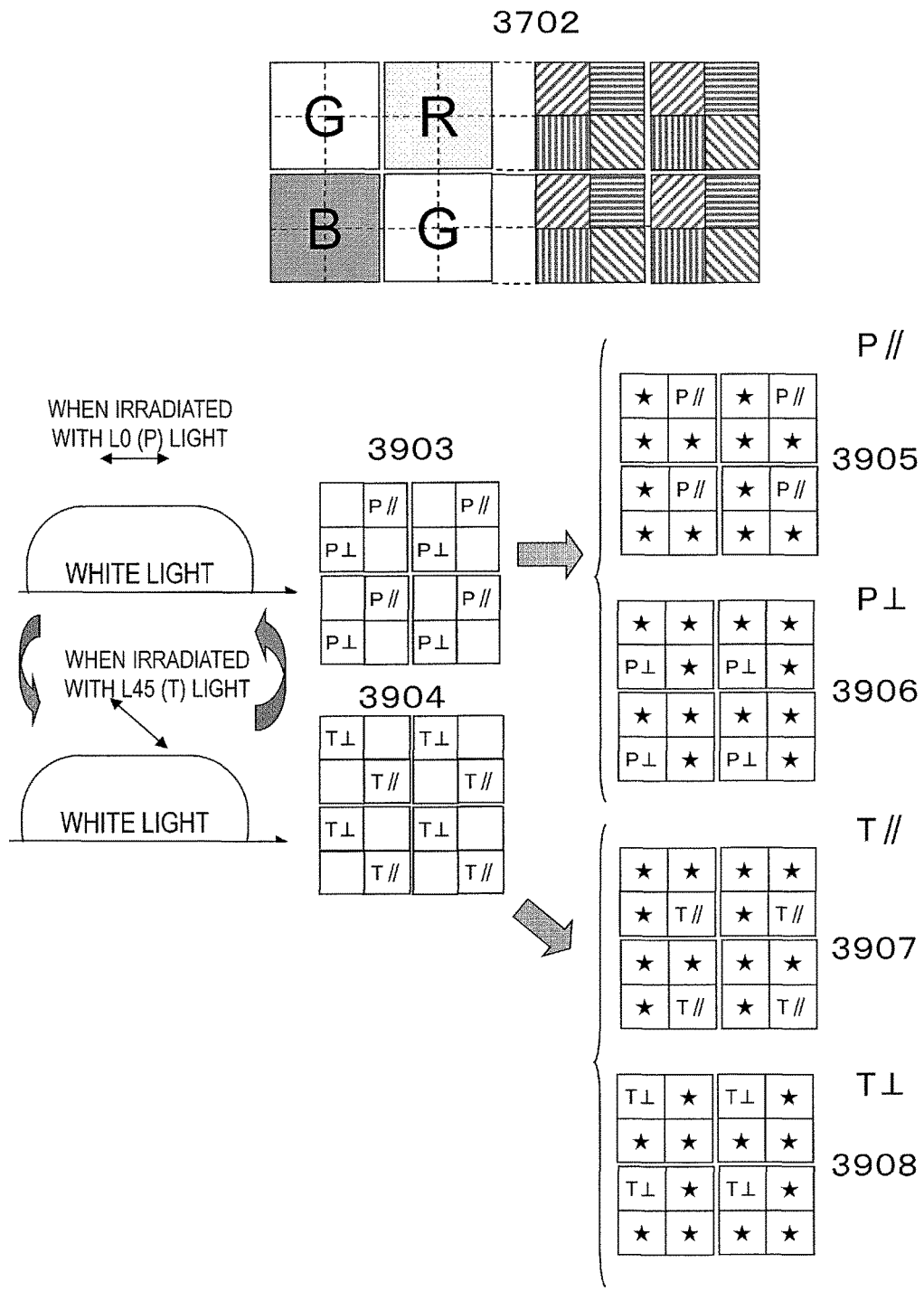
FIG. 39 illustrates how the apparatus operates in a polarization image capturing mode in the third modified example of the second embodiment of the present disclosure.

FIG. 39 illustrates how this comparative example operates in the polarization image capturing mode. In the polarization image capturing mode, the object is alternately irradiated with an L0 (P-polarized) light beam and an L45 (S-polarized) light beam, and polarization color mosaic pixel patterns 3903 and 3904 are obtained each time. The polarization mosaic processing section 202 performs selective integration processing on P// and P⊥ and T// and T⊥ for each pixel in question using both of the pixel patterns 3903 and 3904, and makes interpolation using surrounding pixels as for unavailable pixels, thereby generating four kinds of polarization images, namely, parallel and crossed Nicols images 3905 and 3906 under the P-polarized illuminating light and parallel and crossed Nicols images 3907 and 3908 under the T-polarized illuminating light, separately from each other. In FIG. 39, the solid stars ★ indicate pixels to be interpolated.

The four kinds of polarization images that are obtained as a result of this processing are subjected to the same processing as what has already been described for the first embodiment with reference to FIGS. 14 and 17A by the depressed region detecting section 204 and the image synthesizing section 206.

MODIFIED EXAMPLE 4 OF EMBODIMENT 2

FIGS. 40 to 43 illustrate a fourth modified example of the second embodiment of the present disclosure. This modified example uses the same basic configuration as the second embodiment shown in FIG. 20. In this modified example, however, a circularly polarized light beam is used instead of the linearly polarized light beam as the illuminating light, and therefore, a λ/4 plate is provided for each of the polarized illuminating light source and the polarization image capturing section. By using a circularly polarized light beam as the illuminating light, grooves with a random distribution of directions on the surface of the object can be detected on average.

Figure 40:
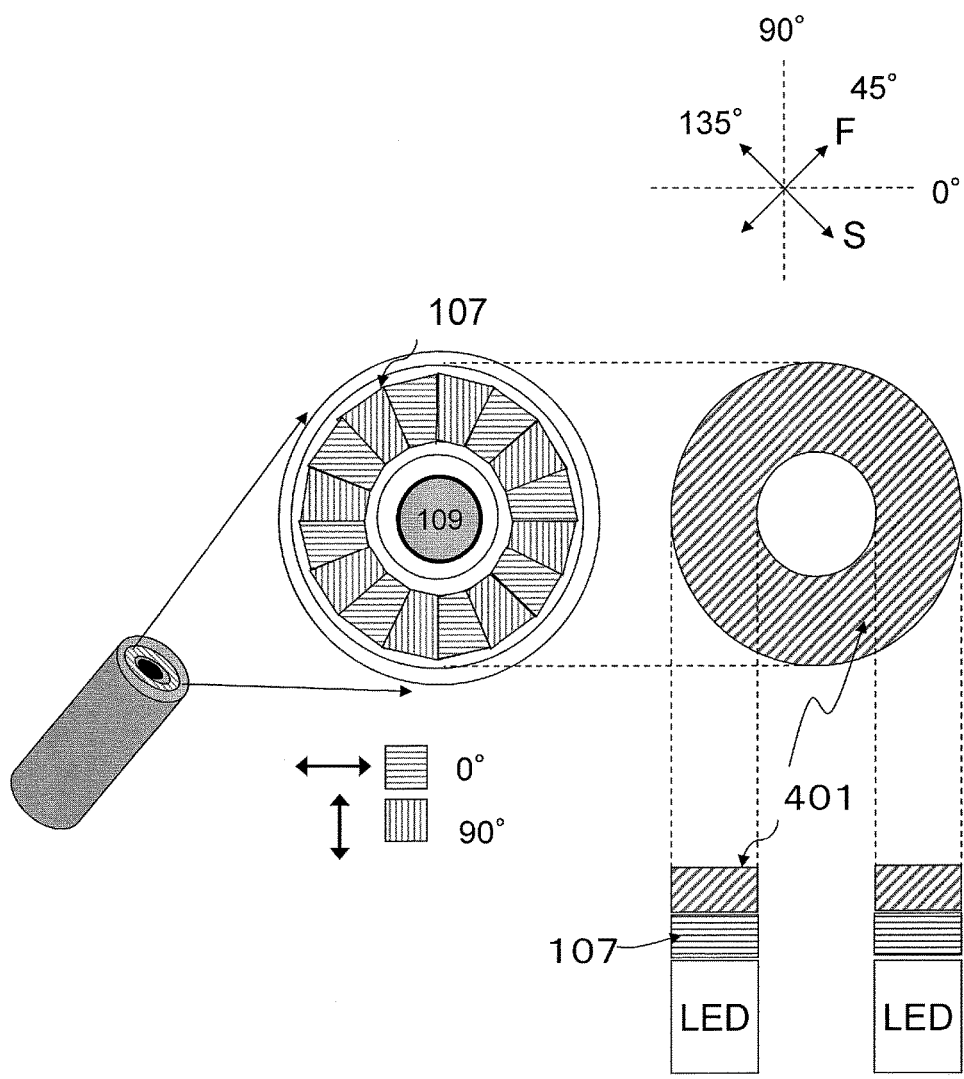
FIG. 40 illustrates the tip of an endoscope and a rotating polarized illuminating light source according to a fourth modified example of the second embodiment of the present disclosure.

FIG. 40 illustrates an exemplary configuration for the tip of an endoscope for use in this modified example, and corresponds to FIG. 21 that has already been referred to for the second embodiment. As shown in FIG. 40, at the tip of the endoscope, a λ/4 plate 401, a polarization lens 107 and an LED light source are stacked in this order one upon the other so that the λ/4 plate 401 is located closest to the object. In the LED light source, LED elements emitting linearly polarized light, of which the polarization plane defines a polarization direction of 0 degrees, and LED elements emitting linearly polarized light, of which the polarization plane defines a polarization direction of 90 degrees, are arranged alternately along the circumference. The number of those LED elements provided may be eighteen, for example. The λ/4 plate 401 is arranged so that its optic axis defines a tilt angle of 45 degrees with respect to the polarization plane of the light emitted from the LED elements. In FIG. 40, the reference signs F and S respectively denote the fast axis and slow axis of the λ/4 plate 401.

By lighting an array of LED elements, of which the polarization plane defines a polarization direction of 0 degrees, and an array of LED elements, of which the polarization plane defines a polarization direction of 90 degrees, alternately and selectively, the object can be irradiated with a clockwise circularly polarized light beam and a counterclockwise circularly polarized light beam temporally alternately and spatially substantially evenly.

Next, the relation between the polarization plane direction of the linearly polarized light emitted from the LED elements, the F (fast) and S (slow) axis directions of the λ/4 plate, and the rotation direction of the circularly polarized light will be described with reference to FIGS. 41A to 41B.

Figure 41A:
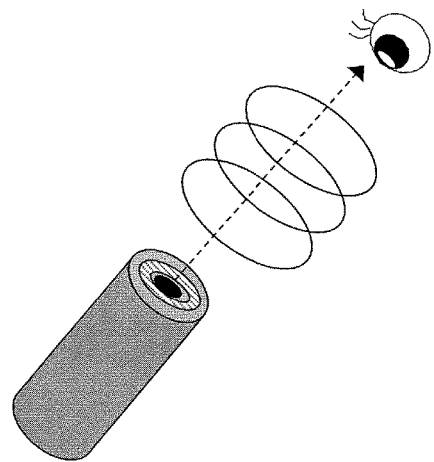
FIG. 41A illustrates how a circularly polarized light beam travels.
Figure 41B:
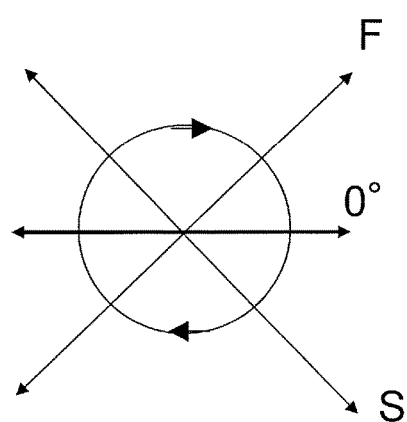
FIG. 41B illustrates how a linearly polarized light beam, of which the polarization plane defines a 0 degree polarization direction, is incident on a λ/4 plate between its F and S axes.
Figure 41C:
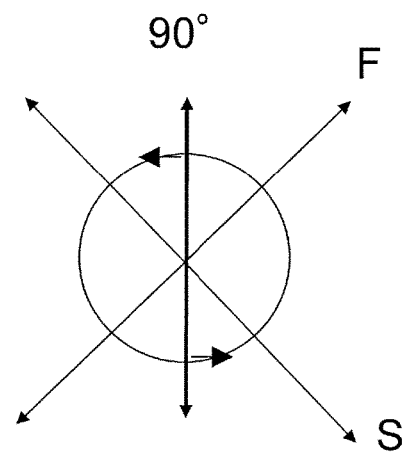
FIG. 41C illustrates how a linearly polarized light beam, of which the polarization plane defines a 90 degree polarization direction, is incident on the λ/4 plate between its F and S axes.

The rotation direction of the circularly polarized light is defined by looking at the light from a direction toward which the light travels as shown in FIG. 41A. If linearly polarized light with a polarization plane of 0 degrees is incident between the F and S axes of the λ/4 plate which are arranged at an angle of 45 degrees obliquely, then clockwise circularly polarized light is obtained as shown in FIG. 41B. On the other hand, if linearly polarized light with a polarization plane of 90 degrees is incident between the F and S axes of the λ/4 plate which are arranged at an angle of 45 degrees obliquely, then counterclockwise circularly polarized light is obtained as shown in FIG. 41C.

Figure 42:
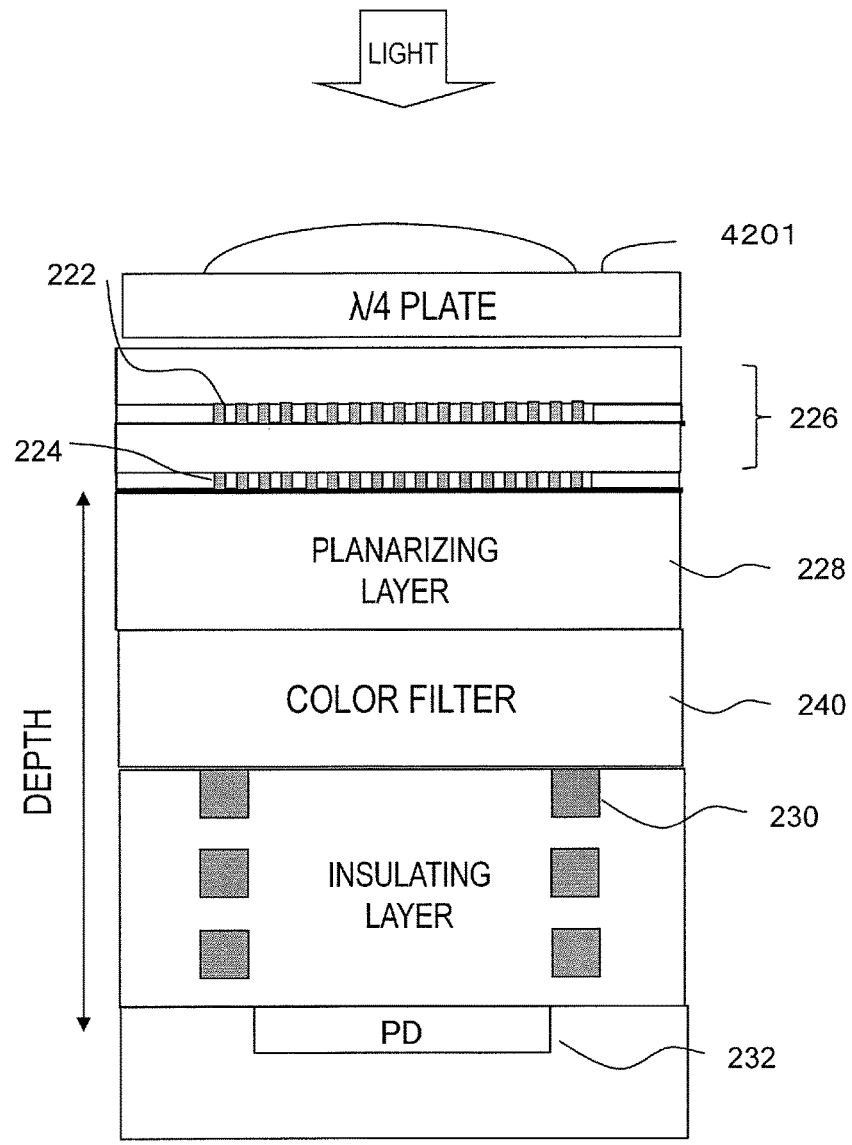
FIG. 42 illustrates an exemplary cross-sectional structure of a color polarization image sensor 119 for use in the fourth modified example of the second embodiment of the present disclosure.

FIG. 42 illustrates an exemplary cross-sectional structure for a color polarization image sensor 119 for use in a modified example of this embodiment. In FIG. 42, the λ/4 plate 4201 is arranged over the wire grid layers 222 and 224, which is the only difference from the configuration shown in FIG. 23.

Figure 43:
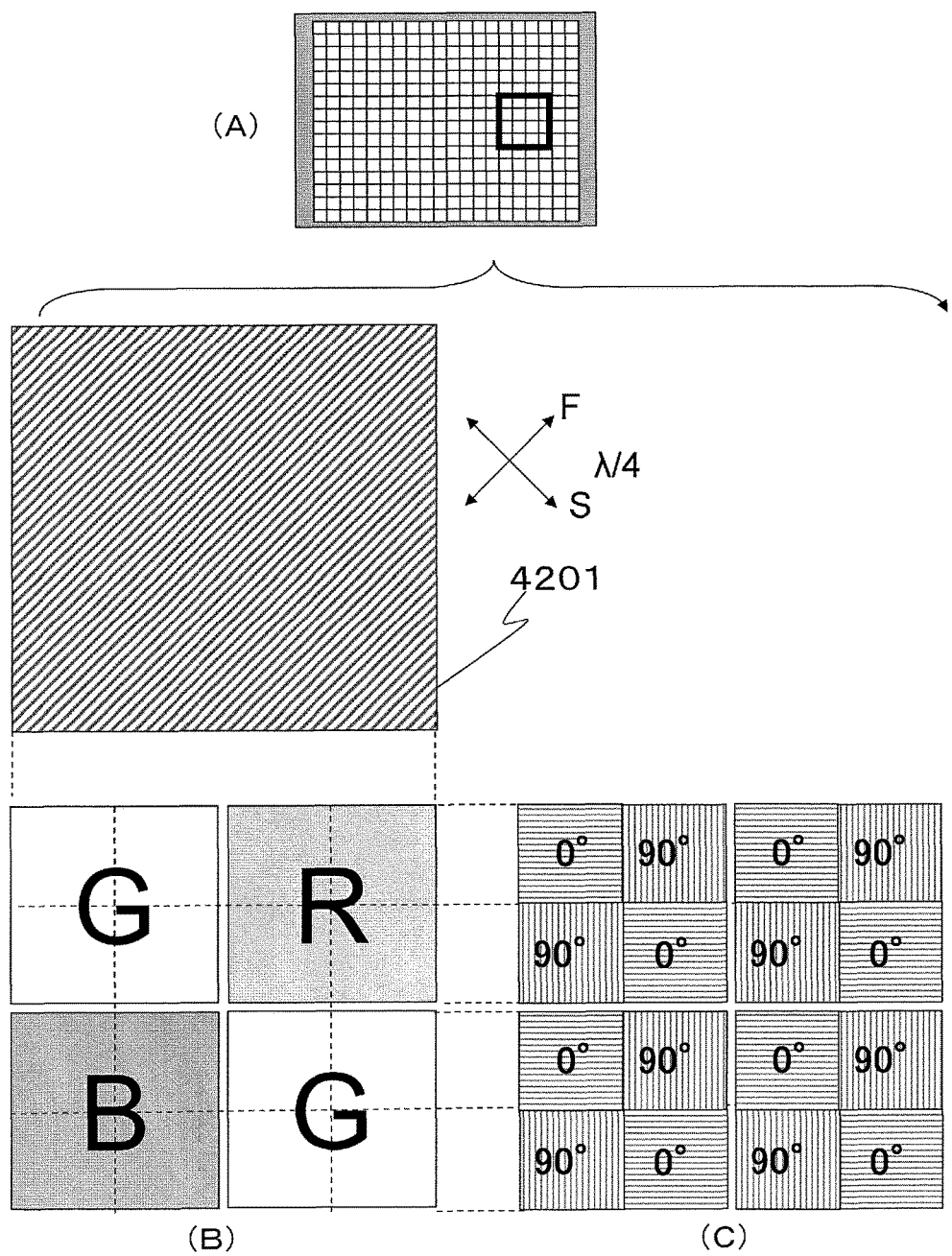
FIG. 43 illustrates a planar layout of a color mosaic and a polarization mosaic according to the fourth modified example of the second embodiment of the present disclosure.

FIG. 43 illustrates a planar structure of the color polarization image sensor 119 and corresponds to FIG. 24. In FIG. 43, a λ/4 plate 4201 with F and S axes is arranged to cover the wire-grid polarizer entirely, which is a difference from the configuration shown in FIG. 24. When incident on the λ/4 plate 4201 which is arranged so that the F and S axes face appropriate directions, circularly polarized light is transformed into linearly polarized light with a predetermined polarization direction, which can transmit the λ/4 plate 4201. The λ/4 plate 4201 may be arranged so that the F and S axes face 135 and 45 degree directions, respectively, to make the polarization planes of the linearly polarized light incident on the wire-grid polarizer array define 0 and 90 degree directions, respectively.

Figure 44:
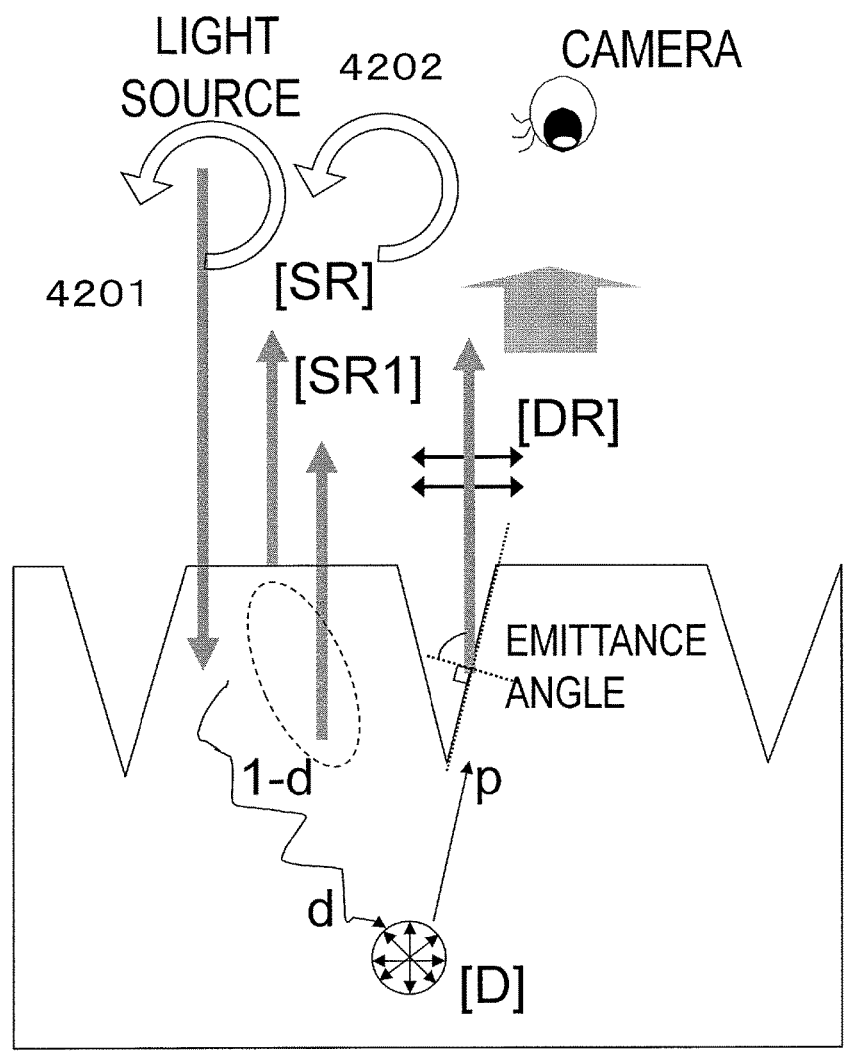
FIG. 44 illustrates, as a model, a cross section of a micro-geometric structure on the surface mucosa of an organ adopted in the fourth modified example of the second embodiment of the present disclosure.

FIG. 44 illustrates a cross section of the mucosa surface of an organ as a model for this modified example. In this example, suppose the object is irradiated with clockwise circularly polarized illuminating light, which has been produced by making the linearly polarized light with a 0 degree polarization direction shown in FIG. 41B be transmitted through the λ/4 plate. The light reflected from a smooth and translucent mucosa surface is surface halation [SR]. According to the camera coordinates shown in FIG. 42, the halation [SR] returns, along with the reflected light [SR1] coming back from a shallow level in the mucosa layer, as counterclockwise circularly polarized light 4202. That is why when transmitted through the λ/4 plate of the image capturing system, the circularly polarized light 4202 will turn into linearly polarized light with a 90 degree polarization direction and then cut by a wire-grid polarizer with a 0 degree polarization direction. That is to say, the light returning from a surface layer of the object will be cut by a polarizer, of which the polarization plane defines the same polarization direction as that of the linearly polarized light incident on the λ/4 plate of the illumination system. On the other hand, the halation [SR] and the reflected light [SR1] returning from a shallow level in the mucosa layer can be transmitted through a polarizer, of which the polarization plane defines a direction that intersects at right angles with that of the linearly polarized light incident on the λ/4 plate of the illumination system.

Meanwhile, the light [DR] returning from a deep level in the object's mucosa layer has once had its circular polarization canceled and turned into non-polarized light at the deep level of the mucosa layer. And when going out of a groove on the surface of the object, the non-polarized light turns into linearly polarized light, of which the polarization direction intersects at right angles with the groove. In such a situation, there will be two possible cases depending on the direction in which the groove runs.

Figure 45:
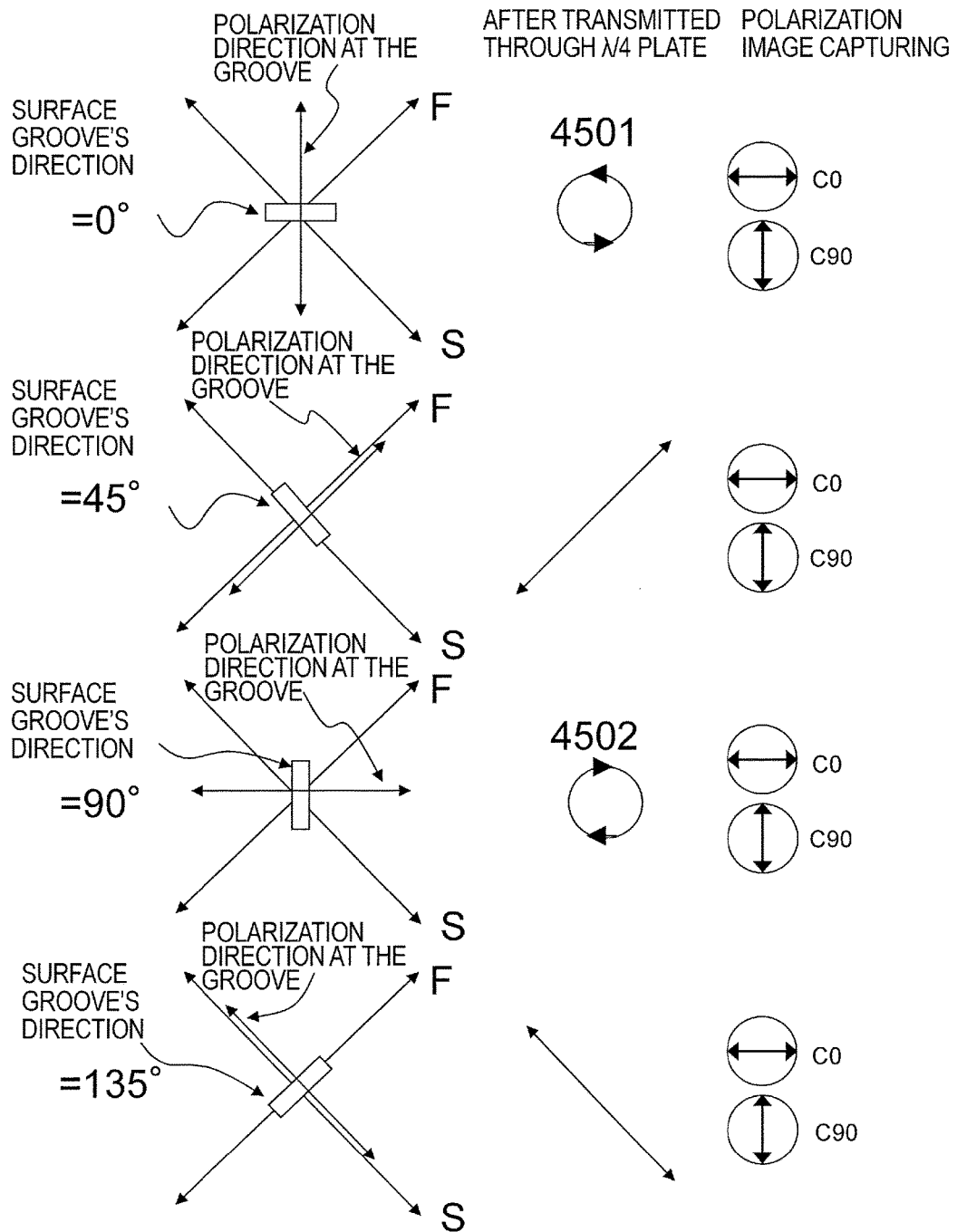
FIG. 45 illustrates returning light in the fourth modified example of the second embodiment of the present disclosure.

FIG. 45 illustrates those two possible cases for the polarized light.

(CASE 1): If the surface grooves run in 0 and 90 degree directions, the polarization plane direction of the linearly polarized light beams returning from the grooves will be located at almost an intermediate position between the F and S axes. That is why the linearly polarized light beams will be transformed into circularly polarized light beams 4501 and 4502 by the λ/4 plate 4201 and transmitted through polarizers, of which the polarization planes define 0 and 90 degree directions, on the image sensor end. As a result, on the image sensor end, the light intensity to be observed at both 0 and 90 degrees will be a half as high as that of the polarized light component that has gone out of the groove, and the amounts of transmitted light will be equal to each other.

(CASE 2): If the surface grooves run in 45 and 135 degree directions, the polarization plane direction of the linearly polarized light beams going out of the grooves will be parallel to the F-axis direction (135 degrees) and the S-axis direction (45 degrees), respectively. That is why the linearly polarized light beams will be transmitted as they are through polarizers, of which the polarization planes define 0 and 90 degree directions, on the image sensor end with being affected by the λ/4 plate 4201. As a result, the amounts of the transmitted light will decrease to a half for both of the two light beams. Consequently, in both of these CASES 1 and 2, if polarization observed value differential processing is carried out at 0 and 90 degrees on the image sensor end, the value will be ideally zero (representing black) in the groove region. As a result, the contrast ratio of the micro-geometric structure formed by the depressions and projections at shallow levels in the mucosa will increase more significantly than in the plane region.

MODIFIED EXAMPLE 5 OF EMBODIMENT 2

In the fourth modified example of the second embodiment described above, the object is sequentially irradiated with clockwise circularly polarized light and counterclockwise circularly polarized light. However, the object does not always have to be irradiated with two kinds of circularly polarized light beams. In this modified example, the polarizer shown in FIG. 40 is modified so that its only polarization direction will be either a 0 degree direction or a 90 degree direction and the object is irradiated with only clockwise circularly polarized light or counterclockwise circularly polarized light without turning ON the illuminating elements sequentially.

Figure 46:
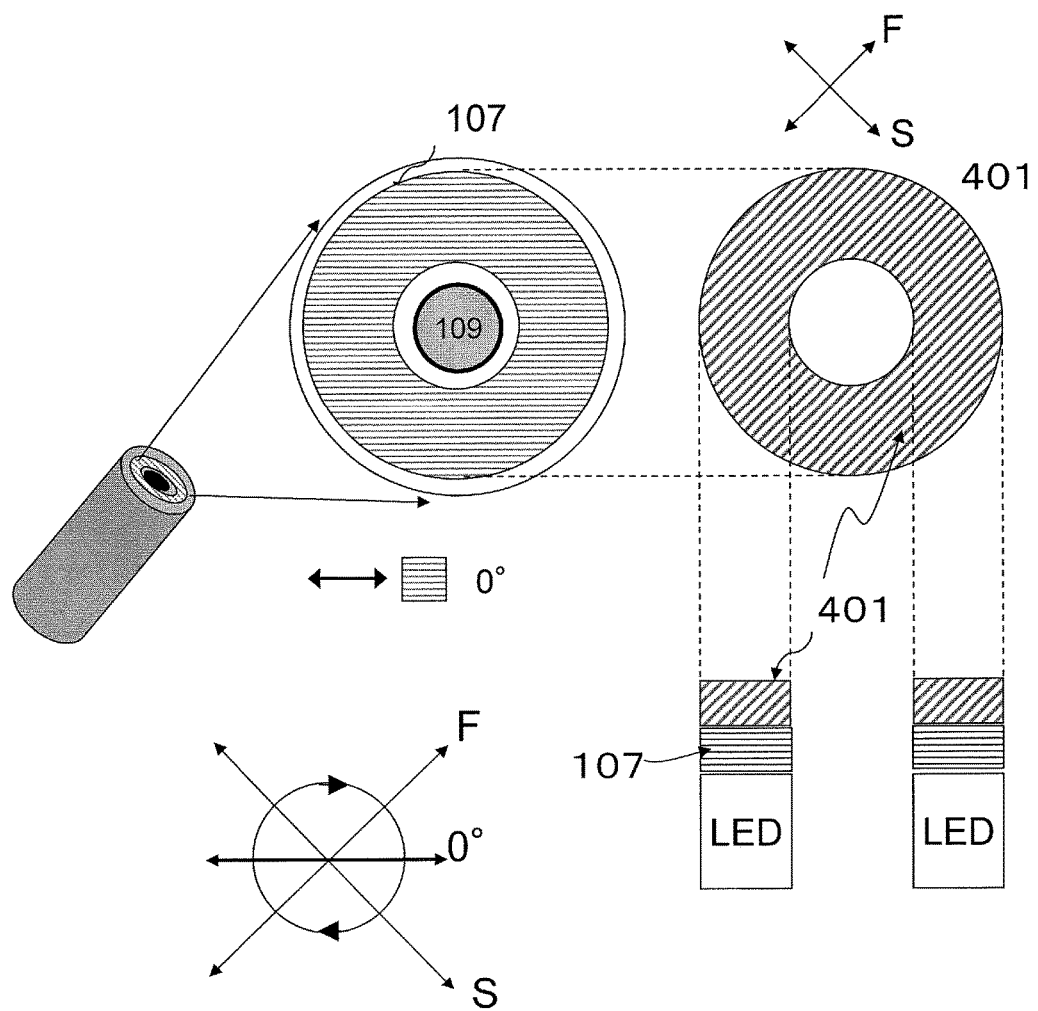
FIG. 46 illustrates the tip of an endoscope and a rotating polarized illuminating light source according to a fifth modified example of the second embodiment of the present disclosure.

FIG. 46 illustrates an exemplary configuration for a light source which may be used in this modified example. The LED light source does not have to be a divided light source. Thus, the illuminance of the illuminating light to be used to perform a single image capturing session can be doubled compared to the fourth modified example. In addition, since there is no need to perform two image capturing sessions with the polarization direction of the illuminating light changed, the amount of time it takes to get the image captured can be halved.

The configuration on the image sensor end of this fifth modified example may be the same as that of the fourth modified example described above. As already described for the fourth modified example, the contrast ratio of the microgeometric structure at shallow levels in the mucosa can be increased by performing the polarization differential processing.

Furthermore, LED elements do not have to be used as the light source elements, either. That is why non-polarized illuminating light which uses a conventional light guide may be transformed into circularly polarized light at the tip of an endoscope.

As in the first embodiment described above, even in a plane sequential irradiating endoscope, if a polarizer and a λ/4 plate are arranged at the emission port of the illumination as shown in FIG. 46, RGB circularly polarized light can also be produced and the effect of this fifth modified example can be achieved.

In the embodiments described above, the illuminating section is supposed to irradiate the object with non-polarized illuminating light in the non-polarization image capturing mode and emit the first and second illuminating light beams sequentially so that the wavelength range of the first illuminating light beam has a portion which does not overlap with the wavelength range of the second illuminating light beam. However, the illuminating section according to the present disclosure does not always have to operate in such a non-polarization image capturing mode. Also, in the embodiments described above, the polarization mosaic processing section can obtain a non-polarization image which is produced by a signal representing the light transmitted through each polarizer when the object is irradiated with non-polarized illuminating light in the non-polarization image capturing mode. However, the polarization mosaic processing section according to the present disclosure does not have to obtain such a non-polarization image to be captured in such a non-polarization image capturing mode.

Embodiments of the present disclosure are broadly applicable to the field of image processing that needs observing, checking, or recognizing the object's surface topography using a medical endoscope camera for digestive organs, a medical camera for dermatologists, dentists, internists or surgeons, an industrial endoscope camera, a fingerprint scanner, or an optical surface analyzer for use in a factory, for example. According to an embodiment of the present disclosure, even the surface topography of a smooth transparent object or translucent object can also be detected accurately, and can be presented in an enhanced form so as to be easily sensible to a human viewer. As a result, the surface topography which is difficult to check just by measuring the light intensity can be checked out very effectively according to an embodiment of the present disclosure.

An image processing apparatus according to the present disclosure is also applicable to digital cameras, camcorders and surveillance cameras, and can be used extensively to increase the contrast ratio when shooting on the surface of water or in the air or when shooting through glass.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An image processing apparatus comprising:
   an illuminating section which sequentially irradiates an object with a first illuminating light beam that is polarized in a first direction and with a second illuminating light beam that is polarized in a second direction that intersects with the first direction in a polarization image capturing mode;
   an image sensor including a polarization mosaic array in which a plurality of polarizers with mutually different polarization transmission axis directions are arranged and a photosensing element array which receives light that has been transmitted through each said polarizer and which outputs a signal;
   a polarization mosaic processing section which obtains, in the polarization image capturing mode, a first polarization image to be generated based on a signal representing light that has been transmitted through a polarizer that has the polarization transmission axis in a direction parallel to the first direction while the object is being irradiated with the first illuminating light beam, a second polarization image to be generated based on a signal representing light that has been transmitted through a polarizer that has the polarization transmission axis in a direction intersecting with the first direction while the object is being irradiated with the first illuminating light beam, a third polarization image to be generated based on a signal representing light that has been transmitted through a polarizer that has the polarization transmission axis in a direction parallel to the second direction while the object is being irradiated with the second illuminating light beam, and a fourth polarization image to be generated based on a signal representing light that has been transmitted through a polarizer that has the polarization transmission axis in a direction intersecting with the second direction while the object is being irradiated with the second illuminating light beam;
   a depressed region detecting section which detects a depressed region on the surface of the object based on both the first and second polarization images that form one pair and the third and fourth polarization images that form another pair; and
   an image forming section which forms an image that represents the depressed region on the object's surface in an enhanced form.

2. The image processing apparatus of claim 1, wherein the depressed region detecting section generates a first depressed region enhanced image by changing the color component ratio of a first polarization differential image representing the differential value between the first and second polarization images, also generates a second depressed region enhanced image by changing the color component ratio of a second polarization differential image representing the differential value between the third and fourth polarization images, and outputs the average of the sum of the first and second depressed region enhanced images.

3. The image processing apparatus of claim 1, wherein the depressed region detecting section generates a third depressed region enhanced image by changing the color component ratio of a third polarization differential image representing the differential value between the first and fourth polarization images, also generates a fourth depressed region enhanced image by changing the color component ratio of a fourth polarization differential image representing the differential value between the third and second polarization images, and outputs the average of the sum of the third and fourth depressed region enhanced images.

4. An image processing apparatus comprising:
an illuminating section which sequentially irradiates an object with a first white illuminating light beam that is polarized in a first direction and with a second white illuminating light beam that is polarized in a second direction that intersects with the first direction in a polarization image capturing mode;
an image sensor including a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each said polarizer and each said color filter and which outputs a signal;
a polarization mosaic processing section which obtains, in the polarization image capturing mode, a first polarization image to be generated based on a signal representing light that has been transmitted through a polarizer that has the polarization transmission axis in a direction parallel to the first direction while the object is being irradiated with the first white illuminating light beam, a second polarization image to be generated based on a signal representing light that has been transmitted through a polarizer that has the polarization transmission axis in a direction intersecting with the first direction while the object is being irradiated with the first white illuminating light beam, a third polarization image to be generated based on a signal representing light that has been transmitted through a polarizer that has the polarization transmission axis in a direction parallel to the second direction while the object is being irradiated with the second white illuminating light beam, and a fourth polarization image to be generated based on a signal representing light that has been transmitted through a polarizer that has the polarization transmission axis in a direction intersecting with the second direction while the object is being irradiated with the second white illuminating light beam;
a depressed region detecting section which detects a depressed region on the surface of the object based on both the first and second polarization images that form one pair and the third and fourth polarization images that form another pair; and
an image forming section which forms an image that represents the depressed region on the object's surface in an enhanced form.

5. The image processing apparatus of claim 4, wherein the color mosaic filter includes three kinds of color filters that are R (red), G (green) and B (blue) filters.

6. The image processing apparatus of claim 4, wherein each of the three kinds of color filters is associated with the plurality of polarizers with mutually different polarization transmission axis directions.

7. The image processing apparatus of claim 4, wherein each of the three kinds of color filters is associated with one of the plurality of polarizers.

8. The image processing apparatus of claim 4, wherein the three kinds of color filters in the color mosaic filter form a Bayer arrangement, and
two G (green) filters included in the Bayer arrangement are respectively associated with the plurality of polarizers with mutually different polarization transmission axis directions.

9. The image processing apparatus of claim 4, wherein each of the plurality of polarizers is associated with the three kinds of color filters.

10. The image processing apparatus of claim 4, wherein the depressed region detecting section generates a first depressed region enhanced image by changing the color component ratio of a first polarization differential image representing the differential value between the first and second polarization images, also generates a second depressed region enhanced image by changing the color component ratio of a second polarization differential image representing the differential value between the third and fourth polarization images, and outputs the average of the sum of the first and second depressed region enhanced images.

11. The image processing apparatus of claim 4, wherein the depressed region detecting section generates a third depressed region enhanced image by changing the color component ratio of a third polarization differential image representing the differential value between the first and fourth polarization images, also generates a fourth depressed region enhanced image by changing the color component ratio of a fourth polarization differential image representing the differential value between the third and second polarization images, and outputs the average of the sum of the third and fourth depressed region enhanced images.

12. An endoscope for use in the image processing apparatus of claim 1, the endoscope comprising:
an illuminating section which sequentially irradiates an object with a first illuminating light beam that is polarized in a first direction and with a second illuminating light beam that is polarized in a second direction that intersects with the first direction in a polarization image capturing mode; and
an image sensor including a polarization mosaic array in which a plurality of polarizers with mutually different polarization transmission axis directions are arranged and a photosensing element array which receives light that has been transmitted through each said polarizer and which outputs a signal.

13. An endoscope for use in the image processing apparatus of claim 4, the endoscope comprising:
an illuminating section which sequentially irradiates an object with a first white illuminating light beam that is polarized in a first direction and with a second white illuminating light beam that is polarized in a second direction that intersects with the first direction in a polarization image capturing mode; and
an image sensor including a polarization mosaic array in which a plurality of polarizers with mutually different polarization transmission axis directions are arranged, a color mosaic filter in which color filters with mutually different light transmission properties are arranged, and a photosensing element array which receives light that has been transmitted through each said polarizer and each said color filter and which outputs a signal.

* * * * *